United States Patent [19]
Heise

[11] Patent Number: 6,166,260
[45] Date of Patent: Dec. 26, 2000

[54] TANDEM REDUCTION AND HOST-GUEST COMPLEXATION

[75] Inventor: Glenn L. Heise, Nashua, N.H.

[73] Assignee: Zeeland Chemicals, Inc., Zeeland, Mich.

[21] Appl. No.: 09/369,732

[22] Filed: Aug. 6, 1999

[51] Int. Cl.[7] ...................... C07C 29/143; C07C 29/136; C07C 29/78; C07C 29/92

[52] U.S. Cl. .......................... 568/308; 568/309; 568/338; 568/700; 568/810; 568/814; 549/476; 560/60; 560/184; 562/401; 562/450; 564/385

[58] Field of Search .............................. 549/476; 560/60, 560/184; 562/401, 450; 564/385; 568/308, 309, 338, 700, 810, 814

[56] References Cited

PUBLICATIONS

Aoi et al., "Synthesis of Optically Active Cobalt(Salen) Type Complexes and their Asymmetric Reactivity toward Propylene Oxide", J. Organomet. Chem. 85:241–248 (1975).

Baldwin and Carter, "Complete Kinetic Analysis of the Thermal Stereomutations of (+)–(1S,2S,3R)–r–1–Cyano–t–2–Methyl–1,2,t–3–Trideuteriocyclopropane", J. Am. Chem. Soc. 104:1362–1368 (1982).

Ciucanu and Kerek, "A Simple and Rapid Method for the Permethylation of Carbohydrates", Carbohydrate Res. 131:209–217 (1984).

Hutchins et al., "Asymmetric Reduction of Phosphinyl Imines with Hydride Reagents. Enantioselective Synthesis of Chiral Primary Amines", J. Org. Chem. 52: 702–704 (1987).

Itsuno et al., "Asymmetric Synthesis Using Chirally Modified Borohydrides. Part 3. Enantioselective Reduction of Ketones and Oxime Ethers with Reagents Prepared from Borane and Chiral Amino Alcohols", J. Chem. Soc. Perkin Trans. 1:2039–2044 (1985).

Itsuno et al., "Catalytic Behavior of Optically Active Amino Alcohol–Borane Complex in the Enantioselective Reduction of Acetophenone Oxime O–Alkyl Ethers", Bull. Chem. Soc. Jap. 60:395 (1987).

Krzyzanowska and Stec, "A New Approach to the Synthesis of Primary Amines, Isothiocyanates, and 1–Aminoalkanephosphonates via N–Phosphinyl Aldoximes and Ketoximes", Int. J. Meth. Synth. Org. Chem. (Synthesis), p. 521 (Jul. 1978).

Krzyzanowska and Stec, "A Study of the Synthesis of Optically Pure Active Amines from Prochiral N–Phosphinylimines", Int. J. Meth. Synth. Org. Chem. (Synthesis), pp. 270–273 (Apr., 1982).

Kyba et al., "Host–Guest Complexation. I. Concept and Illustration", J. Am. Chem. Soc. 99:2564–2571 (1997).

Noyori et al., "Rational Designing of Efficient Chiral Reducing Agents. Highly Enantioselective Reduction of Aromatic Ketones by Binaphthol–Modified Lithium Aluminum Hydride Reagents", J. Am. Chem. Soc. 106:6709–6716 (1984).

Noyori et al., "Synthetic Applications of the Enantioselective Reduction by Binaphthol–Modified Lithium Aluminum Hydride Reagents", J. Am. Chem. Soc. 106: 6717–6725 (1984).

Seebach et al., "Reduction of Ketones with LiAlH$_4$ Complexes of $\alpha,\alpha,\alpha',\alpha'$–Tetraaryl–1,3–Dioxolane–4,5–Dimethanols (TADDOLs). A Combination of Enantioselective Reduction and Clathrate Formation with a Discussion of LAH Reagents Bearing C$_2$–Symmetrical Ligands", Croatica Chemica Acta 69:459–484 (1996).

Toda et al., "Optical Resolution of Bicyclo[2.2.1]heptanone, Bicyclo[2.2.2]octanone, and Bicyclo[3.2.1]octanone Derivatives by Inclusion Complexation with Optically Active Host Compounds", J. Org. Chem. 56:7332–7335 (1991).

Toda et al., "A Simple Preparative Method for Optically Active Glycidic Esters", Tetrahedron: Asymmetry 6:1059–1062 (1995).

Toda et al., "Optical Resolution of Methyl Phenyl and Benzyl Methyl Sulfoxides and Alkyl Phenylsulfinates by Complexation with Chiral Host Compounds Derived from Tartaric Acid", J. Chem. Soc., Chem. Commun., 639–640 (1995).

von dem Bussche–Hünnefeld et al., "32. $\alpha,\alpha,\alpha',\alpha'$–Tetraaryl–1,3–dioxolane–4,5–dimethanols (TADDOLs) for Resolutions of Alcohols and as Chiral Solvating Agents in NMR Spectroscopy", Helvetica Chimica Acta 75:438–441 (1992).

Wallbaum and Martens, "Asymmetric Syntheses with Chiral Oxazaborolidines", Tetrahedron:Asymmetry 3:1475–1504 (1992).

Weber and Wimmer, "Optical Resolution by Crystalline Inclusion Formation Using New Lactic Acid Derived Hosts", Chirality 5:315–319 (1993).

Weber et al., "New Crystalline Hosts Based on Tartaric Acid. Synthesis, Inclusion Properties, and X–ray Structural Characterization of Interaction Modes with Alcohol Guests", J. Org. Chem. 57:6825–6833 (1992).

*Primary Examiner*—Johann Richter
*Assistant Examiner*—Brian J. Davis
*Attorney, Agent, or Firm*—Pennie & Edmonds LLP

[57] ABSTRACT

The present invention relates to a tandem process of reduction and host-guest complexation using metal-hydride complexes to reduce chemical entities bearing carbonyl groups or their equivalents, and host-guest complexation to achieve improved optical resolution of the reduction product. In the complexation step, the reduction product is optically resolved via inclusion into the crystalline complex where it resides as guest and another complex component acts as host. Additional crystallization stages are performed if further improvements in the enantiomeric excess is desired.

17 Claims, No Drawings

TANDEM REDUCTION AND HOST-GUEST COMPLEXATION

FIELD OF THE INVENTION

The present invention relates to a tandem process of reduction and host-guest complexation using metal-hydride complexes to reduce chemical entities bearing carbonyl groups or their equivalents, and host-guest complexation to achieve improved optical resolution of the reduction product.

BACKGROUND OF THE INVENTION

In recent years there has been intensive investigations to further the cause of asymmetric reduction specifically as it relates to the development of new pharmaceutical intermediates and bulk drugs. This effort has been spurred by the benefits of single isomer or enantiopure compounds used as pharmaceutical drug agents. Factors such as availability and the overall economics and safety related to the use of new reagents has promoted the idea that an ideal chiral reducing agent could be fabricated from cost effective precursors with the chiral moiety being derived from readily available members of the chiral pool.

Among the techniques for introducing chirality that are available to the industrial chemist, the one that has proven especially useful is asymmetric reduction.

Reduction of unsymmetrical ketones to alcohols is among the most useful. This reaction is achieved by the overall addition of hydride ("H—") to one face of the carbonyl group leading preferentially to the formation of one enantiomer.

In 1992, von dem Bussche-Hunnefeld, Beck, Lengweiler, and Seebach published an article in Helvetica Chimica Acta, vol. 75, 438–441 regarding the use of so-called TADDOLs (see page 75 for the list of abbreviations) as chiral shift reagents in NMR spectroscopy. Although they discussed the formation of host-guest complexes between a few TADDOLs and alcohols, the focus of this article was on the utility of certain TADDOL compounds in NMR spectroscopy.

More recently, a paper by Seebach et al. in Croatica Chemica Acta, vol. 69, no. 2, 1996, pages 459–484, discussed a method that allows reduction of asymmetric ketones to secondary alcohols and then taking advantage of the guest-host complex formed between the metal hydride complex and the alcohol produced to achieve enantiomeric enrichment. The work described in that paper was based mainly on Noyori et al.'s results (J. Am. Chem. Soc. vol. 106, 1984, pages 6717–6725; J. Am. Chem. Soc. vol. 106, 1984, pages 6709–6716) which suggested that high enantiomeric selectivity was achievable only with aluminum complexes bearing an additional alkoxide ligand such that there is only one hydride bound to aluminum. Seebach et al. thus restricted their experiments to the use of alkoxide-bearing aluminum hydride complexes. Seebach et al. also did not investigate the influence on the chemical and optical yields of factors such as the nature of solvent (THF was the only solvent used), starting amounts of reactants, and relative amount of solvents in a system using a solvent-mixture to name a few.

There have also been many journal articles discussing the process of host-guest complexation, but they typically involved the investigation of a very narrow class of compounds under certain conditions to achieve substantial enantiomeric excess. A number of articles published by Cram and co-workers, for instance, discuss mainly the use of crown ethers in the formation of various host-guest complexes (see for example J. Am. Soc. 1997, 99, 2564–2571). In addition, the guest compounds they discuss are typically charged species such as salts of quaternary amines.

In the J. Org. Chem. 1991, 56, 7332–7335, Toda and Tanaka describe the optical resolution of bicyclic ketone derivatives bicyclo[2.2.1]heptanone, bicyclo[2.2.2]-octanone, and bicyclo[3.2.1]octanone using the host compounds (S,S)-(−)-1,6-bis(o-chloro-phenyl)-1,6-diphenyl-2,4-diyne-1,6-diol, (R,R)-(−)-trans-4,5-bis(hydroxydiphenyl)-2,2-dimethyl-1,3-dioxacyclopentane, and (S)-(−)-10,10'-dihydroxy-9,9'-biphenanthryl. Although this reference teaches a process of optical resolution via inclusion complexation, it is restricted to bicyclic ketone derivatives.

The preparation of optically active glycidic esters by inclusion complexation using the chiral host compound (R,R)-(−)-trans-4,5-bis-(hydroxydiphenylmethyl)-2,2-dimethyl-1,3-dioxacyclopentane and its derivatives was described by Toda, Takumi, and Tanaka in Tetrahedron: Asymmetry Vol. 6, No.5, 1059–1062. While the experiments they performed involved inclusion complexation, they were restricted to resolution of optically active glycidic esters. Toda and co-workers also discussed the results of experiments involving optical resolution using TADDOL type compounds in J. Chem. Soc., Chem. Commun., 1995, 639, but they confined their investigation to certain sulfoxides and sulfinates.

In J. Org. Chem. 1992, 57, 6825–833, Weber et al. discuss the optical resolution using host-guest complexation of several types of guest molecules ranging from alcohols to a few monocyclic systems. However, all of the molecules that Weber et al. used as guests are small molecules such as MeOH, EtOH, 2-PrOH, t-BuOH, and benzene which were also used as solvent at the same time. As Weber et al. states, "[t]he formation and stability of these crystalline inclusion complexes are affected by functional as well as by topological complementarity and consequently are sensitive to small structural variations." Thus, even though the process they discussed involved alcohols, they clearly suggest there is no guarantee the same process will also work for alcohols with structures larger and more complex than the ones they investigated.

It is important to note that none of the above references has undertaken a systematic investigation of the many factors that play a role in the success of asymmetric reduction process and host-guest complexation. A full understanding of the process of host-guest complexation alone has been hindered by the complexity of the molecular interactions between the host and guest that determine the probability of formation of a host-guest complex. There is also little or incomplete understanding regarding the influence of other factors—for instance, the nature of solvent, reaction temperature, molar ratio of the solvents in a solvent-mixture, and duration of the reaction—on the enantiomeric excess obtainable in an optical resolution procedure, and even whether factors such as the scale of the reaction can actually have an impact on the enantiomeric excess of a product resolved via inclusion crystallization. All of these contribute to the unpredictability of the outcome of reactions involving host-guest complexation. It is thus highly desirable to come up with a systematic investigation of various factors that come into play in host-guest complexation and also to examine in-depth the benefits that can be derived from coupling the process of host-guest complexation with another process such as asymmetric reduction.

SUMMARY OF THE INVENTION

The invention is a process of enantioselectively reducing carbonyl or carbonyl-bearing chemical entities with chiral hydride reducing agents (using inexpensive, readily available chiral auxiliaries in sodium or aluminum hydride reducing agents) followed by a second step comprising further optically resolving the reduction product through the formation of a complex comprising the reduction product and another chemical entity such as a ligand arising from the original metal-hydride complex. In the second process, the reduction product is further optically resolved by its inclusion into the crystalline complex where it resides as guest and another complex component acts as host. If further improvements in the enantiomeric excess is desired, the process may be extended to encompass two or more crystallization stages instead of just one following the reduction stage.

Each crystallization stage in the tandem reduction-host guest (term host-guest hereafter referred to as "HG") complexation process may be accomplished in a number of ways. For example, any one of the following three methods may be used to obtain the crystals in the complexation stage of the tandem reduction-HG complexation process: crystallization from a solution in a closed vessel, crystallization from a solution in an open vessel, or crystallization from a suspension. After the desired amount of crystals have been obtained in the crystallization stage, separation of the reduction product from the other chemical components of the crystals may be achieved by thermally breaking down the host-guest complex into its various chemical components by distillation, or by exploiting the differential solubility of the components of the complex in a particular solvent. The separation of the reduction product from the other chemical components of the host-guest complex may also be accomplished using other means well-known in the art.

By combining the method of enantioselective reduction of carbonyl-containing compounds or their equivalents with the process of host-guest complexation, further improvements on the enantiomeric excess of the alcohol produced in the reduction step (which by itself may be already enantioselective) can be attained—an improvement not possible with a one-step enantioselective reduction alone. Unexpectedly, this tandem method of reduction-HG complexation procedure offers another significant and surprising benefit: the particular enantiomer resolved by the tandem reduction-HG complexation process can, in some cases, be different from the enantiomer obtained when host-guest complexation alone was performed. Hence, the tandem reduction-HG complexation procedure can make possible the optical resolution of a particular enantiomer of a reduction product which would otherwise not be feasible either because the one-step process only resolves the other enantiomer or the one-step process fails to resolve either enantiomer. In addition, the present invention is useful in that not only it allows further improvements on the enantiomeric excess in cases where the one-step enantioselective reduction already leads to significant enantioselectivity and good yields, but the tandem reduction-HG complexation technique may also allow a decent or even significant enantiomeric excess in situations where a one-step enantioselective reduction fails to produce good enantioselectivity. Further, the present invention demonstrates that is possible to achieve both good yield and high enantiomeric excess using relatively mild experimental conditions, e.g., reaction temperatures that are much higher than the −100° C. reaction temperature cited in some references.

Another important result obtained from the present invention is that, in certain instances, the solvent plays an important role in determining the sucess of an optical resolution process such as the present invention. For example, in instances where little or no HG complex is obtained, a mere change of solvents may allow a dramatic reversal towards a successful optical resolution. In addition, the present invention shows that not only can the solvent mixture sometimes yield higher enantiomeric excess ("e.e.") than a one-solvent system, but the relative amounts of solvents can also affect the degree of optical resolution attained. In some instances, adjusting the relative amounts of reactants alone can have a significant impact on the degree of enantioselectivity that can be achieved. Furthermore, the present invention affords an additional advantage in that the whole tandem-HG complexation procedure may be undertaken as a one-pot process—a significant advantage in terms of convenience. Also unexpectedly, the present invention shows that, in some cases, merely changing the scale of the reaction can significantly improve the e.e. values obtained.

DETAILED DESCRIPTION OF THE INVENTION

The present invention is a tandem reduction-host-guest complexation process useful for obtaining an enantiomeric excess of a reduction product. It will be understood that in the reduction stage of the tandem reduction-HG complexation process, the reduction product of a chiral hydride complex and a carbonyl group will be an alcohol. Where the carbonyl equivalent is a thioketone, the reduction product will be mercaptan.

Where the carbonyl equivalent is an imine, the reduction product will be an amine. Where the carbonyl equivalent is an oxime or an oxime ether, the reduction product will be a species having an —NH—O— group. Where the carbonyl equivalent is an epoxide, the reduction product will be an alcohol. Where the carbonyl equivalent is a thioepoxide, the reduction product will be a mercaptan. Where the carbonyl equivalent is an enamine, the reduction product will be an amine.

As used herein, "enantioselectively reducing" means delivering an equivalent of hydride from a present chiral aluminum hydride complex preferentially to one face of a prochiral chemical entity, so as to obtain an enantiomeric excess of a particular reduction product thereof, or in the case where the prochiral chemical entity contains at least one chiral center, a diastereomeric excess of a particular reaction product thereof. By "carbonyl equivalent" is meant an organic moiety derived from a carbonyl group and capable of undergoing asymmetric reduction to yield an asymmetric reduction product. Such carbonyl equivalents include ketones, thioketones, imines (Schiff bases), unsymmetrical diaryl or dialkyloximes, unsymmetrical diaryl or dialkyloxime ethers, epoxides, thioepoxides, enamines, and the like. Such carbonyl equivalents are available commercially from, for example, Aldrich Chemical Co., Milwaukee, Wis., or obtainable from conventional organic synthesis via means known to those skilled in the art.

In addition, the present invention may involve the reduction of a carbon—carbon double bond of an $\alpha,\beta$-unsaturated carbonyl, or $\alpha,\beta$-unsaturated carbonyl equivalent system, via 1,4-addition of hydride to the $\beta$-carbon atom the $\alpha,\beta$-unsaturated carbonyl or $\alpha,\beta$-unsaturated carbonyl equivalent system. Such reductions are advantageously conducted at temperatures ranging from about −78° C. to room temperature, preferably from about −78° C. to about 0° C., and in inert organic solvents described above.

In the reduction stage of the tandem reduction-HG complexation procedure, a metal hydride complex is admixed with the substrate to be reduced. By "metal-hydride complex" is meant a complex produced from the reaction between a metal hydride and another chemical entity acting as the source of a chiral or achiral ligand such that the metal-hydride complex produced comprises at least one equivalent of hydride, at least one equivalent of a chiral ligand, a metal such as aluminum, and a cation selected from a group consisting of $Na^+$, $Li^+$, and $K^+$. By "substrate to be reduced" is meant a chemical entity having a carbonyl group or carbonyl equivalent. Such admixing can be accomplished preferably by adding the metal-hydride complex, preferably as a composition comprising the metal-hydride complex and organic solvent, to a substrate to be reduced, preferably as a solution in organic solvent. Alternatively, the substrate to be reduced, preferably as a solution in organic solvent, can be added to the metal-hydride complex, preferably as a composition comprising the chiral hydride complex and organic solvent. Preferably, an organic solution of the substrate to be reduced is added dropwise to a composition comprising the chiral hydride complex and organic solution. Most preferably, the reduction stage is performed by freshly preparing a composition comprising the metal-hydride complex and organic solvent, via methods described above, and thereafter adding to the complex an organic solution of the substrate to be reduced, such that the synthesis of the metal-hydride complex and reduction of the desired substrate are achieved in a one-pot method. Where permissible, it is most preferred that the steps of preparation of reducing agent, reduction of the substrate, and host-guest complexation are all conducted as a one-pot process.

As used herein, "inert organic solvent" means that the organic solvent lacks active hydrogens or other groups capable of reacting with the hydride species. Suitable organic solvents include, but are not limited to alkyl hydrocarbons, such as pentane, hexane and heptane; cyclic or acylic ethers, such as THF and diethyl ether; optionally substituted aromatics, such as benzene, toluene, xylene and chlorobenzene; polyethers such as diglyme and triglyme; other solvents that are inert to hydride reducing agents; and mixtures thereof Preferably, the organic solvent is THF, diglyme or mixtures thereof.

The present tandem reduction-HG complexation process encompasses the use of compositions which lack organic solvent. After admixing in the presence of an organic solvent the $MAlH_4$ (where M stands for a metal ion), chiral ligand (s), and optionally the achiral ligand, the compositions can be concentrated, preferably in vacuo, so as to obtain a solid, solvent-free chiral hydride complex. Such solvent-free chiral hydride complexes are preferably stored under an inert atmosphere, e.g., nitrogen or argon, in a dark, air tight vessel. When stored in this manner, the solvent-free chiral hydride complexes should be stable at room temperature for several months, and at low (<0° C.) temperatures for several years.

The chiral aluminum hydride complex compositions that can be used in the present invention optionally comprise other agents useful for imparting and/or fine-tuning enantioselectivity to carbonyl group and carbonyl equivalent-containing substrates. Such agents include chiral alkoxide bases; trialkylamines, such as triethylamine; and Lewis acids such as aluminum chloride, titanium tetrachloride, and the like, and can be added to the present compositions at any stage of the synthesis of the present chiral hydride complexes.

In the reduction stage of the tandem-HG complexation process, reduction of the desired substrate with the present chiral hydride complexes can occur at a temperature from −78° C. to the reflux temperature of the solvent used in the reaction mixture, preferably from −70° C. to room temperature. Reaction times may vary from several minutes to up to 7 days, depending upon the reaction temperature and nature of metal-hydride complex and substrate.

Because the chiral hydride complexes of the present invention are moisture sensitive, the reductions are preferentially conducted under an inert atmosphere such as nitrogen or argon. Once the metal-hydride complex is admixed with the substrate to be reduced, and reacted therewith such that the substrate to be reduced is reduced by the chiral hydride complex, the reaction is quenched, typically with water, aqueous acid, aqueous ammonium chloride, aqueous tartrate solution, or the like.

In addition, the reduction step in the present tandem reduction-HG complexation process can be achieved by using metal-hydride complexes in conjunction with other hydride reducing agents known to those skilled in the art, such that the present complexes are auxiliary reducing agents. In this instance, the present complexes are present in less than stoichiometric amounts, whereas the other hydride reducing agents are present in stoichiometric or excess quantities. In this instance, the present metal-hydride complexes are continuously regenerated via reaction with the other hydride reducing agent(s). Furthermore, the reduction step in the present tandem-HG complexation procedure can be performed in the presence of a catalyst.

In the host-guest ("HG") complexation stage of the tandem reduction-HG complexation process, a number of procedure can be used. In one preferred embodiment of the tandem process, the reduction stage is followed directly or indirectly by a crystallization stage in which the reduction mixture comprising the reduction product is allowed to stand inside a closed flask until the maximum or desired amount of crystals have precipitated. In another preferred embodiment of the crystallization stage of the tandem reduction-HG complexation process, the reduction stage is followed directly or indirectly by a crystallization stage in which the reaction mixture is allowed to stand in an open vessel to allow almost all of the solvent to gradually evaporate while the crystals form. In still another embodiment of the tandem process, the reduction stage is followed directly or indirectly by a crystallization stage in which the crystals are allowed to form from a suspension.

In the embodiments of the host-guest complexation stage described above, the crystals can form from the co-crystallization of the reduction product and the ligand arising from the original metal-hydride complex. Depending on the reaction conditions and starting materials used, the molar ratio of the reduction product to the ligand in the crystals may vary from 1:1 to 1:6 or higher (with respect to the ligand). Depending on the solvent system used, the crystals may comprise a ternary complex comprising the reduction product, ligand, and a solvent molecule. In some instances, the ligand forms a binary complex with a solvent, and during the crystallization stage, the reduction product displaces the solvent molecule from the ligand-solvent complex and forms a binary complex with the ligand. Depending on the reaction conditions and starting materials used, the crystallization stage of the tandem reduction-HG complexation can take place within a few minutes or several days up to five weeks.

Another embodiment of the tandem reduction-HG complexation process is one in which two crystallization steps follow the reduction stage. In this embodiment, after the reduction product is separated from the other components of the crystals obtained during the first crystallization stage, the reduction product is allowed to undergo a second crystallization stage with the same ligand. It may also be possible to perform a variation of this embodiment where the ligand used in the first crystallization stage is different from the ligand used in the second crystallization stage.

In a preferred embodiment of the tandem reduction-HG complexation procedure involving two crystallization stages, the solvent system used in the entire reduction-crystallization process is the same for each stage of the whole tandem process. In still another embodiment of the tandem reduction-HG complexation process involving two crystallization stages, the solvent system is different for each stage of the entire tandem process. Although the solvent system in the tandem reduction-HG complexation process may comprise only one type of solvent, a combination of at least two types of solvent may comprise the solvent system.

In the present tandem reduction-HG complexation process, it is possible in some instances to obtain a particular isomer (R or S) of the reduction product after the crystallization stage by adjusting the initial ratio of the R-isomer to S-isomer of the substrate to be reduced before the reduction step. In addition, another unexpected result in the present tandem reduction-host-guest complexation process is that the isomer of the reduction product obtained after the crystallization stage can be different from the isomer of the product obtained when a non-tandem one-step direct crystallization stage is performed, that is, when the crystallization stage is not preceded by a reduction step. A tandem reduction-HG complexation may thus allow the resolution of a particular isomer of a compound even in instances where a non-tandem process is not feasible either because the direct one-step crystallization procedure only obtains the opposite isomer or no isomer is resolved at all.

In one embodiment of the tandem reduction-HG complexation process, separation of the reduction product from the other chemical components of the crystals is achieved by heating the crystal comprising a binary or ternary complex to a temperature high enough to achieve efficient separation but low enough to prevent decomposition of the reduction product. As an illustration, the separation may be achieved using a distillation apparatus. Preferably, separation is performed under an inert gas environment such as nitrogen or argon. In another embodiment of the tandem reduction-HG complexation process, separation of the reduction product from the other chemical components of the crystals is performed by exploiting the different solubilities of various compounds in a given solvent. For example, after obtaining the maximum amount of crystals in the crystallization step, one may use a solvent that preferentially dissolve the reduction product included into the crystal together with the ligands and solvent molecules. If necessary, one may resort to heating the crystals and solvent to a temperature that would allow maximum separation. Combination of separation techniques such as those described above may be performed, or one may also perform any other techniques well-known in the art.

The chiral aluminum hydride complexes of the present invention are represented by the general formulas:

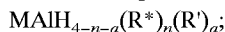

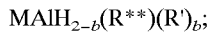

MAlH(R***); and

MAlH(R*)(R"), wherein:

M is Na$^+$, Li$^+$ or K$^+$;

n is 1–3;

a is 0–2; and b is 0–1, with the proviso that n+a≦3, and with the further proviso that when R** is S-BINOL, M is not Li$^+$.

These complexes are generally obtained by admixing 1 equivalent of MAlH$_4$ with R*, R or R*; optionally with 1–2 equivalents of an achiral ligand (R'); or optionally 1 equivalent of R". The chiral aluminum hydride complexes of the present invention can be obtained from 1 equivalent of MAlH$_4$ and 1 to 3 equivalents of a monodentate chiral ligand (R*) or a mixture of different R*s, 1 equivalent of monodentate chiral ligand (R*) and 1 equivalent of bidentate achiral ligand (R"), 1 eq. of a bidentate chiral ligand (R) or 1 eq. of a tridentate chiral ligand (R*). By "monodentate," "bidentate," and "tridentate" is meant a ligand having 1, 2 or 3 active hydrogen moieties, respectively.

It will be understood that when the chiral hydride complexes are obtained from MAlH$_4$, 1 equivalent of MBH$_4$ or MAlH$_4$ can be admixed in the presence of an organic solvent with 1–3 equivalents of R* and optionally with 1–2 equivalents of R', such that the total equivalents of R* and R' relative to MAlH$_4$ does not exceed three; with 1 equivalent of R* and 1 equivalent of R'; with 1 equivalent of R, and optionally with 1 equivalent of R'; or with 1 equivalent of R*.

MAlH$_4$ can be obtained commercially; e.g., LiAlH$_4$ is available from Aldrich Chemical Co., Milwaukee, Wis., and NaAlH$_4$ is available from Albemarle Corporation, Baton Rouge, La. Alternatively, MAlH$_4$ can be prepared by synthetic methods known to those skilled in the art.

Useful monodentate, bidentate, and tridentate chiral ligands are those that are derived from optionally protected carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof, and are capable of forming chiral hydride complexes with MAlH$_4$ such that the resulting chiral hydride complex is capable of enantioselectively reducing a carbonyl group or a carbonyl equivalent of a chemical entity. By "protected" is meant that the carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof, comprise protecting groups including, but not limited to, ketals, trimethylsilyl ethers, tetrahydropyranyl ethers, triphenylmethyl ethers, benzyl ethers, etc. Examples of such protecting groups, as well as methods for their use and removal, are found in T. W. Greene, *Protective Groups in Organic Synthesis*, John Wiley & Sons, New York, 1981. Such chiral ligands have one or more chiral centers and are optically active. The chiral ligands have 1–3 active hydrogen atoms per ligand that can react with one or more hydride groups MAlH$_4$, so as to form a sodium, lithium or potassium aluminum hydride:chiral ligand complex, with the release of H$_2$.

Useful chiral ligands include naturally occurring carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof; or synthetic analogs obtained using organic synthesis methods which are known to those skilled in the art.

Preferable chiral ligands are of the so-called TADDOL-type ligands where TADDOL stands for α,α,α',α'-tetraaryl-1,3-dioxolane-4,5-dimethanols. These TADDOLs react with metal hydrides such as $NaAlH_4$ or $LiAlH_4$ to form sodium aluminum dihydride complexes such as Na-TADDAL-$H_2$ (sodium aluminum dihyride complexes derived from TADDOLs).

Preferable chiral ligands include: (R,R)-(−)-trans-(α',α',(2,2-dimethyl-1,3-dioxolane-4,5-diyl)-bis-(diphenylmethanol) ("(−)-DDM"); (S,S)-(+)-trans-(α',α',(2,2-dimethyl-1,3-dioxolane-4,5-diyl)-bis-(diphenylmethanol) ("(+)-DDM"); (−)-2,3-O-cyclohexylidene-1,1,4,4-tetra-phenyl-L-threitol ("(−)-CYTOL"); (−)-2,3-O-cyclopentylidene-1,1,4,4-tetra-phenyl-L-threitol ("(−)-CPT"); (−)-2,3-O-(9-fluorenylidene)-1,1,4,4-tetra-phenyl-L-threitol ("(−)-FLUTOL"); (−)-2,3-O-isopropylidene-1,1-4,4-tetra-(4-methoxyphenyl)-L-threitol ("(−)-ITM"); (S)-(−)-1,1-Diphenyl-1,2-propanediol ("(−)-DPPD"); (R)-(+)-1,1,2-Triphenyl-1,2-ethanediol ("(+)-TPED"); 2,2'-Bis(diphenylphosphino)-1,1'-binaphthyl ("BINAP"); acetophenone acetylhydrazone ("APAH"); Z-N-acetyl-a-aminocinnamic acid ("ACA"); N-acetylphenylalanine ("APA"); 4,4-dimethyl-2,3(5H)-furandione ("DMFD"); acetophenone N-(diphenylphosphinyl)imine ("ADPI"); pantolactone (2-hydroxy-3,3-dimethyl-y-butyrolactone) ("PL"); and (−)-2,3-O-(3-pentylidene)-1,1,4,4,-tetra-phenyl-L-threitol. The abbreviations of these ligands will be used to facilitate reading of this specification.

Especially preferred are those R chiral ligands having a $C_2$ axis of symmetry. By "$C_2$ axis of symmetry" is meant a molecule having a $C_2$ axis as the sole element of symmetry, and therefore not possessing reflection symmetry (no sigma plane). The R chiral ligands can also be described as "axially disymmetric."

Where the chiral aluminum complexes of the present invention comprise R* but not R or R*, such complexes can comprise a mixture of up to three different R* ligands, as long as there is at least one hydride per equivalent of chiral complex available for imparting enantioselectivity to carbonyl group and carbonyl equivalent-containing substrates; or can comprise one R* ligand and one R'' ligand. Where the chiral aluminum complexes of the present invention comprise R**, such complexes can additionally comprise R*, as long as there is at least one hydride per equivalent of chiral complex available for imparting enantioselectivity to carbonyl group and carbonyl equivalent-containing substrates.

The R' achiral ligands have 1 active hydrogen atom per ligand and can react with one or more hydride groups of $MAlH_4$, preferably with one or more hydride groups of a sodium, lithium or potassium aluminum hydride:chiral ligand complex, so as to form a sodium, lithium or potassium aluminum hydride:chiral ligand:achiral ligand complex with the release of $H_2$. It is important that if the present chiral hydride complexes comprise R', there must be at least one hydride per equivalent of chiral complex available for imparting enantioselectivity to carbonyl group and carbonyl equivalent-containing substrates. In other words, if the present chiral hydride complexes comprise R', the total equivalents of R* or R**, and R', relative to $MAlH_4$, cannot exceed three.

Because R''comprises two active hydrogen moieties, it is preferable that when R'' is used as an achiral ligand, it is used in conjunction with R*. The R' and R'' achiral ligands can be used to optimize the yield of the product of reduction of the carbonyl group- or carbonyl equivalent-bearing chemical entity with the chiral hydride complexes of the present invention, or to optimize the enantiomeric excess of a desired enantiomeric product.

The present chiral aluminum hydride complexes are synthesized such that the $MAlH_4$; chiral ligand (R*, R or R*) and optionally the achiral ligands (R' or R'') are admixed in the presence of an organic solvent lacking active hydrogens or other groups capable of reacting with hydride groups. Suitable organic solvents include, but are not limited to alkyl hydrocarbons, such as pentane, hexane and heptane; cyclic or acylic ethers, such as THF and diethyl ether; optionally substituted aromatics, such as benzene, toluene, xylene and chlorobenzene; polyethers such as diglyme and triglyme; other solvents that are inert to hydride reducing agents; and mixtures thereof. Preferably, the organic solvent is THF, diglyme or mixtures thereof. The solution of the organic solvent and the chiral hydride complex thus obtained can be used directly as a composition for enantioselectively reducing a chemical entity having a carbonyl group or a carbonyl equivalent, or can be concentrated, optionally in vacuo, to afford a chiral hydride complex free from solvent. In the latter case, the chiral hydride complex can be stored, preferably under an inert atmosphere, for future use.

In one embodiment of the invention, the chiral hydride complexes are prepared by admixing in the presence of organic solvent 1 equivalent of $MAlH_4$ with 3 equivalents of R*.

In another embodiment of the invention, the chiral hydride complexes are prepared by admixing in the presence of organic solvent 1 equivalent of $MAlH_4$ with 2 equivalents of R*; and 1 equivalent of R'.

In another embodiment of the invention, the chiral hydride complexes are prepared by admixing in the presence of organic solvent 1 equivalent of $MAlH_4$ with 1 equivalent of R*; and 2 equivalents of R'.

In another embodiment of the invention, the chiral hydride complexes are prepared by admixing in the presence of organic solvent 1 equivalent of $MAlH_4$ with 1 equivalent of R*; and 1 equivalent of R''.

In another embodiment of the invention, the chiral hydride complexes are prepared by admixing in the presence of organic solvent 1 equivalent of $MAlH_4$ with 1 equivalent of R**; and 1 equivalent of R'.

In another embodiment of the invention, the chiral hydride complexes are prepared by admixing in the presence of organic solvent 1 equivalent of $MAlH_4$ with 1 equivalent of R***.

In another embodiment of the invention, the chiral hydride complexes are prepared by admixing in the presence of organic solvent 1 equivalent of MAlH4 with 2 equivalents of R*.

In another embodiment of the invention, the chiral hydride complexes are prepared by admixing in the presence of organic solvent 1 equivalent of $MAlH_4$ with 1 equivalent of R**.

In another embodiment of the invention, the chiral hydride complexes are prepared by admixing in the presence of organic solvent 1 equivalent of $MAlH_4$ with 1 equivalent of R*.

The chiral hydride complexes can be prepared by adding the $MAlH_4$, preferably as a solution in organic solvent, to the chiral ligand(s), preferably as a solution in organic solvent, or to a mixture of chiral and achiral ligands, preferably as a solution in organic solvent. Alternatively, the chiral ligand (s), preferably as a solution in organic solvent, can be added to the $MAlH_4$, preferably as a solution in organic solvent, optionally followed by addition of an achiral ligand, preferably as a solution in organic solvent. Preferably, an organic solution of the chiral ligand(s) is added to an organic solution of $MAlH_4$, optionally followed by the addition of an organic solution of an achiral ligand (R' or R''). Most preferably, the organic solvent is THF, diglyme or mixtures thereof. Because the chiral aluminum hydride complexes of the present invention are moisture sensitive, the chiral hydride complexes are preferably prepared under an inert atmosphere such as nitrogen or argon.

The compositions in the present invention useful for enantioselectively reducing a chemical entity having a carbonyl group or a carbonyl equivalent comprise 1 equivalent of sodium cation (Na$^+$), lithium cation (Li$^+$) or potassium cation (K+); 1 equivalent of aluminum cation (Al$^{3+}$); 1–3 equivalents of hydride; 1–3 equivalents of a monodentate ligand (R'), 1 equivalent of a bidentate ligand (R) or tridentate ligand (R*); optionally 1–2 equivalents of a monodentate achiral ligand (R') or 1 equivalent of a bidentate achiral ligand (R"), wherein R*, R, R* and R' are defined above; and preferably an inert organic solvent. It is to be understood that the compositions that comprise 1 equivalent of R* can comprise 1–2 equivalents of R', or 1 equivalent of R". The compositions that comprise R** can comprise 1 equivalent of R'.

Some of the metal-hydride complexes that are useful in the present invention can have the following compositions:

1 equivalent of sodium cation (Na$^+$), lithium cation (Li$^+$) or potassium cation (K$^+$); 1 equivalent of aluminum cation (Al$^{3+}$); 1 equivalent of hydride; and 3 equivalents of R*.

1 equivalent of sodium cation (Na$^+$), lithium cation (Li$^+$) or potassium cation (K$^+$); 1 equivalent of aluminum cation (Al$^{3+}$); 1 equivalent of hydride; 2 equivalents of R*; and 1 equivalent of R'.

1 equivalent of sodium cation (Na$^+$), lithium cation (Li$^+$) or potassium cation (K$^+$); 1 equivalent of aluminum cation (Al$^{3+}$); 1 equivalent of hydride; 1 equivalent of R*; and 2 equivalents of R'.

1 equivalent of sodium cation (Na$^+$), lithium cation (Li$^+$) or potassium cation (K$^+$); 1 equivalent of aluminum cation (Al$^{3+}$); 1 equivalent of hydride; 1 equivalent of R*; and 1 equivalent of R".

1 equivalent of sodium cation (Na$^+$), lithium cation (Li$^+$) or potassium cation (K$^+$); 1 equivalent of aluminum cation (Al$^{3+}$); 1 equivalent of hydride; 1 equivalent of R**; and 1 equivalent of R'.

1 equivalent of sodium cation (Na$^+$), lithium cation (Li$^+$) or potassium cation (K$^+$); 1 equivalent of aluminum cation (Al$^{3+}$); 1 equivalent of hydride; and 1 equivalent of R***.

1 equivalent of sodium cation (Na$^+$), lithium cation (Li$^+$) or potassium cation (K$^+$); 1 equivalent of aluminum cation (Al$^{3+}$); 2 equivalents of hydride; and 2 equivalents of R*.

1 equivalent of sodium cation (Na$^+$), lithium cation (Li$^+$) or potassium cation (K$^+$); 1 equivalent of aluminum cation (Al$^{3+}$); 2 equivalents of hydride; and 1 equivalent of R**.

1 equivalent of sodium cation (Na$^+$), lithium cation (Li$^+$) or potassium cation (K$^+$); 1 equivalent of aluminum cation (Al$^{3+}$); 3 equivalents of hydride; and 1 equivalent of R*.

The present invention may also involve the use of compositions which comprise Na$^+$, Li$^+$ or K$^+$; Al$^{3+}$; hydride; R*, R or R*; and optionally R' in stoichiometries outside of the ranges described above. Such compositions comprise chiral hydride complexes having oligomeric structure.

EXAMPLES

The following series of Examples are presented by way of illustration and not by way of limitation on the scope of the invention.

HPLC Method

The following procedure illustrates the use of HPLC method in the present invention. Enantiomerically enriched mixtures of PET obtained from the reduction of AP with the chiral hydride complexes of the present invention were converted to their carbamate derivatives using (S)-α-(1-naphthyl)ethylisocyanate and Et$_3$N so as to provide a more easily separable mixture of (S,R)- and (S,S)-diastereomers. The diastereomeric mixtures were separated on a Laboratornj Pristoje Praha HPLC with a HPP 5001 high pressure pump, LCO-2563 UV-VIS detector (λ=254 nm), CI-1002 computing integrator and TZ 4620 line recorder. A 150×3.3 mm column was used with Separon-NH$_2$ (aminopropylated silica, 5μ) sorbent. The eluent was 0.5:99.5 iPrOH:n-hexane, passed at a rate of 0.6 mL/min. Capacity factors (K') for each component were calculated using the equation K'=(τ–τ$_0$)/τ$_0$, where τ is a retention time, τ$_0$ is that for toluene (1.64 min. under the conditions employed). The retention times (τ) and capacity factor (K') values for diastereomeric adducts were as follows: (S,R): τ=14.4 min., K'=7.78; (S,S): τ=17.5 min., K'=9.65.

GC Method

GC analysis was performed using a Biochrome-J instrument with a quartz capillary column (30 m×0.2 mm) containing dipentylated and trifluoroacetylated γ-cyclodextrin (Carbohydrate Res., 131, 209–217 (1984)), film thickness= 0.2 mm. V$_{He}$=1 mL/min.; initial column temperature=50° C., raising temperature (8° C./min.2 within 10 min. after probe injection. GC analysis of trifluoroacetylated derivatives of (R)- and (S)-PET (Zh. Analyt. Khim., 1973, 18(7), 41427) gave completely resolved peaks, with the retention time of the (R)-derivative being longer than that of the (S)-derivative.

It is found that complexes that are most efficient in terms of yield and e.e., possess a C$_2$ axis of symmetry. Axially disymmetric molecules such as these are thought to be less susceptible to disproportionation reactions and hence provide complexes with a higher degree of enantioselectivity.

It is to be understood that for a particular chiral hydride complex, the chiral ligand thereof will produce an enantiomeric excess of a reduction product such that for that particular hydride complex, the use of the same chiral ligand but of the opposite enantiomer will give rise to the reduction product of the opposite stereochemistry. For example, whereas NaAlH$_2$((+)-DDM) reduces acetophenone to (R)-1-phenylethan-1-ol in 91% enantiomeric excess (0° C.; 48 h; diglyme), reduction of acetophenone with NaAlH$_2$((–)-DDM) under identical conditions will give an enantiomeric excess of (S)-1-phenylethan-1-ol. In the tables below, the inclusion of the acronym GC in a box means that the experimental parameter indicated in the same box was measured using gas chromatography.

A number of references have been cited and the disclosures of which are incorporated herein by reference.

Example 1

Preparation of (S)-4-Isopropyl-5,5-diphenyloxazoborolidine (IDOB)

To the knowledge of the inventor, the literature cites the use of chiral oxazoborolidines (OAB), more precisely (S)-IDOB, only in the asymmetric hydride reduction of a prochiral substrate. In particular, the article in Bull. Chem. Soc. Jap., 1987 60, 395 reports the stoichiometric reduction of o-methylacetophenone oxime using 1:1 LiAlH$_4$/(S)-IDOB system with 85% chemical and 76% optical yields of the final product (S)-PEA. It is of considerable interest to use this compound as a catalyst for hydride reduction of imine derivatives using achiral hydroaluminates such as Vitride®. (S)-IDOB was synthesized by mixing (S)-2-Amino-3-methyl-1,1-diphenylbutanol (AMDB, see Example 3) and a solution of BH$_3$-THF complex in THF. The BH$_3$-THF complex was obtained using a known procedure in which BF$_3$-Et$_2$O was added to a suspension of NaBH$_4$ in Et$_2$O with absorption of BH$_3$ gas by cold THF. The catalytic activity of (S)-IDOB was subsequently verified.

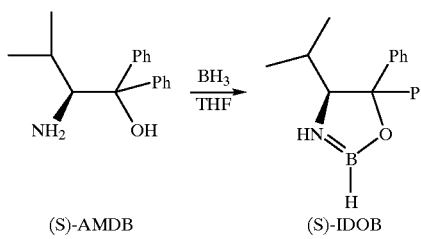

Example 2

Preparation of (S)-IDOB (based on a procedure described in JACS 1987, 109, 5551)

A 2M solution of BH$_3$ in THF (2 ml, 4 mmol) was added dropwise with stirring at room temperature to (S)-AMDB (280 mg, 1 mmol) dissolved in 10 ml THF. The resulting mixture was then allowed to stand at room temperature overnight. Evaporation of the solvent and excess BH$_3$ in vacuo at 20–50° C. gave a solid glass-resembling soap (crude IDOP). Its $^{11}$B NMR spectrum (in CDCl$_3$) showed a single broad peak at 28.6 ppm (with respect to BF$_3$-Et$_2$O standard) (literature: 28.1 ppm, see the reference above). The crude IDOB was used as catalyst designated OAB catalyst-1 in the reduction of AP with BH$_3$. The crude IDOB was further purified by sublimation at 100–120° C. in vacuo (0.5–1 torr). Only ca. ⅓ of the initial solid was sublimated (later used as a catalyst designated OAB catalyst-2); further heating of the remaining crude IDOB gave no additional sublimate. The $^1$H-NMR spectrum of the sublimated product contained all signals previously reported for IDOB. The colorless residue was apparently polymeric in nature and was later used as a catalyst (designated OAB catalyst-3) in the reduction of AP. The NMR spectra of this polymeric residue were considerably different from those of IDOB.

Example 3

Preparation of (S)-2-Amino-3-methyl-1,1-diphenylbutanol (AMDB)

The title compound is known to be an effective chiral ligand for asymmetric catalytic reduction of carbonyl compounds with BH$_3$ (Tetrahedron: Asymmetry, 1992, 3, 112, 1475). This aminoalcohol was used to obtain the corresponding oxazoborolidine which was later used as catalyst in the asymmetric hydride reduction of appropriate substrates using achiral hydroaluminates. AMDB was prepared based on the procedure described in the J. Chem. Soc. Perk. Trans. 1, 1985, 2039.

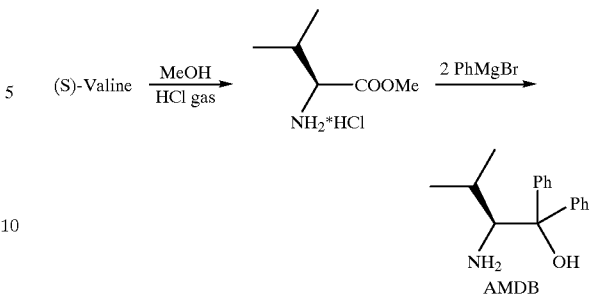

Stage 1. Esterification of (S)-Valine.

HCl gas was bubbled through a solution of (S)-valine (20 g, 0.17 mol, chemical and enantiomeric purity >98%) in 300 ml of MeOH (<1% water content) at reflux temperature for 3 hours, and then the reaction mixture was left overnight at room temperature. After removing the MeOH, the crude crystalline product obtained was dried by azeotrope distilling with benzene and then washed with ether. Crystallization of the residue gave 27.5 g (96%) of the pure (S)-valine methyl ester hydrochloride: m.p. 167.5–168° C. (literature: m.p. 171–173° C.). NMR-$^1$H (δ, ppm) in CDCl$_3$: 1.05–1.2 d/d (6H, 2.35–2.55 m (1H, CHMe$_2$), 3.75 s (3H, OCH$_3$), 3.95 s, broad (1H, CHN), 8.7–8.9 s broad (NH$_3^+$).

Stage 2. Preparation of AMDB

A solution of phenyl bromide (75.4 g, 0.48 mol) in 50 ml THF was added dropwise (with stirring) to a mixture of Mg (14 g, 0.48 mol) and THF (100 ml) after which the reaction mixture was allowed to stand at room temperature overnight. Because the reaction is exothermic, the reflux temperature was maintained.

To the solution of Grignard reagent thus obtained was added (S)-valine methyl ester hydrochloride (10 g, 0.06 mol) using ice water to cool the whole solution. The mixture was then stirred, first for 8 hours at room temperature, then for 2 hours at 50–60° C. Treatment of the mixture with 2N HCl followed by aqueous ammonia gave two layers. The organic layer was separated, the aqueous layer extracted with ethyl acetate, and the resulting aqueous extract and washings combined and dried with MgSO$_4$. The oily residue obtained after evaporating off the solvent was crystallized from ether-ethyl acetate. The crystalline product obtained was then dissolved in THF-ether, washed with 2N KOH and water, and evaporated. The solid residue was recrystallized from EtOH-H$_2$O (10:1) affording white crystals of pure aminoalcohol (6.6 g, 43%): m.p. (95.5–96° C.) NMR-$^1$H (δ, ppm) in CDCl$_3$: 0.9 d/d (6H, 2CH$_3$), 1.25 s (2H, NH$_2$), 1.78 sept (1H, CHMe$_2$), 3.85 s (1H CHN), 7.1–7.7 m (1OH, aromatic).

Example 4

Preparation of (1R,2R)-N,N'-bis(benzaldimino) cyclohexane (BBIC)

Synthesis of BBIC was performed based on a procedure described in the J. Am. Chem. Soc., 1982, 104, 1362.

2 PhCHO + 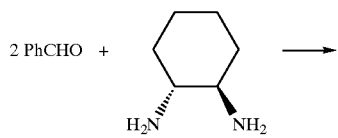 →

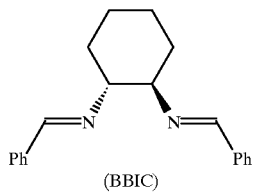

(BBIC)

A solution of PhCHO (2.1 ml, 21 mmol) in 20 ml benzene was added to (IR,2R)-diaminocyclohexane (1.1 g, 10 mmol, 97% purity) which was dissolved in 30 ml benzene. The mixture was heated at reflux for 3 hours using a Dean-Stark trap for collecting water. The mixture was subsequently evaporated leaving a yellow crystalline precipitate which was washed carefully with hexane several times. Drying the solid gave 1.56 g (47%) of pure BBIC as indicated by the NMR spectrum. NMR-$^1$H (~, ppm) in CDCl$_3$: 1.45–1.70 m (2H, cyclohexane ring), 1.8–2.05 m (6H, cyclohexane ring), 3.5 (2H, 2CH—N=), 7.3–7.45 m (6H, C$_6$H$_5$), 7.6–7.75 m (4H, C$_6$H$_5$), 8.25 (2H, 2PhCH=N—); m.p. 96–98° C.; $[\alpha]_D^{20}$=−174° (c 1, CHCl$_3$).

Example 5

Preparation of (1R,2R)-N,N'-bis((salicylaldimino)cyclohexane (BSIC)

A solution of salicyl aldehyde (5.5 ml, 52 mmol, >97%) in 30 ml benzene was added to (1R,2R)-diaminocyclohexane dissolved in 60 ml benzene. The mixture was heated at reflux for 2.5 hours using a Dean-Stark trap for collecting water. Evaporation of the solvent produced an orange oil which was extracted at reflux using hexane (30×40 ml). After cooling the extract, 5 g of a yellow crystalline precipitate was obtained. An additional 1.8 g of the product was isolated from the mother liquid. The total yield was 6.8 g (40%) with a melting point of 75° C. NMR-$^1$H (δ, ppm) in CDCl$_3$: 1.3–2.3 m (8H, 4CH$_2$ in cyclohexane ring), 3.2–3.6 m (2H, 2CH—N=), 6.7–7.1 m (4H, aromatic ring), 7.1–7.6 (4H, aromatic ring), 8.3 s (2CH=N—), 13.35 (2H, 2OH).

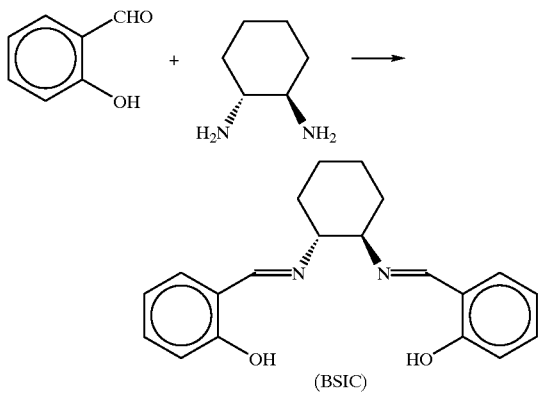

(BSIC)

Example 6

Preparation of Acetophenone N-(diphenylphosphinyl)imine (ADPI)

To extend the range of starting compounds that can be used in the reaction with the chiral reducing agents synthe-sized in the present invention, a new substrate for asymmetric hydride reduction, acetophenone N-(diphenylphosphinyl)imine (ADPI), was prepared. This substrate, as well as its structural analogs, was shown to react with Nayori's reagent BINAL-H over the temperature range −70→20° C. to give the corresponding amine having an e.e. of 80–100%. (J. Org. Chem. 1987, 52, 702). In addition, N-diphenylphosphinyl imines were reported as being very active substrates in cobalt-catalyzed asymmetric hydride reduction. Subsequent removal of the Ph$_2$P(O)-group can be carried out under mild conditions (HCl/MeOH, 25° C., 3 hours; V.Mikaiyama, Chem. Lett. 1997, 4931). Synthesis of ADPI was performed according to a procedure described in Synthesis, 1978, 521 and Synthesis, 1982, 270.

A solution of AP (6.75 g, 50 mmol) and Et$_3$N (7 ml, 50 mmol) in 150 ml 1:1 CH$_2$Cl$_2$-hexane was cooled between −35 and −40° C., and Ph$_2$PCl (11 g, 50 mmol), which was dissolved in 15 ml CH$_2$Cl$_2$, was added dropwise with stirring while maintaining the same temperature. After stirring for 3 hours, NEt$_3$·HCl precipitated and the mixture was allowed to warm up to room temperature. The mixture was filtered and the orange filtrate allowed to evaporate. The brown oil residue that remained was dissolved in 30 ml benzene, adding hexane until the oil separated. The first portion of the oil was removed while the rest was evaporated to produce an orange oil. This orange oil was then extracted using ether. Upon gradual evaporation of the ether extract over a period of 24 hours, a crystalline product was obtained. The crystals were filtered off, washed with cold benzene, and recrystallized from

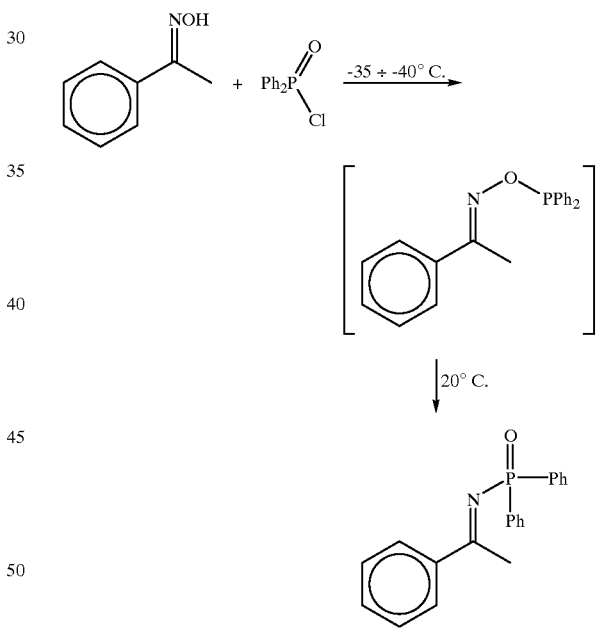

5:1 benzene-hexane. A pure product weighing 1.54 g (10% yield) was obtained with a melting point of 135–137° C. (literature m.p. 135–137° C.; Synthesis, 1982, 270). NMR-$^{31}$P(δ) in CDCl$_3$: a single signal was detected at 17.31 ppm. NMR-$^1$H (δ, ppm) in CDCl$_3$: 2.98 (3H, CH$_3$), 7.3–7.6 m (10H, arom), 7.9–8.15 m (5H, arom). NMR-$^{13}$C (δ, ppm) in CDCl$_3$: 22.975, 23.141 (CH$_3$, two signals due to splitting on $^{31}$P), 15 signals in the range of 127.93–181.57 (arom.).

Example 7

Preparation of (S)- and (R)-enantiomers of N-DPP-PEA

Ph$_2$P(O)Cl (0.235 g, 1 mmol), prepared as described in Example 15, was added at room temperature to a solution of (S)-PEA (0.133 g, 1 mmol) and 1 ml Et₃N in 5 ml dry dioxane. The mixture was heated at reflux for 10 minutes, cooled to room temperature, and treated with 50 ml 1% HCl. The crystals that precipitated were filtered off, washed with hot water, and dried to give 0.25 g (78% yield) of (S)-N-DPP-PEA having a melting point of 185–186° C. NMR-¹H (δ, ppm) in /CDCl₃: 1.6 d (3H, CH₃), 3.8 br. Q (1H, NH), 4.6 m (1H, CHN), 7.5–7.8 m (11 H, aromatic), 8–8.25 (4H, aromatic).

(R)-N-DPP-PEA was prepared in a manner similar to that described above. Melting point and spectral characteristics of the product were the same as those obtained for the (S)-enantiomer.

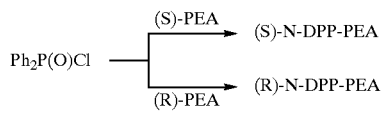

Example 8

Esterification of D-tartaric Acid

A mixture of D-tartaric acid (102 g, 068 mol), MeOH (81 ml, 2 mol), CH₂Cl₂ (200 ml), and conc. H₂SO₄ (2 ml) was heated at 60–70° C. for about 10 hours. The mixture was diluted with 100 ml H₂O, neutralized with solid NaHCO₃ to pH 7, and evaporated to half of its volume. The remaining portion was extracted with CHCl₃ followed by evaporation of the extract to give 41 g of a yellow oil. The aqueous layer was evaporated to dryness and extracted with CHCl₃ (3×100 ml). After removal of the solvent, an additional 38 g of oil was isolated. Distillation of the combined oil extracts gave 66 g (56%) of pure dimethyl D-tartrate as indicated by NMR.

Example 9

Acetalization of Cyclopentanone

Cyclopentanone (25 g, 0.3 mol) was added at room temperature to a solution of trimethyl ortoformate (33 ml, 0.3 mol) in 60 ml anhydrous MeOH containing 75 mg TsOH. The resulting mixture was allowed to stand at room temperature for 2 hours. After adding MeONa to pH 8–8.5 and removing the MeOH, the remaining portion was distilled in vacuo to give 23.2 g (60%) of pure cyclopentanone dimethyl acetal having a boiling point of 42° C. (8 torr). NMR-¹H (δ, ppm) in CDCl₃: 1.43–1.72 m (8H, 4CH₂); 3.08 s (6H, 2 OCH₃). NMR-¹³C (6 ppm) in CDCl₃: 22.89 (2CH₂), 33.82 (2CH₂), 48.76 (2CH₃O), 111.81 (O—C—O).

Example 10

Protection of Hydroxyl Groups of Dimethyl D-tartrate

A solution of dimethyl D-tartrate (32.5 g, 183 mmol), cyclopentanone dimethyl acetal (23.3 g, 180 mmol) and TsOH (1.1 g) in anhydrous benzene (450 ml) was heated at reflux temperature, the low-boiling components being distilled off until the vapor temperature reached 79.5° C. The remaining solution was diluted with 50 ml ether, washed with NaHCO₃-saturated water (2×40 ml) followed by washing with plain water, and then dried with MgSO₄. The brown oil obtained after removal of the solvent was distilled in vacuo to afford 28.5 g (65%) of dimethyl 2,3-O-cyclopentylidene-D-tartrate (95% purity, NMR) having a boiling point of 120–125° C. (1–2 torr). NMR-¹H (δ, ppm) in CDCl₃: 1.5–1.9 m (8H, 4CH₂), 3.65 s (6H. 2CH₃O), 4.6 s (2H. 2CHO).

Example 11

Preparation of (–)CPT

A solution of Grignard reagent was obtained using 28 g (1.14 mol) of Mg, 165 g (1.05 mol) of PhBr and 100 ml of THF. PhBr was added to Mg at room temperature and the solution allowed to stand for two hours after which the solution was heated at reflux temperature for 5 hours. A solution of dimethyl 2,3-O-cyclopentilidene-D-tartrate (28.5 g, 0.117 mol) in 50 ml THF was added under Ar for 2.5 hours to a solution of Grignard reagent prepared as described above. The combined solution was then diluted with 100 ml THF, followed by stirring of the mixture at room temperature for another 1.5 hours. The mixture was allowed to stand at room temperature overnight. After heating the reaction mixture at reflux temperature for 5 hours, it was cooled and evaporated. The portion remaining after evaporation was diluted with 100 ml hexane to give a crystalline precipitate. The crystals were then filtered off, washed with 1:10 ether-petroleum ether and dried in vacuo at 80° C. for 1 hour and at 110–130° C. for 4 hours. Thirty-seven g (64% yield) of (–)-CPT was obtained having a melting point of 172–175° C. NMR (δ, ppm) in CDCl₃: 1.3–1.65 m (8H, 4CH₂), 3.82 s (2H, 20H), 4.7 s (2H, 2CHO), 7.15–7.6 m (20H, 4Ph). $[\alpha]_D^{20}$ value of –35.0° ©. 1, CHCl₃. This $[\alpha]_D^{20}$ value differed from that obtained earlier for the preceding lot of (–)-CPT.

PREPARATION OF COBALT CATALYSTS

Two types of procedure were used to prepare Co(BSIC)₂ using COCl₂ and Co(OAc)₂ as starting reagents. Anhydrous COCl₂ and Co(OAc)₂ were prepared by drying the corresponding hydrates in vacuo at 50–120° C. The synthesis of BSIC has been described in Example 5.

Example 12

Preparation of Co(BSIC)₂ from CoCl₂ (catalyst 1)

Anhydrous CoCl₂ (33 mg, 0.254 mmol) and BSIC (97 mg, 0.301 mmol) were dissolved in 8 ml THF to give a dark-brown solution. After about 30 minutes, a brown solid complex precipitated and the mixture was cooled to –20° C. and kept at this temperature for 1hour. The precipitate was filtered off, washed with THF, and dried at room temperature in vacuo to give 69 mg (33% yield) of crude complex. Observed % composition of the complex: O, 59.04; H, 5.08; N, 4.98; Co, 13.86; Cl, 5.92. C₂₀H₂₀N₂O₂Co. Calculated % composition: C, 63.36; H, 5.27; N, 7.39; Co, 15.54. Pure Co(BSIC)₂ was obtained by recrystallization of the crude product from THF. Its IR spectrum was in accordance with that reported in J. Organomet. Chem. 1975, 85 241.

(1R, 2R)-BSIC + CoCl$_2$ ⟶

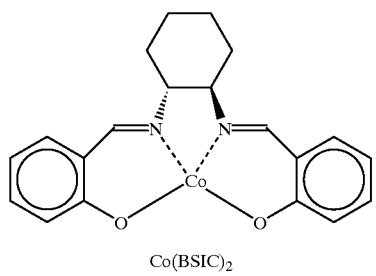

Co(BSIC)$_2$

Example 13

Preparation of Co(BSIC)$_2$ from Co(OAc)$_2$ (catalyst 2)

This experiment was carried out following a procedure described in J. Organomet. Chem. 1975, 85, 241. A solution of anhydrous Co(OAc)$_2$ (675 mg, 4.6 mmol) and (1R, 2R)-BSIC (1.5 g, 4.65 mmol) in 21 ml anhydrous 1-propanol was heated in Ar atmosphere at 60° C. for 1 hour and cooled to 0–2° C. After 24 hours, the orange-red powder that precipitated was filtered off and dried at room temperature in vacuo (1–2 torr) to give 1.3 g (60% yield) of the product Co(BSIC)$_2$. Its infrared spectrum was consistent with literature data.

Example 14

Preparation of the solid NaAl[(+)-DDM]H$_2$ Under Various Conditions and Study of its Stability at 0–2° C[a].

NaAl[(+)-DDM]H$_2$ was prepared by mixing sodium aluminum hydride (SAH) with (+)-DDM in THF. The table below shows the various reaction conditions and results of tests on the stability of the NaAl[(+)-DDM]H$_2$ complex at 0–2° C. The table also shows the chemical and e.e. yields obtained from the asymmetric reduction of PP into PEP using NaAl[(+)-DDM]H$_2$.

TABLE 1

Preparation of solid NaAl[(+)-DDM]H$_2$ under different conditions and study of its stability at 0–2° C.[a]

| | Preparation of a solution of NaAl[(+)-DDM]H$_2$ in THF | | | | Isolation of solid NaAl[(+)-DDM]H$_2$ | | | | |
|---|---|---|---|---|---|---|---|---|---|
| Entry | SAH mmol (mg) | Molar ratio SAH: DDM | Volume of H$_2$ gas (mL) evolved, found/calcd | Procedure | Visual appearance of the complex | Exposure conditions of the solid in closed vessel (under Ar), °C./time | Volume of H$_2$ gas evolved (ml) after quenching the solid complex after exposure, observed/calc | Loss of active hydrogen for the solid complex after exposure, % | Conversion of PP, %/ e.e. for PEP, %[c] |
| 1 | 0.5 (27) | 1:0 | 45.0/44.8 | — | — | — | — | — | — |
| 2 | 0.5 (27) | 1:1.05 | 27.1/23.5 | — | — | — | — | — | —[b] |
| 3 | 0.5 (27) | 1:1.05 | 27.0/23.5 | A | pale-yellow foam-like solid | 20/1h | 17.1/17.7 | 3 | — |
| 4 | 1 (54) | 1:1.05 | 49/47 | A | pale-yellow foam-like solid | 20/1h | 40/40.6 | 1.5 | — |
| 5 | 0.5 (27) | 1:1.05 | 26.7/23.5 | A | pale-yellow foam-like solid | 20/1h | — | — | 100/67 (R) |
| 6 | 0.5 (27) | 1:1.05 | 24.1/23.5 | B | fine white powder | 20/1h | 10.2/20.7 | 51 | — |
| 7 | 0.5 (27) | 1:1.05 | 27.0/23.5 | B | fine white powder | 0–2/40 days | 8.5/17.8 | 52 | — |
| 8 | 0.5 (27) | 1:1.05 | 27.0/23.5 | B | fine white powder | 0–2/40 days | — | — | 45/81 (R) |
| 9 | 0.5 (27) | 1:1.05 | 25.9/23.5 | B | fine white powder | 20/1h | 12.5/18.9 | 34 | — |
| 10 | 0.5 (27) | 1:1.05 | 26.0/23.5 | B | fine white powder | 20/1h | — | — | 100/67 (R) |

[a]7 ml THF was used in each experiment to prepare NaAl[(+)-DDM]H$_2$ from SAH and DDM

[b]With respect to the "active" hydrogen content of the dried solid complex before exposure in the closed vessel

[c]The solid dihydride complex exposured under conditions indicated was used for reduction of PP; [Al]:[PP] = 1:0.5; 7 ml of THF; room temperature; 2 hours; products analyzed by GC.

Example 15

Preparation of $Ph_2P(O)Cl$ $O_2$ gas was dried by passing through $CaCl_2$, $P_2O_5$, and molecular sieves (4Å). The dry $O_2$ gas was bubbled through a 10 ml solution of $Ph_2PCl$ in 80 ml toluene for 3 hours (the reaction was slightly exothermic). Distillation of the reaction mixture gave 10.2 g (80% yield) of pure $Ph_2P(O)Cl$ having a boiling point of 172–3° C. (1 torr). $^{31}$P-NMR (δ, ppm) in $CDCl_3$: 42.77 (the only detected signal). $^1$H-NMR (δ, ppm) in $CDCl_3$: 7.2–7.5 m (6H, aromatic), 7.6–7.8 d/d (4H, aromatic).

Example 16

Decomposition Rate of Solid NaAl[(−)-(CYTOL)]$H_2$

A solution of SAH (27 mg, 0.5 mmol) in 1.3 ml THF was added at room temperature in one portion (using a syringe) into a stirred solution of (−)-CYTOL (256 mg, 0.525 mmol) in 5.7 ml THF. The resulting NaAl[(−)-CYTOL]$H_2$ solution was allowed to stand at room temperature for 1 hour and evaporated in vacuo at room temperature leaving behind a solid dihydride complex. The solid complex was then allowed to stand at room temperature over a period of 34 days in a carefully sealed glass flask and placed in a NaOH-containing dessicator. Quenching of the complex produced 38.5 ml of $H_2$ gas. This volume of $H_2$ gas corresponds to a 29% loss of "active" hydrogen giving a decomposition rate of 0.85% per day for the solid NaAl[(−)-CYTOL]$H_2$. This decomposition rate is similar to those of solid DDM- and CPT-derived dihydride complexes.

Example 17

Stability of Solid NaAl[(−)-CYTOL]$H_2$

NaAl[(−)-CYTOL]$H_2$ was dissolved in 5 ml THF and the solution was cooled to −20° C. Into this solution was added PP (33 mg, 0.5 mmol), and the reaction mixture was allowed to stand at −20° C. for 20 hours. After quenching the reaction mixture, the products were analyzed by GC showing a PP conversion of 38% and e.e. value of 80% (S) for PEP. The observed high stereoselectivity of the hydride reduction of PP showed there was no "aging effect" even though the solid dihydride had been stored at room temperature for at least one month prior to use.

Example 18

Thermostability of 2:1 DDM-CPE Host-Guest Complex

Several samples of the DDM*CPE complex were heated under vacuum (5 torr) at various temperatures for 15 minutes. The samples were then analyzed by NMR. As can be seen in Table 2, the temperature appropriate for safe drying of HGC is between 40–50° C. On the other hand, when it is desired to separate CPE from the host compound, the complex should be heated between 70–90° C.

TABLE 2

Thermostability of the 2:1 (−)-DDM-(S)-CPE host-guest complex at various temperatures*

| Expt. | HG-239 | HG-240 | HG-241 | HG-242 | HG-243 | HG-244 | HG-245 |
| --- | --- | --- | --- | --- | --- | --- | --- |
| Temperature, °C. | 30 | 40 | 50 | 60 | 70 | 80 | 90 |
| H*/G molar ratio for crystalline HGC(NMR) | 2:1 | 2:1 | 2:1 | 3:1 | 1:0 | 1:0 | 1:0 |
| Loss of CPE included into HGC, % | 0 | 0 | 0 | 34 | 100 | 100 | 100 |

*The sample was heated in vacuo (5 torr) over a period of 15 minutes and analyzed by NMR.

ASYMMETRIC HYDRIDE REDUCTION OF CARBONYL COMPOUNDS WITH Na-TADDAL-$H_2$ REDUCING AGENTS

Example 19

Reduction of α-ketoester EOPB with SAH Modified by Various TADDOLs

Hydride reduction of EOPB using various Na-TADDAL-$H_2$ reducing agents gave a relatively low α-ketoester conversion (25–50%) when the reaction was run for 2 hours at −20° C. To attain higher conversion values at the same temperature, the reaction durations were extended to as long as 20 hours. Chiral ligands were prepared using the following methods: crystallization from a solution in a closed flask (Procedure A); inclusion crystallization in a suspension (Procedure B); and crystallization from a solution by slow evaporation of the solvent at room temperature (Procedure C). In all experiments, Procedure A was performed first. If no crystals precipitated at room temperature, either the solution was cooled to −15° C. or a different method was used. The results of the experiments obtained using Procedure A are shown in Table 3.

TABLE 3

Asymmetric Reduction of EOPB with various Na-TADDAL-$H_2$ reducing agents

| | Preparation of NaAl(L*)H2 | | | | Volume of $H_2$ gas | Asymmetric hydride reduction of EOPB to (S)-EHPB | | | | |
|---|---|---|---|---|---|---|---|---|---|---|
| | SAH, | Ligand | | | evolved (ml) | mmol (mg) of | Molar ratio | | conversion of EOPB, | |
| Exp | mmol (mg) | Name | mmol (mg) | THF, ml | observed/ calc | Al: EOPB | Al: EOPB | °C./h | % (GC) | e.e., % (GC) |
| (−)-DDM-82 | 05 (27) | (−)-DDM | 0.525 (245) | | 23.9/23.5 | 1 (206) | 1:2 | −20/2 | 65 | 29 (30*) (S) |
| (−)-PENTOL-7 | 0.5 (27) | (−)-PENTOL | 0.525 (260) | 7 | 24.3/23.5 | 1 (206) | 1:2 | — 20/20 | 84 | 35 (S) |
| (−)-FLUTOL-8 | 0.5 (27) 20/20 | (−)-FLUTOL | 0.525 (309) | 7 | 22.5/23.5 | 1 (206) | 1:2 | — 20/20 | 90 | 32 (S) |
| (−)-CPT-22 | 0.5 (27) | (−)-OPT | 0.525 (258) | 7 | 23.9/23.5 | 1 (206) | 1:2 | — 20/20 | 88 | 35 (5) |
| (−)-CYTOL-41 | 0.5 (27) | (−)-OYTOL | 0.525 (265) | 7 | 23.9/23.5 | 1 (206) | 1:2 | — 20/20 | 78 | 37 (S) |
| (−)-ITM-11 | 0.5 (27) | (−)-ITM | 0.525 (308) | ~ | 23.9/23.5 | 1 (206) | 1:2 | — 20/20 | 84 | 37 (S) |

*E.e. values indicated in parentheses were determined by HPLC: Chiralcel OD, 10% 2-pro panol-hexane, ~1 ml/min,
γ = 254 nm; elution times for the products in minutes: 4.5 (EOPB) 4.83 ((S)-EHPB), 6.33 ((R)-EHPB)
*GC means the values were measured by gas chromatography An increase in the EOPB conversions (by a factor of 2–2.5) to 80–90% was achieved in the reaction of EOPB with various Na-TADDAL-$H_2$ reducing agents by increasing the reaction time at —20° C. from 2 to 20 hours. It should be noted that relatively high conversions were obtained using a 2:1 substrate:Al molar ratio. All TADDOLs used as chiral auxiliaries in the hydride reduction of EOPB showed similar stereoselectivities (29–37% e.e.) in accordance with previous results.

Example 20

Hydride Reduction of PP and EOPB with Na-TADDAL-$H_2$

The goal of the experiments below was to determine the ability of various chiral ligands to form HGC's with products obtained from the hydride reduction of PP and EOPB. For this purpose, the reaction mixtures obtained earlier after hydride reduction were allowed to evaporate slowly, and the resulting crystalline precipitates subsequently analyzed. These experiments allowed the selection of ligands best suited for tandem reduction-HG complexation. Chiral ligands were prepared as described earlier. After quenching each reaction mixture and separating the aluminum-containing solid, the reaction mixture was left at room temperature in loosely stoppered flasks to allow the solvent to evaporate slowly. After the maximum amount of crystals has precipitated within 2–3 weeks, the crystals were filtered off and analyzed by NMR and GC.

From Table 4, it can be seen that the ligand (−)-PENTOL forms an HGC with the reduction product PEP, the enantiomeric enrichment of PEP taking place as a result of its inclusion crystallization with the ligand (−)-PENTOL (from 60% e.e. to 92% e.e.; see Expt. (−)-PENTOL-1,2 (C)). When ether-hexane was used as solvent and THF was only a minor component of the solution, a high (−)-PENTOL/PEP molar ratio (L*:PEP) of 5:1 was obtained. This is due to the co-crystallizaiton of (−)-PENTOL with the complex (−)-PENTOL*PEP.

The result obtained in Expt. (−)-PENTOL-1,2 (C) shows that (−)-PENTOL can be considered an appropriate chiral auxiliary in tandem reduction-HG complexation. In contrast to PENTOL, another ligand, FLUTOL, proved to be inactive towards host guest complexation with PEP under the given experimental conditions (Expt. (−)-FLUTOL-1 (C)), although a crystalline HGC containing (−)-FLUTOL and THF in a 1:1 molar ratio was isolated from the reaction mixture in Expt. (−)-FLUTOL-5 (C). Table 4 further shows that none of the ligands used formed HGC's with EHPB. In the other experiments, no HGC's were formed, i.e., the only products that precipitated consisted of uncomplexed chiral ligands.

TABLE 4

Hydride reduction of PP and EOPB in the form of HGC's

| | | composition of the reaction solution[a] | | | composition of the solid after its crystallization from the reaction mixture | | | |
|---|---|---|---|---|---|---|---|---|
| | | The product of hydride reduction | | | crystalline solid | Guest | composition of HGC | e.e. value guest (G) included |
| Expt. | Name | e.e., % (GC) | chiral ligand (L*) | Solvent | (L* or HGC) | compound (G) | L*:G (NMR) | into HGC, % (GC) |
| 1 | PEP | 60 (S) | (−)-PENTOL | ether-hexane THF[b] | HGC | PEP | 5:1 | 92 (S) |
| 2 | PEP | 75 (S) | (−)-FLUTOL | ether-hexane THF[b] | L* | — | — | — |
| 3 | EHPB | 29 (S) | (−)-FLUTOL | ether-hexane THF[b] | HGC | THF | 1:1 | — |
| 4 | EHPB | 25 (S) | (−)-CPT | ether-hexane THF[b] | L* | — | — | — |
| 4 | EHPB | 26 (S) | (−)-CYTOL | ether-hexane THF[b] | L* | — | — | — |
| 6 | EHPB | 37 (S) | (−)-ITM | ether-hexane THF[b] | L* | — | — | — |

[a]After asymmetrical hydride reduction of PP or EOPB with Na-TADDAL-H$_2$.
[b]THF was a minor component of the solutions.

Example 21

Inclusion Crystallization of PET with (−)-PENTOL and (−)-FLUTOL

Although (−)-PENTOL has been found to form HGC's with PET and with PEP, their true stoichiometries (H*/G ratio) have not been determined. As shown earlier, (−)-FLUTOL gave a 1:1:1 (−)-FLUTOL*PET*THF ternary-complex after reducing AP with NaAl[(−)-FLUTOL]H$_2$ in THF. However, no enantiomeric enrichment of the included PET was observed prior to crystallization of the ternary HGC. Results of experiments involving inclusion crystallization of PET with (−)-PENTOL and (−)-FLUTOL are shown below.

As can be seen from Table 5, (−)-PENTOL formed HGC's with PET when 1:5 ether-hexane or 1:5 THF-hexane was used as solvent. However, an HGC having a true H*/G stoichiometry of 2:1 appears to crystallize only from THF-hexane (Expt. HG-198). In experiment HG-197 performed in ether-hexane, co-crystallization of (−)-PENTOL with the 2:1 (−)-PENTOL*PET complex appeared more favourable than crystallization of the 2:1 HG complex alone. The isolated crystals where co-crystallization has occurred consequently had a high H*/G ratio (6:1). It should be noted that the presence of THF in the reaction mixture facilitated the crystallization of the 2:1 DDM-PET complex affording a considerably higher HGC yield in the tandem reduction-HG complexation procedure.

In both Expts. HG-197 and HG198, a high degree of stereoselectivity after the first crystallization was attained for the HGC formed by inclusion of PET into (−)-PENTOL (72 and 78% respectively). Unexpectedly, the (R)-enantiomer of PET formed the predominant HGC with (−)-PENTOL instead of the (S)-enantiomer. It is also interesting to note that two similar chiral hosts, (−)-DDM and (−)-PENTOL, both prepared from the same natural tartaric acid, formed predominant HGC's containing PET enantiomers of opposite configurations, namely, 2:1 (−)-DDM*(S)-PET and 2:1 (−)-PENTOL*(R)-PET. This result, obtained from the resolution of a racemic substrate, was the first of its kind observed by the inventor.

TABLE 5

Inclusion crystallization of α-phenylethanol (PET) with (−)-PENTOL and (−)-FLUTOL

| | Conditions for HG complexation | | | | | | | Crystalline product | | | | |
|---|---|---|---|---|---|---|---|---|---|---|---|---|
| | Host compound | | H*/(±) PET molar ratio in soln. | | | | | | Guest compound | H*/G molar ratio | Yield of HGC or H* | e.e. for PET included into HGC, % |
| Expt. | Name | (H*) mmol (mg) | | Solvent | Procedure | °C./days | HGC or H* | HGC or compound | (G) | (NMR) | mg | % | (GC) |
| HG-197 | (−)-PENTOL | 0.25 (124) | 1:4 | ether (1)-hexane | A | 20/5 | HGC[a] | PET | 6:1 | 62 | 17 | 72 (R) |

TABLE 5-continued

Inclusion crystallization of α-phenylethanol (PET) with (−)-PENTOL and (−)-FLUTOL

| | Conditions for HG complexation | | | | | | | | Crystalline product | | | |
|---|---|---|---|---|---|---|---|---|---|---|---|---|
| | Host | | H*/(±) | | | | | | | Yield | | e.e. for PET |
| | compound | | | | | | | | | | | |
| | (H*) | PET | | | | | Guest | H*/G | | | | included into |
| | | mmol | molar ratio | | | °C./ | HGC or | compound | molar ratio | of HGC or H* | | HGC, % |
| Expt. | Name | (mg) | in soln. | Solvent | Procedure | days | H* | (G) | (NMR) | mg | % | (GC) |
| HG-198 | (−)-PENTOL | 0.25 (147) | 1:4 | THF (1)-hexane (5) | A | 20/5 | HGC[b] | PET | 2:1 | 88.5 | 64 | 78 (R) |
| HG-199 | (−)-FLUTOL | 0.25 (147) | 1:4 | ether (1)-hexane (5) | A | 20/5 | H*[b] | — | — | 109 | 74 | — |
| HG-200 | (−)-FLUTOL | 0.25 (147) | 1:4 | THF (1)-hexane (5) | A | 20/5 | HGC[c] | PET, THF | 1:1:0.3[d] | — | — | 0 |
| HG-201 | (−)-FLUTOL | 0.25 (147) | 1:0 | THF (1)-hexane (5) | A | 20/5 | HGC[c] | THF | 1:1 | — | — | — |

[a]Thin branched needles that are typical for crystals of (−)-PENTOL
[b]Sandlike white crystals
[c]Snowlike crystals
[d](−)-FLUTOL*PET*THF Further enrichment of (S)-PET (obtained from the reduction of AP with NaAl[(−)-PENTOL]H$_2$) was observed via crystallization of the (−)-PENTOL*(S)-PET complex from the reaction solution. Also, (−)-PENTOL proved capable of producing HGC's with both enantiomers of PET depending on the (R)/(S) ratio of the starting substrate. A similar effect of the initial (R)/(S) ratio of the substrate on the stereochemical outcome of HG complexation was recently observed in the (+)-CYTOL*IPG system.

Experiments HG-199–HG-201 demonstrate the influence of the nature of the solvent on the ability of the ligand/host (−)-FLUTOL to form an HGC with PET. In spite of a 4-fold excess of (±)-PET relative to (−)-FLUTOL in a starting 1:5 ether-hexane solution, no (−)-FLUTOL*PET complex was obtained in Expt. HG-199 (only the host compound (−)-FLUTOL crystallized from this solvent). In contrast, a crystalline ternary complex (−)-FLUTOL*PET*THF in a 1:1:0.3 ratio was isolated using 1:5 THF-hexane (Expt. HG-200) as solvent. The result of this run is similar to that of a previous experiment in which a 1:1:1 (−)-FLUTOL*PET*THF complex was isolated from the reaction solution after reducing AP with NaAl[(−)-FLUTOL]H$_2$. In both experiments, no enantiomeric enrichment of PET was obtained. The reduced amount of THF in the HGC isolated in Expt. HG-200 may be due to the loss of THF in the course of drying the 1:1:1 HGC. Also, the blank experiment HG-201 shows that the true H*/G stoichiometry of the (−)-FLUTOL*THF complex obtained in the absence of a substrate is 1:1.

The above results obtained with (−)-FLUTOL as host compound are also similar to those previously observed in the HG complexation of (−)-FLUTOL with IPG: although a crystalline 2:1 (−)-FLUTOL*IPG complex was previously isolated, no optical enrichment of IPG due to HG complexation took place.

Example 22

Optical Resolution of (±)-PL by Inclusion Crystallization Using Various TADDOLs

Previous experiments on the optical resolution of (±)-PL yielded a 1:1 (±)-CYTOL*(S)-PL host-guest complex with a 36% chemical yield and 69% e.e. of PL included into the HGC. The goal of the experiments below was to examine the ability of a number of TADDOLs to form solid HGC's with PL. The results are shown in Table 6.

Compared to (±)-CYTOL, (−)-CYTOL as host allowed a higher degree of resolution of the guest PL included into the HGC (85% e.e. (R)) but almost the same yield of HGC (42% relative to the starting host; Expt. HG-202). In stark contrast to Expt. HG-202, Expts. HG-203 and HG-204 (conducted at 115° C.) yielded practically 0% e.e. values. The use of other TADDOLs produced no apparent optical resolution of (±)-PL.

TABLE 6

Resolution of (±)-PL by inclusion crystallization using chiral diols

| | | Conditions for HG complexation | | | | | crystalline product | | | |
|---|---|---|---|---|---|---|---|---|---|---|
| | | H*/(±)PL | | | | | | | | |
| | Host compound (H*) | molar ratio in | | | | | | H*/G molar | Yield of HGC, | e.e. for PL included into |
| Expt. 1 | Name | mmol (mg) | starting soln. | Solvent, ml | Procedure | °C./h | HGC or H* | Guest compound (G) | ratio (NMR) | mg (%) | HGC, % (GC) |
|---|---|---|---|---|---|---|---|---|---|---|---|
| HG-202 | (−)-CYTOL | 0.25 (127) | 1:4 | ether (2)- hexane (5) | A | 10–13/ /72 | HGC | PL | 1:1 | 66 2 (42)[b] | 85 (R) |
| HG-203 | (−)-CYTOL | 105 (760) | 1:4 | ether (12)- hexane (30) | A | −15/24 | HGC | PL | 1:4.5 | 1045 | 3 (R) |
| HG-204 | (−)-CYTOL | 0.25 (127) | 1:2 | ether (3) - hexane (5) | A | −15/48 | C | —[c] | — | — | — |
| HG-205 | (−)-CPT | 0.25 (123) | 1:4 | ether (1)- hexane (5) | A | 20/24 | HGC | PL | 1:2.5 | 140 | 18 (S) |
| HG-206 | (−)-PEN-TOL | 0.25 (124) | 1:4 | ether (1) hexane (5) | A | 20/24 | HGC | PL | 1:2 | 158 | 0 |
| HG-207 | (−)-DDM | 0.25 (116) | 1:4 | ether (1)- hexane (5) | A | 20/24 −15/3 | HGC | PL | — | — | 11 (R) |
| HG-208 | (−)-ITM | 0.25 (146) | 1:4 | ether (3)- hexane (5) | B[c] | 20/24 | H* | — | — | 115 | — |
| HG-209 | (−)-FLU-TOL | 0.25 (132) | 1:4 | ether (4) - hexane ( 5) | C | 20/24 −15/3 | HGC | PL | 1:3 | 142 | 5 (R) |
| HG-210 | (−)-DPPD | 0.25 (57) | 1:4 | ether (1) - hexane (5) | A | 20/24, −15/3 | HGC | PL | 1:3 | 106 | 0 |
| HG-211 | (+)-TPED | 0.25 (73) | 1:4 | ether (1)- hexane (5) | A | 20/24 | HGC | PL | 1:2.5 | 98 | 0 |
| HG-212 | (+)-IPTET | 0.25 (61) | 1:4 | ether (1)- hexane (5) | A | 20/24, −15/2 | —[c] | — | — | — | — |

[a] (−)-ITM is slightly soluble in ether even without adding hexane.
[b] Referred to the starting host compound.
[c] No crystallization was observed.

Example 23

Asymmetric Hydride Reduction of Various Carbonyl Compounds with NaAl[(−)-DDM]H₂

Reagents were prepared as described earlier. Procedure A was used in the hydride reduction of the carbonyl compounds except PP. Table 9 shows the results of the experiments. In Expts. (−)-DDM-83 and (−)-DDM-84, the inventor used Procedure B to isolate the solid hydride reagent after evaporating THF. The solid complex obtained was redissolved either in THF (Expt. 83) or in CH₂Cl₂ (Expt. 84).

In these hydride reductions using Na-TADDAL-H₂ as reducing agents, ether-type solvents (THF, DME, diglyme and ether itself) were used. Expt. (−)-DDM-84 was the first experiment using a halogen-containing hydrocarbon in a reduction using a TADDOL-modified SAH. Comparison of Expts. 83 and 84 shows that the stereoselectivity of PP reduction using NaAl(DDM)H₂ is reduced by half when CH₂Cl₂ is substituted for THF, all other conditions being the same.

TABLE 9

Asymmetric hydride reduction of various carbonyl compounds with NaAl(DDM)H₂

| | Preparation of NaAl[(−)-DDM]H₂ | | | | Asymmetric hydride reduction | | | | | | |
|---|---|---|---|---|---|---|---|---|---|---|---|
| | SAH, | (−)-DDM, | Solvent | Vol. of H₂ gas evolved, ml | Substrate | | Molar ratio | | Conversion of substrate | | e.e., % |
| Expt. | mmol (mg) | mmol (mg) | (ml) | (observed/ calc) | Name | mmol (mg) | Al: sub-strate | °C./h | % (GC)[c] | Product | (GC) |
|---|---|---|---|---|---|---|---|---|---|---|---|
| (−)-DDM-83 | 0.5 (27) | 0.525 (245) | THF (7) | 24.9/ 23.5 | PP | 0.5 (33) | 1:1 | −70/20 then −70-20(1) | 84 | (S)-PEP | 83 |
| (−)-DDM-84 | 0.5 (27) | 0.525 (245) | CH₂Cl₂ (5) | 25.8/ 23.5 | PP | 0.5 (33) | 1:1 | −70/20 then −70-20(1) | 82 | (S)-PEP | 43 |
| (−)-DDM-85 | 0.5 (27) | 0.525 (245) | THF (7) | 23.9/ 23.5 | CMK | 0.167 | 3:1 | 20/2 | 97 | (S)-CPE | 34 |

TABLE 9-continued

Asymmetric hydride reduction of various carbonyl compounds with NaAl(DDM)H$_2$

Preparation of NaAl[(−)-DDM]H$_2$

| Expt. | SAH, mmol (mg) | (−)-DDM, mmol (mg) | Solvent (ml) | Vol. of H$_2$ gas evolved, ml (observed/ calc) | Substrate Name | mmol (mg) | Molar ratio Al: substrate | °C./h | Conversion of substrate % (GC)[c] | Product | e.e., % (GC) |
|---|---|---|---|---|---|---|---|---|---|---|---|
| (−)-DDM-86 | 0.5 (27) | 0.525 (245) | THF (7) | 22.5/ 23.5 | CMK | 0.167 | 3:1 | 20/20 | 98 | (S)-CPE | 40 |
| (−)-DDM-87 | 0.5 (27) | 0.525 (245) | THF (7) | 22.5/ 23.5 | CMK | 0.167 | 3:1 | 20/72 | 98 | (S)-CPE | 33 |
| (−)-DDM-88 | 0.5 (27) | 0.525 (245) | THF (7) | 24.3/ 23.5 | EOPB | 0.5 (103) | 1:1 | −70/44 then −70-20(1) | 89 | (S)-EHPB | 35 |
| (−)-DDM-89 | 0.5 (27) | 0.525 (245) | THF (7) | 24.3/ 23.5 | EOPB | 1 (206) | 1:2 | −70/44 then −70-20(1) | 52 | (S)-EHPB | 35 |
| (−)-DDM-82 | 0.5 (27) | 0.525 (245) | THF (7) | 23.9/ 23.5 | EOPB | 1 (206) | 1:2 | −20/2 | 65 | (S)-EHPB | 29 (30) |
| (+)-DDM-129 | 0.5 (27) | 0.525 (245) | THF (7) | 26/23.5 | EOPB | 1 (206) | 1:2 | −20/20 | 98 | (R)-EHPB | 29 |
| (+)-DDM-128 | 0.5 (27) | 0.525 (245) | THF (7) | 26/23.5 | EOPB | 1 (206) | 1:2 | 20/20 | 99 | (R)-EHPB | 29 |
| (+)-DDM-119 | 0.5 (27) | 0.525 (245) | THF (7) | 26/23.5 | EOPB | 0.5 (103) | 1:1 | 15/20 | 80 | (R)-PL | 37 |
| (−)-DDM-90 | 0.5 (27) | 0.525 (245) | THF (7) | 23.9/ 23.5 | DMFD | 0.25 (32) | 2:1 | −70/20 then −70-20(1) | 80 (100)[a] | (R)-PL | 18 |
| (−)-DDM-91 | 0.5 (27) | 0.525 (245) | THF (7) | 25.2/ 23.5 | DMFD | 0.5 (64) | 1:1 | −70/44 then −70-20(1) | 75 | (R)-PL | 32 |
| (−)-DDM-92 | 0.5 (27) | 0.525 (245) | THF (7) | 25.2/ 23.5 | DMFD | 1 (128) | 1:2 | −70/44 then −70-20(1) | 45 | (R)-PL | 21 |
| (−)-DDM-93[b] | 0.5 (27) | 0.525 (245) | THF (7) | 31.3/ 33.5[b] | DMFD | .05 (64) | 1:1 | −70/44 then −70-20(1) | 3[b](<5[a]) | (R)-PL | 22 |
| (−)-DDM-79 | 0.5 (27) | 0.525 (245) | THF (7) | 26.2/ 23.5 | DMFD | 1 (128) | 1:2 | −20/2 | 31 | (R)-PL | 27 |
| (−)-DDM-78 | 0.5 (27) | 0.525 (245) | THF (7) | 25.7/ 23.5 | DMFD | 0.5 (64) | 1:1 | −20/2 | 96 | (R)-PL | 35 |
| (+)-DDM-121 | 0.5 (27) | 0.525 (245) | THF (7) | 26/23.5 | DMFD | 0.5 (64) | 1:1 | 15/20 | 45 | (S)-PL | 19 |

[a] Values indicated in parentheses were determined by NMR for products separated from the ligand by bulb-to-bulb distillation.
[b] Monohydride complex NaAl[(−)-DDM](OMe)H was used in this run.
[c] Calculated from ratios of GC peak squares or integral intensities of signals on NMR spectra which corresponds in each case to the starting substrate and final product.

Expts. (−)-DDM-85, (−)-DDM-86 and (−)-DDM-87 represent the first runs in which a non-aromatic ketone, CMK, was examined as prochiral substrate in the reaction with Na-TADDAL-H$_2$ reducing agent. In these runs, high conversion of CMK into CPE (97–98%) and moderate enantioselectivity (30–40% e.e.) were obtained. These results are similar to those obtained using different reaction times (2, 20 and 72 hours).

It should be noted that the reaction temperature did not exert a marked effect on the stereoselectivity of reduction when substrates such as EOPB were used at temperatures ranging from −70° C. to room temperature, the e.e. values in all runs remaining within the 30–40% range (see Expts. (−)-DDM-88, (−)-DDM-89). The absence of any apparent effect of the reaction temperature on the stereochemical outcome of hydride reduction in the above experiments was also observed in the reaction between NaAl(DDM)H$_2$ and the α-ketoester (more precisely, the α-ketolactone) DMFD, the e.e. values obtained being within 20–30% (see Expts. (−)-DDM-88 and (−)-DDM-89).

It is also interesting to note that substituting the monohydride complex NaAl(DDM)(OMe)H with a dihydride complex produced a mere 3% conversion of DMFD (see Expt. (−)-DDM-93). In general, the reaction mixtures obtained after the reduction of DMFD contained considerable amounts of other by-products probably arising from the reduction of the ester group of either DMFD or PL, or both.

As can be seen from Table 9, the stereoselectivity of hydride reduction of various carbonyl compounds with NaAl(DDM)H$_2$ decreases in the order

PP>CMK, EOPB>DMFD

(80) (30–40) (30–40) (20–30)

where the numbers in parentheses correspond to the observed ranges of % e.e.

Example 24

Stereoselective Resolution of (±)-CPE via 2-step Inclusion Crystallization with (+)-DDM As shown in Table 10 below, four out of the five e.e. values obtained in the stereoselective resolution of (±)-CPE (using a 2-step inclusion crystallization with (+)-DDM) cluster around a respectable 76%. There appears to be no clear correlation between the experimental parameters shown and the sudden jump in e.e. value to 87% in Experiment 6 where the absolute amounts of ether/hexane has been increased from 0.51:5.1 in Experiment 5 to 0.55:5.5 in Expt. 6, the ether/hexane ratio for the six experiments all remaining at $^1$/$_{10}$.

Example 25

Tandem Asymmetric Reduction-HG Complexation of AP with NaAl[(+)-DDM]H$_2$

Table 11 shows that while the chemical yields average only about 50%, the average e.e. value is about 93% demonstrating that DDM is a highly effective chiral auxilliary in the tandem asymmetric reduction-host guest complexation of acetophenone. The relative amount of THF in these experiments appear not to have much effect on both the chemical yields and the e.e. values.

Example 26

Inclusion Crystallization of Various Guest Compounds with TADDOLS

The following host compounds were prepared as described earlier. Procedure A (crystallization from a solution in a closed flask), Procedure B (inclusion crystallization in suspension) or Procedure C (crystallization upon gradual evaporation of a solution at room temperature) were used. In all experiments Procedure A was conducted first. If no crystals precipitated at room temperature after 1 day, the solution was cooled to 0° C. for the same duration. If still no crystals formed, the solution was further cooled down to −15° C. If this step proves unsuccessful, Procedure C was then used.

Moreover, the e.e. values for both the R and S configurations of the reduction product obtained with both (−)-DDM and (+)-DDM were also surprisingly identical in addition to the very high conversion in all but one experiment (Experiment 4).

Example 27

Stereoselective Resolution of (±)-CPE via Inclusion Crystallization with (+)-DDM Table 13 below shows that while Expts. 2, 3, and 4 did not yield any HGC in the second crystallization stage, Expt. 1 gave a 100% e.e. of (±)-CPE included into (+)-DDM. The results seem to suggest that success in obtaining HGC in the second stage of crystallization depends upon the initial amounts of ligand and substrate because no HGC in the second stage was obtained when the initial amounts of DDM and CPE were decreased by ¼ the amount used in Expt. 1 (see Expts. 2, 3, and 4). Further reduction in the initial amounts of DDM and CPE results in no HGC formation in the second stage and also a substantial decrease in the first stage e.e. values (from more than 90% to less than 20%) as can be seen from the results of Experiments 5, 6, and 7. Also, in Expt. 1c, although the e.e. was also 100% in the second stage, the chemical yield was only ⅓ that obtained in Experiment 1b.

TABLE 10

Stereoselective resolution of (±)-CPE via 2-step crystallization with (+)-DDM

| | | Inclusion crystallization conditions | | | | | Starting | |
|---|---|---|---|---|---|---|---|---|
| | | | | 2:1 HGC | | | | |
| Entry | Stage | (+)-DDM (H*), mmol (mg) | (±)-CPE mmol (mg) | mg | e.e. of CPE included into HGC, % | Solvent, ml | G:H* molar ratio in solution | ° C./days |
| 1a | Stage 1 | 0.75 (350) | 3 (258) | — | — | ether (3)-hexane (15) | 4:1 | −25/3 |
| 1b | Stage 2 | — | — | 188 | — | ether (0.37) - hexane (3.7) | 0.133:1 | −25/1 |
| 2a | Stage 1 | 0.75 (350) | 3 (258) | — | — | ether (3) - hexane (15) | 4:1 | −25/3 |
| 2b | Stage 2 | — | — | 217 | 76 (R) | ether (0.42) - hexane (4.2) | 0.43:1 | −25/1 |
| 3a | Stage 1 | 0.75 (350) | 3 (258) | — | — | ether (1.5) - hexane (15) | 4:1 | −25/3 |
| 3b | Stage 2 | — | — | 249 | 76 (R) | ether (0.49) - hexane (4.9) | 0.42: 1 | −25/1 |
| 4a | Stage 1 | 0.75 (350) | 3 (258) | — | — | ether (1.5) - hexane (15) | 4:1 | −25/3 |
| 4b | Stage 2 | — | — | 240 | 75 (R) | ether (0.47) - hexane (4.7) | 0.286:1 | −25/1 |
| 5a | Stage 1 | 0.75 (350) | 1.5 (129) | — | — | ether (1) - hexane (10) | 2:1 | −25/3 |
| 5b | Stage 2 | — | — | 258 | 76 (R) | ether (0.51) - hexane (5.1) | 0.43:1 | −25/1 |
| 6a | Stage 1 | 0.75 (350) | 1.5 (129) | — | — | ether (1) - hexane (10) | 4:1 | −25/3 |
| 6b | Stage 2 | — | — | 278 | 87 (R) | ether (0.55) - hexane (5.5) | 0.414:1 | −25/1 |

[a]Fast crystallization within 1 minute at room temperature was observed in the second stage; the mixture was allowed to stand at room temperature for 0.5 hour and then cooled to −250C.
[b]The crystallization product was considered as a mixture of 2: 1 HGC and host compound. Yield of 2: 1 HGC was calculated with respect to the starting host compound (For entries 5 and 6, the yield is calculated with respect to the starting guest compound taking into account that only the R-isomer or racemic CPE is capable of forming HGC with (+)-DDM).

TABLE 11

Tandem asymmetric reduction of AP with NaAl[(+)-DDM]H$_2$ - inclusion crystallization with preparative isolation of (R)-sec-alcohol

| | Conditions for reduction of AP with NaAl[(+)-DDM]H$_2$ | | | | | | | | | | |
|---|---|---|---|---|---|---|---|---|---|---|---|
| | SAH | | (+)-DDM | | Volumes of H$_2$ gas evolved, ml | | AP | | | | Conditions for crystallization of DDM-PET complex | |
| Entry | mmol | mg | mmol | mg | observed/calc | | mmol | mg | THF, ml | °C./h | Solvent (ml) | °C./days |
| 1 | 2$^a$ | — | 2$^a$ | — | — | | 1 | 120 | 5 | −20/20 | ether (2) - hexane (10) | 20→−20→20/5 |
| 2 | 2 | 108 | 2 | 932 | 95.5/89.6 | | 1 | 120 | 15 | −20/20 | ether (2) - hexane (10) | 20→−20→20/5 |
| 3 | 5 | 270 | 5 | 2330 | 227/224 | | 2.5 | 300 | 30 | −20/20 | ether (6) - hexane (30) | 20→−20→20/5 |
| 4 | 20 | 1080 | 20 | 9320 | 897/896 | | 10 | 1200 | 120 | −20/20 | ether (25) - hexane (75) | 20→−20→20/5 |

| | Products after the decomposition of DDM-PET compex | | | |
|---|---|---|---|---|
| | Sec-alcohol (PET) | | | (+)-DDM |
| Entry | mg | Yield %$^b$ | e.e., % (GC) | mg | Recovery degree, %$^c$ |
| 1 | 58 | 48 | 93 (R) | 850.5 | 91 |
| 2 | 63 | 52 | 95 (R) | 819 | 88 |
| 3 | 150 | 50 | 92 (R) | 1840 | 79 |
| 4 | 636 | 53 | 93 (R) | 8574 | 92 |

$^a$2 mmol of solid NaAl[(+)-DDM]H$_2$-THF (powder) was used in this run.
$^b$For isolated sec-alcohol with respect to the starting AP, yields of PET included into HGC isolated (before its thermal decomposition) is ca. 15% above the indicated value.
$^c$Additional amounts of DDM can be isolated from washings, the overall recovery degree of the ligand being close to quantitative

TABLE 12

Comparison of DDM-derived reducing agents based on SAH and LAH in asymmetric hydride reduction of the N-acylated imine, ADPI†

| | In situ preparation of reducing agent (room temperature) | | | | | Asymmetric reduction of ADPI | | |
|---|---|---|---|---|---|---|---|---|
| Entry | Starting M$^+$ AlH$_4$− | L* | Achrial ligand (AL) | Molar ratio (Al:L*:AL) | °C./h | Conversion of ADPI, % (HPLC) | e.e. for N-DPP-PEA, % (HPLC) | |
| 1 | M$^+$ = Na$^+$ | (−)-DDM | — | 1:1.05:0 | −20/20 | 97 | 77 (S) | |
| 2 | M$^+$ = Na$^+$ | (+)-DDM | — | 1:1.05:0 | −20/20 | 95 | 77 (R) | |
| 3 | M$^+$ = Na$^+$ | (−)-DDM | EtOH | 1:1:1 | −20/20 | 94 | 30 (S) | |
| 4 | M$^+$ = Na$^+$ | (+)-DDM | EtOH | 1:1:1 | −20/20 | 74 | 43 (R) | |
| 5 | M$^+$ = Li$^+$ | (−)-DDM | — | 1:1.05:0 | −20/20 | >99 | 30 (S) | |
| 6 | M$^+$ = Li$^+$ | (+)-DDM | — | 1:1.05:0 | −20/20 | 93 | 30 (R) | |

†0.5 mmol of M$^+$AlH$_4$, 0.167 mmol (53 mg) of ADPI (molar ratio Al:ADPI = 1:0.33) and 7 ml of THF were used in each experiment.

Example 28

Resolution of (±)-PL by Inclusion Crystallization

The host compounds were prepared as described earlier. The results are shown in Table 14. A two stage resolution of (±)-PL by inclusion crystallization with (−)-CYTOL was performed in Expts. HG-217 through HG-221. Samples of the 1:1 (−)-CYTOL*(R)-PL complex isolated in Expts. HG-217 and HG-218 were combined and used for further recrystallization in Expt. HG-220. As a result of this 2-stage resolution, a (−)-CYTOL*(R)-PL complex was isolated in which the guest compound had a 95% e.e. (R). The nature of the solvent played an important role in this procedure. For example, when a 1:5 ether-hexane solvent mixture was replaced with 1:5 THF-hexane (in the latter case the molar ratio was THF:PL>100), no CYTOL*PL complex was isolated (Exps 219 and 221). However, the presence of a small amount of THF in 1:5 ether-hexane solvent (THF:PL=1:1) did not have a pronounced effect on the results (see Exps HG-217 and HG-218).

An interesting result was obtained with the chiral diol TPED. To the knowledge of the inventor, there is no example in the literature to date regarding the use of this chiral diol as host compound for resolving racemic substrates. Initial attempts to optically resolve (±)-PL using TPED as host gave very promising results (Expts. HG-226 and HG-229). It should be noted that the stereoselectivity of HG complexation in the TPED*PL system was markedly affected by the solvent composition. For example, increasing the proportion of ether in ether-hexane solvent mixture from 1:5 to 1:3 (with the addition of THF in a 1:1 THF:PL molar ratio) resulted in an e.e. of 74% for PL included into a 1:1 (+)-TPED*(S)-PL host-guest complex. This is 17% greater than the value obtained when a 1:5 ether-hexane was used as solvent.

An important advantage of the new host TPED is that it can be prepared in two steps (esterification of mandelic acid followed by Grignard alkylation) whereas the preparation of TADDOLs from tartaric acid requires 3–4 stages.

A promising result has also been obtained with another chiral diol, DPPD (see Expt. HG-225). This compound—prepared from lactic acid and having a structure similar to that of TPED—was used earlier by Weber's research group as host for resolving a number of racemic compounds (Chirality, 1993, 5, 315). However, they did not use PL as a substrate for HG complexation with DPPD. The e.e. values attained with PL included into a 1:1 HGC, although moderate, was nevertheless the first example of a successful resolution of PL using DPPD. Further improvement of this procedure is possible because the true stoichiometry of the DPPD*PL complex appears to be 1:1, whereas the crystalline product isolated in Expt. HG-225, which has a 1:1.5 H*/G ratio, is likely to be a mixture of 1:1 HGC and the starting racemic substrate.

In Expt. HG-216, the degree of resolution of (±)-PL via HG complexation with (−)-CPT (25% e.e. (S)) was markedly greater than the value obtained in a previous experiment (18% e.e.). This was probably due to the small amount of THF present in the starting ether-hexane solution. The extent of (+)-PL resolution could probably still be improved because the solid isolated in Expt. HG-216 (H*/H=1:1.3) appears to be a mixture of 1:1 HGC and (±)-PL.

Example 29

Resolution of (±)-CPE by Inclusion Crystallization with (−)-DDM and (−)-PENTOL

One of the goals of the experiments below was to increase the CPE optical resolution using a 2-stage inclusion crystallization with (−)-DDM from ether-hexane solvent. Another goal was to investigate the effect of the nature of solvent in the HG complexation between the host DDM and guest CPE. The host compounds used were prepared as described earlier. Table 15 shows the results.

TABLE 13

Stereoselective resolution of (±)-CPE via inclusion crystallization with (+)-DDM

| | | | | Inclusion crystallization conditions | | | | | Crystalline product isolated | | e.e. for CPE |
|---|---|---|---|---|---|---|---|---|---|---|---|
| Entry | Stage | (+)-DDM (H*) mmol | (±)-CPE, mmol (mg) | 2:1 HGC e.e.of CPE included into HGC, % | Solvent, ml | Starting H*:G molar ratio in solution | °C./days | mg | Composition, H*:G (mol/mol) | Yield of 2:1 HGC, % | CPE included into HGC, % (GC) |
| 1a | Stage 1 | 3 (1400) (1400) | 12 (1033) | — | — | ether (12) - hexane (60) | 1:4 | −15/1 | 924 | 2:1 | 61 | 92 (S)[a] |
| 1b | Stage 2 | — 127 | 92 | (S) ether (0.5) - hexane (5) | 2:1 | | −15/1 | 94 | 2:1 | 68 | 100 (5)0 | |
| 1c | Stage 2 | — 127 | 92 (S) | ether (0.5) - hexane (5) | 2:1 | | −15/1 | 94 | 6:1 | 23 | 1OQ (S)0 | |
| 2a | Stage 1 | 0.75 (350) | 3 — (258) | — | ether (3) - hexane (15) | 1:4 | −15/2 | 253 | 2:1 | 66 | 90.5 (R) | |
| 2b | Stage 2 | — 160 | 90.5 (R) | ether (1) - hexane (5) | 2:1 | | −15/2 | 93 | 1:0 | — | — | |
| 3a | Stage 1 | 0.75 (350) | 3 — (258) | — | ether (3) - hexane (15) | 1:4 | −15/2 | 251 | 2:1 | 65 | 93 (R) | |
| 3b | Stage 2 | — 152.5 | 93 (R) | ether (0.95) - hexane (4.75) | 2:1 | | −15/2 | 87.5 | 1:0 | — | — | |
| 4a | Stage 1 | 0.75 (350) | 3 — (258) | — | ether (3) - hexane (15) | 1:4 | −25/2 | 261 | 2:1 | 68 | 94.5 (R) | |
| 4b | Stage 2 | — 171.5 | 94.5 (R) | ether (#.05) - hexane (5.25) | 2:1 | | −25/2 | 109.5 | 1:0 | — | — | |
| 5 | Stage 1 | 0.5 (233) | 2 — (172) | — | ether (2) - hexane (16) | 1:4 | −20/1 | 124 | 2:1 | 49 | 18 (R) | |
| 6 | Stage 1 | 0.S (233) | 2 — (172) | — | ether (2) - hexane (16) | I:4 | −20/1 | 122 | 2:1 | 48 | 11 (R) | |

TABLE 13-continued

Stereoselective resolution of (±)-CPE via inclusion crystallization with (+)-DDM

| | | Inclusion crystallization conditions | | | | | | | Crystalline product isolated | | |
|---|---|---|---|---|---|---|---|---|---|---|---|
| Entry | Stage | (+)-DDM (H*) mmol | (±)-CPE, mmol (mg) | 2:1 HGC e.e.of CPE included into HGC, % | Solvent, ml | Starting H*:G molar ratio in solution | °C./days | mg | Composition, H*:G (mol/mol) | Yield of 2:1 HGC, % | e.e. for CPE CPE included into HGC, % (GC) |
| 7 | Stage 1 | 0.5 (233) | 1 — (86) | — | ether 1:2 (2) - hexane (16) | 129 | −20/1 | 50 | 2:1 | 14 (R) | |

TABLE 14

Further attempts at resolution of (±)-PL by inclusion crystallization with a number of chiral diols

| | | Condition for HG complexation | | | | | | | Crystalline product | | |
|---|---|---|---|---|---|---|---|---|---|---|---|
| | | Host compound (H*) | Guest compound (PL) | H*/G molar | | | | | | | e.e., for PL |
| Expt. | Name | mmol (mg) | Enantiomeric composition | ratio in starting soln. | Solvent (ml) | Procedure | °C./days | Composition (NMR) | H*/G ratio NMR | Yield HGC, mg (%) | included into molar of cryst. product, % (GC) |
| HG-213 | (−)- | 0.25 (124) | rac. hexane (5) | 1:2 | ether (1)- | A | 0/1 | G | — | 10 | — |
| HG-2i4 | (−)-PENTOL | 0.25 (124) | rac. hexane (5) | 1:2 | THF (1) - | C | 20/1 | H*+G0 | i:2 | i30 | 2.5 (S) |
| HG-215 | (−)-CPT | 0.25 (123) | rac. hexane (5) | i:2 | ether (1) - | A | 0/1 | G | — | — | — |
| HG-216 | (−)#PT | 0.25 (123) | rac. hexane (5) - THF (0.04) | I:2 | ether (1) - | A | 0/1 | HGC | 1:1.3 | 90 | 25.5 (S) |
| HG-217 | (−)-CYTOL | 0.25 (127) | rac. hexane (5) | 1:2 | ether (1) - | A | 20/I | HGC | 1:i | 8S (55) | 74.5 (R) |
| HG-218 | (−)-CYTOL | 0.25 (127) | rac. hexane (5) | 1:2 | ethet (1) - | A | 20/t | HGC | i:1 | 8S (52) | 70 (R |
| HG-219 | (−)-CYTOL | 0.25 (127) | rac. hexane (5) | 1:2 | THF (1) - | A | 20/1 | H+b | — | — | — |
| HG-220 | (−)-CYTOL | 0.25 (127) | 72% e.e. (R) | 1:2 | ether (I) - hexane (5) | A | 20/1 | HGC | 1 : 1 | 79 (50) | 95 #) |
| HG-221 | (−)-CYTOL | 0.25 (i27) | 72%e.e. (R) | 1:2 | THF (I) - hexane (5) | A | 20/I | H+b | — | — | — |
| HG-222 | (−)ATM | 0.25 (i46) | rac. hexane (5) - THF (0.04) | 1:2 | C₆H₆ (1.3) | (1.3)- | A | 20/i | H+ | — | — — |
| HG-223 | (−)-FLUTOL | 0.25 (132) | rac. hexane (5) | 1:2 | ether (1) - | A | 20/1 | HGC | i:1.4 | 97 | 4 (S) |
| HG-224 | (−)-FLUTOL | 0.25 (132) | rac. hexane (5) - THF (0.04) | i:2 | ether (1.2) - | A | 20/I | H++G0 | i:2 | 153 | 3 (R) |
| HG-225 | (S)#-)-DPPD | 0.25 (57) | rac. hexane (5) | I:2 | ether (I) - | A | 20/I | HGC | 1:i.5 | 36 | 20 (S) |
| HG-226 | (R)- (+)-TPED | #.25 (73) | rac. hexane (5) | 1:2 | ether (i) - | A | −15/i | HGC | 1:i | 59 (56) | 7 (S) |
| HG-227 | (R)-(+)-TPED | 0.25 (73) | rac. | 1:2 | ether (1) - hexane (3) | A | 20/1 | HGC | 1:1 | 60 (57) | 59 (S) |

TABLE 14-continued

Further attempts at resolution of (±)-PL by inclusion crystallization with a number of chiral diols

| | | Condition for HG complexation | | | | | | Crystalline product | | | |
|---|---|---|---|---|---|---|---|---|---|---|---|
| | | Host compound | Guest compound (PL) Enantio- | H*/G molar | | | | | H*/G | Yield | e.e., for PL included into Compo- molar of cryst. |
| Expt. | Name | (H*) mmol (mg) | meric compo- sition | ratio in starting soln. | Solvent (ml) | Proce- dure | °C./days | sition (NMR) | ratio NMR | HGC, mg (%) | product, % (GC) |
| HG-228 | (R)-(+)-TPED | 0.25 (73) | rac. | 1:2 | ether (1.2) - hexane (5) - THF (0.04) | A | 20/1 | HGC | 1:1 | 57 (57) | 65 (S) |
| HG-229 | (R)-(+)-TPED | 0.25 (73) | rac. | 1:2 | ether (1) - hexane (3) - THF (0.04) | A | 20/1 | HGC | 1:1 | 56 (53) | 74 (S) |

[a]Believed to be a mixture of crystalline ligand and crystalline substrate rather than a HGC.
[b](−)-CYTOL was isolated as a 1:1 HGC with THF.

The CPE optical resolution attained in Expt. HG-230 after the first nclusion crystallization stage with (−)-DDM was markedly higher (92% e.e.) than that btained in a preceding run (75% e.e.). This could be due to the fact that Expt. HG-230 as carried out using a ten-fold increase in scale. After the second crystallization stage Expt. HG-231), the isolated 2:1 HGC contained exclusively the (S)-enantiomer of CPE 100% e.e.). Thus, extending the HG complexation procedure from a 1-stage rystallization to a 2-stage crystallization improved the enantioselectivity of the whole rocedure. Note that introducing seed crystals of the HGC into the solution led to an increased (and undesirable) crystallization of (−)-DDM along with crystallization of the HGC (Expt. HG-232).

Unexpected results were obtained using solvents other than ether-hexane in the HG- complexation between the host DDM and the guest CPE. For instance, although inclusion crystallization of CPE with DDM from 1:5 benzene-hexane afforded an HGC with the same stoichiometry (H*/G=2:1), no optical resolution of CPE was observed (Expt. HG-233, 0% e.e.) when 1:5 ether-hexane was used as solvent instead of 1:5 benzene-hexane. With 1:5 THF-hexane as solvent, (−)-DDM was the only product obtained (Expt. HG-234), i.e., no HGC was obtained. In addition, the degree of optical resolution of CPE by inclusion crystallization with PENTOL using a 1:5 THF-hexane was much less (Expt. HG-235, 46% e.e. (S)) than that in a previous experiment where a 1:5 ether-hexane was used as solvent in the HG complexation (78% e.e.).

TABLE 15

Resolution of CPE and IPG by inclusion crystallization with chiral TADDOLs

| | | | | | conditions for HGs-mplexation | | | | | crystalline product | | |
|---|---|---|---|---|---|---|---|---|---|---|---|---|
| | | Guest compound (G) | | Host compound (H*) | | G/H* molar ratio in | | | 4 conditions for HGs- mplexation e.e. for G | | | included into HGC, HGC, % |
| | | | | | | | | | | H*/G molar | Yield of HGC, mg | |
| Expt. | Name | mmol (mg) | Name | mmol (mg) | starting soln. | Solvent (ml) | Proce- dure | HGC °C./day or H* | | ratio (NMR) | (%)[a] | (GC) |
| HG-230 | CPE | 12 (127)[c,d] | (−)-DMM | 3 | 4:1 | ether (12)- | | | | | | |
| | ratio in starting Sol- vent (ml) cedure ° C./day HGC or (NMR) included into | 30 (1033) | (−)-DDM | (1400) | 4:I | hexane-t5/ (60) | | | | | | |
| | HGC H3G; | 2:I CPE | (61) — | 92 (S) (−)-DDM | (1;27;C.d | 2:I | ehthe:anr. (eo:s); | | | A −15/i HGC 2:I 94 (68) I (50)0 | | |

TABLE 15-continued

Resolution of CPE and IPG by inclusion crystallization with chiral TADDOLs

| | | | | conditions for HGs-mplexation | | | | crystalline product | | |
|---|---|---|---|---|---|---|---|---|---|---|
| | | | | G/H* | | | | 4 conditions for HGs-mplexation e.e. for G | | |
| | Guest compound (G) | | Host compound (H*) | | G/H* molar ratio in | | | H*/G molar | Yield of HGC, | included into HGC, HGC, |
| Expt. | Name | mmol (mg) | Name | mmol (mg) | starting soln. | Solvent (ml) | Proce-dure | HGC °C./day or H* | ratio (NMR) | mg (%)a | % (GC) |
|---|---|---|---|---|---|---|---|---|---|---|---|
| HG-232 ether (0.5)-HG-025 | — CPE A | 0.25 -15/I HGC 2:1 | 2#1 (−)-DDM(t27)#.d 6:I# | 100 hexane (5) 94 (23) | | (S) | | | | | |
| HG-233 (117) hexane (5) HG-025 | CPE A | 1 (86) HGC | (−)-DDM HGC | 4:I 69 (54) | C 6 H 6 (1)-0 | −1511 | | | | | |
| HG-234 (I 17) hexane (5) | CPE C | I (86) | (−)-DDM 20/I | 4:I H* | THF (1)- — | — | | | | | |
| HG-235 20/i | CPE PENTOL HGC | 1 (86) (124) 93 (70) *46 (S) | 0.25 hexane (5Y | # C | THF (1)- | 2:1 | | | | | |
| HG-236 THFb hexane (5) | IPGc (33) | 0.25 CYTOL.*(145) (73) | 0.25 (S) | 118 1:1 | >96 ether (I)- A | | | −15/1 HGC I:1 | | | |
| HG-237 A IPG+ (33) THF hexane (5) | 0.25 -15/1 CYTOL.. (36) | 0.25 HGC (145) | 2:i I:1 | | ether (1)- | 100 | | | | 86 (S) | |
| (−)-HG-238 | 0.25 tPG# (132) | i THFb | CYTOL.+ | (145) | 4:I | hexane (5) | | B 20/1 HGC 1:I | 109 | 87 (S) | |

(68)

aWith respect to the starting host compound assuming the following stoichiometty: 2: I DDM-CPE, 2: i PENTOL-CPE and I : I CYTOL-JPG.
bt : 1 HGC with THF was used for resolving IPG.
c) Taken from the 2: 1 HGC isolated in Expt. HG-230.
d) 0.25 mrno
of the complex corresponds to 0.25mmol of the host included into HGC.
e(S)-enantiorner enriched IPG (80% e.e.) was used as a substrate.
F#Racemic JPG.
gCrystals of 2: I (−)-DDM * (S)-CPE cornplex were seeded into the solution before crystallization.

Example 30

HGC Formation of (−)-CYTOL and (+)-CYTOL with S-enantiomer of IPG

The goal of this experiment was to look into the possibility of using the CYTOL*THF complex for resolving (±)-IPG using a suspension. Both CYTOL antipodes were used to form 1:1 HGC's with THF. These HGC's were then used to form ternary HGC's with (S)-IPG. The host compounds were prepared as described earlier. Table 15 on previous page shows the results.

As can be seen from Experiments HG-236 and HG-237, both starting complexes, (−)-CYTOL*THF and (+)-CYTOL*THF, are capable of forming HGC's with the S-enantiomer of IPG by inclusion crystallization from 1:5 ether-hexane. The (−)-CYTOL complex provided a higher e.e. value (Expt. HG-236 and 237;>96% e.e. versus 87% e.e.), but both (+)-CYTOL and (−)-CYTOL provided further enantiomeric enrichment of (S)-IPG. It must be noted that (−)-CYTOL*THF and (+)-CYTOL*THF gave final solid products having different stoichiometries. Also, the yield of the 1:1 (+)-CYTOL*(S)-IPG complex was only about half that of the (−)-CYTOL*(S)-IPG complex.

Optical resolution of (±)-IPG using the CYTOL*THF complex (Expt. HG-238) in a suspension was successfully performed producing an 87% e.e. (S) with a respectable 68% chemical yield. The results of Expts. HG-236 and HG-237 were in good agreement with those obtained earlier.

ACHIRAL HYDROALUMINATES DERIVED FROM SAH FOR USE IN CATALYTIC HYDRIDE REDUCTIONS

SAH (sodium aluminum hydride) modified by bulky substituents such as tert-butoxy groups can also be used as hydride donors in combination with a chiral catalyst. The experiments below were performed to examine the ability of NaAl(OBu-tert)₃H to react with the β-ketoester ECAA in THF at room temperature.

Example 31

Hydride Reduction of ECAA Using NaAl(OBu-tert)₃H

The following reactants were used: SAH (Cambrex/Zeeland, 95%), ECAA (Fluka, Lot G00789), tert-BuOH (>98%, distilled before being modified with SAH), and THF (Fluka, Lot R00859). The molar ratio of the Al:tert-BuOH:ECAA complex was 1.0:3.5:0.5. A solution of tert-BuOH (0.97 g, 13.1 mmol) in 5 ml $CH_2Cl_2$ was added dropwise with stirring to SAH (202 mg, 3.7 mmol) dissolved in 10 ml THF. The mixture was stirred for 10 minutes at room temperature and then ECAA (0.26 ml, 1.9 mmol) was introduced in one portion using a syringe. The reaction was quenched using 2 ml 90% MeOH followed by extraction of the mixture with 10 ml hexane. The extract was dried with $MgSO_4$ and evaporated. $H^1$-NMR analysis of the residue showed 93% conversion of ECAA into ECHB. A similar experiment was carried out using a 1.0:5.25:0.5 molar ratio of the Al:tert-BuOH:ECAA complex. $H^1$-NMR analysis of the products indicated an 88% conversion of ECAA into EHAA.

NaAl(OBu-tert)₃H reacted with the β-ketoester ECAA at room temperature in the 1:2 THF-$CH_2Cl_2$ solvent to yield the β-hydroxyester ECHB, the conversion values being 88–94% as determined by NMR. Although NaAl(OBu-tert)₃H can generally be used as hydride donor in further catalytic reductions of ECAA, there is a probability that a direct (noncatalytic) reaction between the hydroaluminate and β-ketoester will occur.

ASYMMETRIC HYDRIDE REDUCTION OF SUBSTRATES CONTAINING C=O AND C=N GROUPS USING NA-TADDAL-H₂

It is known that the protective diphenylphosphinyl (DPP) group in N-DPP-PEA can be easily removed from a reaction product at room temperature in HCl/MeOH for 3 hours to yield an α-phenylethylamine (PEA). Under the same conditions, the much less stable ADPI undergoes hydrolysis to yield AP and $Ph_2P(O)NH_2$ (see reaction scheme below). This makes possible a GC determination of the extent of ADPI conversion by measuring the AP/PEA ratio. Because PEA on elution showed a very broad peak in the chromatogram, acetylation of PEA was carried out prior to GC analysis. The conversion of ADPI into N-DPP-PEA can also be determined by measuring the ratio of the AP and N-Ac-PEA peak squares. The R and S enantiomers of N-Ac-PEA exhibited good optical resolution when analyzed using a p-cyclodextrin column (Supelco).

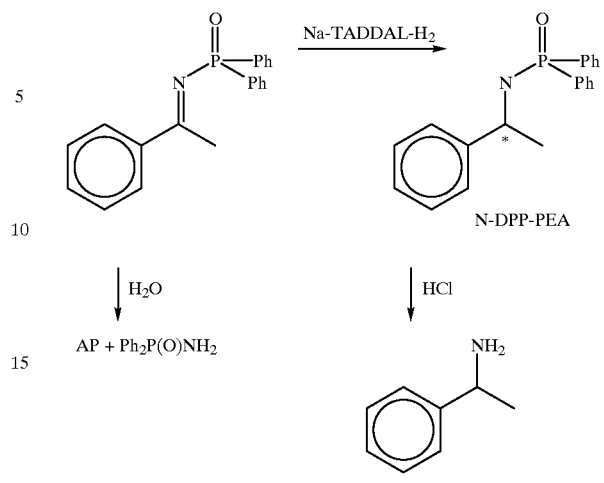

HPLC Method.

HPLC was also used to determine the ADPI conversion and the stereochemical outcome of the asymmetric reduction of ADPI with Na-TADDAL-H₂ reagents. This procedure is quite simple because the hydrolysis of N-DPP-PEA to PEA and the acetylation of PEA are excluded. Upon treatment of the reaction mixture with water after reduction (quenching the reaction), the solution turned basic. Both the non-converted imide ADPI and the amide N-DPP-PEA were found to be unhydrolyzed under these conditions.

Imide conversion can be determined via HPLC by measuring the relative intensities of the N-DPP-PEA and ADPI peaks. N-DPP-PEA showed good resolution when analyzed on a Chiralcel OD column (Daicel) using hexane-2-propanol (9:1) as mobile phase, an elution rate of 1 ml/min, and $\lambda$=254 nm. Retention times (in minutes) of the components of the reaction mixture after resolution of ADPI were as follows: 3.65, (–)-DDM; 6.64, (R)-N-DPP-PEA; 8, ADPI; and 8.56, (S)-N-DPP-PEA.

To determine the configuration (R or S) of the enantiomers of N-DPP-PEA using HPLC, optically pure (S)- and (R)-amides were prepared by acetylation with $Ph_2P(O)Cl$ of both (S)-PEA and (R)-PEA respectively.

Example 32

Asymmetric Reduction of ADPI with NaAl[(–)-DDM]H₂ and NaAl[(–)-PENTOL]H₂

(–)-DDM, (–)-PENTOL, and ADPI were prepared as described earlier. Procedure A (preparation of Na-TADDAL-H₂ in situ from SAH and TADDOL) was used in the hydride reduction of ADPI. After the reduction step, either Procedure A-1 or Procedure A-2 was used depending on the analytical method (GC or HPLC) chosen to determine both the degree of ADPI conversion and the stereochemical outcome of the reaction.

Procedure A-1

The reaction was quenched by adding 1.5 ml of HCl prepared by diluting to 1:10 a 36% HCl solution with MeOH. The acidic mixture (pH 1–2) was then stirred at room temperature for 3 hours and made alkaline (pH 10–11) with addition of 2–3 ml NaOH-saturated MeOH. The mixture was then extracted with ether (2×5 ml), and the ether extract washed with water (2×5 ml) and then dried with $Na_2SO_4$. The solution was evaporated and the PEA-containing residue was mixed with $Ac_2O$ in the presence of pyridine. The resulting mixture containing both AP and N-Ac-PEA enantiomers was analyzed by GC.

Procedure A-2

The reaction was quenched by adding 0.4 ml $H_2O$ followed by extraction of the reaction mixture with 5 ml ethyl acetate. The extract containing R- and S-enantiomers of N-DPP-PEA and $Ph_2P(O)NH_2$ (due to hydrolysis of unconverted ADPI) was analyzed by HPLC.

chiral auxiliary. As mentioned earlier, the formation of the 2:1 PENTOL*PET host-guest complex has been found to be favorable in THF.

PENTOL was also successfully used in the tandem reduction-HG complexation of PEP. In a preliminary experiment, considerable enantiomeric enrichment of PEP

TABLE 16

Asymmetric hydride reduction of the protected imine ADPI using Na-TADDAL-$H_2$

| | Preparation of Na-TADDAL-$H_2$ | | | | | Asymmetric hydride reduction of ADPI | | | | | |
|---|---|---|---|---|---|---|---|---|---|---|---|
| Exp | SAH, mmol (mg) | TADDOL Name | mmol (mg) | THE (ml) | Vol. of $H_2$ gas evolved, ml observed/calc | ADPI, mmol (mg) | Al: ADPI molar ratio | °C./ h | conv. of ADPI, %* | Analyzed product | Analytical method | e.e., % |
| (−)-DDM-94 | 0.5 (27) | (−)-DDM | 0.525 (245) | 7 | 23.9/23.5 | 0.167 (53) | 3:1 | — 70/20 | 39 | N-Ac-α-PEA | GC | 78 (S) |
| (−)-DDM-95 | 0.5 (27) | (−)-DDM | 0.525 (245) | 7 | 24.5/23.5 | 0.167 (53) | 3:1 | — 20/20 | 100 | N-Ac-α PEA | GC | 68 (S) |
| (−)-DDM-96 | 0.5 (27) | (−)-DDM | 0.525 (245) | 7 | 26.4/23.5 | 0.167 (53) | 3:1 | — 20/20 | 97 | N-DPP-α PEA | HPLC | 77 (S) |
| (−)-DDM-97 | 0.5 (27) | (−)-DDM | 0.525 (245) | 7 | 24.5/23.5 | 0.167 (53) | 3:1 | 20/20 | 98 | N-Ac-α PEA | GC | 58 (S) |
| (−)-PENTOL-8 | 0.5 (27) | (−)-PENTOL | 0.525 (260) | 7 | 23.9/23.5 | 0.167 (53) | 3:1 | — 70/20 | 51 | N-Ac-α-PEA | GC | 78 (S) |
| (−)-PENTOL-9 | 0.5 (27) | (−)-PENTOL | 0.525 (260) | 7 | 26.4/23.5 | 0.167 (53) | 3:1 | −20/20 | >95 | N-DPP-α-PEA | HPLC | 62 (S) |
| (−)-PENTOL-10 | 0.5 (27) | (−)-PENTOL | 0.525 (260) | 7 | 23.9/23.5 | 0.167 (53) | 3:1 | 20/20 | 96 | N-Ac-α-PEA | GC | 71 (S) |

*Determined by GC or HPLC depending on the procedure used to treat the reaction mixture.

The results summarized in Table 16 represent the first example of stereoselective asymmetric reduction on a C=N prochiral group using TADDOL-derived hydroaluminates. As can be seen from the table, the reaction between the protected imine ADPI and the Na-TADDAL-$H_2$ reducing agents produced not only high stereochemical yields (70–80% e.e.) but also high conversion values (up to 100%). Also noteworthy is that the GC and HPLC analyses of two PEA derivatives (N-Ac-PEA and N-DPP-PEA) showed similar results.

From Table 16, it can be also be seen that the degree of ADPI conversion diminished markedly upon lowering the reaction temperature from −20 to −70° C. In contrast, the e.e. values were not much affected by the reaction temperature although the e.e. values were slightly higher at −70° C. A similar temperature effect was earlier noted in the reaction between various ketones and the hydroaluminates NaAl(DDM)$H_2$ and NaAl(PENTOL)$H_2$. Furthermore, both reducing agents NaAl(DDM)$H_2$ and NaAl(PENTOL)$H_2$ showed similar behavior in the hydride reducion of ADPI.

Example 33

Stereoselective Tandem Reduction-HG Complexation Using (−)-PENTOL as a Chiral Auxiliary In the experiments below, 2:1 HGC's of (−)-PENTOL with PET and PEP were isolated and their yields from the tandem reduction-complexation procedure were measured. PENTOL is of particular interest in tandem hydride reduction-HG-guest complexation because like DDM, it is capable of forming HGC's with α-arylalkanols such as PET and PEP. But PENTOL does not form an HGC with THF— and this is an advantage: THF can be used in both the reduction and HG complexation stages using PENTOL as a in the second stage of the tandem reduction-complexation was achieved (from 60% e.e. to 92% e.e. (S)).

(−)-PENTOL was prepared as described earlier. Procedure A (involving the in situ preparation of NaAl[(−)-PENTOL]$H_2$) was used in the first stage of the experiment. After reducing the ketone and quenching the reaction mixture with aqueous MeOH solution, the Al-containing precipitate was separated from the solution. The solution was then evaporated off to a volume of 1 ml followed by addition of 5 ml hexane. The resulting solution was placed in a loosely stoppered flask to allow almost all of the solvent to gradually evaporate at room temperature. The crystals that formed were collected, washed with 2 ml hexane, and dried in vacuo (1–2 torr, 20→50° C.).

Further enantiomeric enrichment of α-arylalkanols was obtained by asymmetric reduction of the ketones (first stage) followed by isolation of the alkanols in the form of HGC's with (−)-PENTOL as host (second stage). Between 81–95% e.e.'s of the S-isomer were obtained when PP was used as starting substrate. These results are in good agreement with earlier experiments.

It should be noted that the ligand/host DDM was previously found to be more effective in obtaining chiral PET from AP than in obtaining chiral PEP from PP. In contrast, PENTOL appears to be the more appropriate chiral auxiliary for preparing chiral PEP from PP using the same procedure. In this regard, both the ligands/hosts DDM (for obtaining chiral PET) and PENTOL (for obtaining PEP) complement each other.

Example 34

Synthesized (−)-DDM and (+)-DDM as Chiral Auxilliaries in PP Reduction

As mentioned earlier, it would be interesting to evaluate both ligands (+)-DDM and (−)-DDM as chiral auxiliaries in asymmetric hydride reduction using modified SAH. With this in mind, PP was reacted with NaAl(DDM)H$_2$ in the experiments below. The NMR, polarimetric data, and melting points of the synthesized (−)-DDM and (+)-DDM ligands used in the experiments below agreed with those found in the literature. An in situ method (Procedure A) of preparing the reducing agent NaAl(DDM)H$_2$ was used. Table 18 shows the results.

stoppered flask to allow the solvent to evaporate gradually at room temperature. After two weeks, the crystals that formed were filtered off, washed with 2 ml hexane, and dried in vacuo (1–2 torr, 20→50° C.) to give 110.6 mg of the 2:1 (−)-PENTOL*PEP complex (79% yield with respect to the starting host compound). GC analysis showed 84% e.e. of the R-isomer of PEP included into the isolated HGC. These results are similar to those obtained in the resolution of PET

TABLE 17

Stereoselective conversion of AP and PP into chiral cL-arylalkanols with NaAl[(−)-PENTOL]H$_2$ using the tandem reduction-HG-complexation process.

| Exp[1] | Ketone | Stage | Solvent | ° C./h | Conversion of ketone into α-aryl-alkanol, % (GC) | Product Name | Yield, % | e.e., % (GC) |
|---|---|---|---|---|---|---|---|---|
| (−)-PENTOL-11 | AP | 1 (reduction) | THF | −70/20, then −70 → 20 (1 h) | 61 | PET | — | 77 (S) |
| | | 2 (HG complexation) | 1:5 THF-hexane | 20/7 days | — | PET | 36 (60) | 84 (S) |
| (−)-PENTOL-12 | PP | 1 (reduction) | THF | −70/20, then −70 → 20 (1 h) | 62 | PEP | — | 81 (S) |
| | | 2 (HG complexa-tion) | 1:5 THF-hexane | 20/7 days | — | PEP | 41 (66) | 95 (S) |

*Yields of α-aryalkanol relative to the converted ketone are given in parentheses.

The synthesized DDM ligands (used in the experiments above as chiral auxiliaries in the hydride reduction of PP) gave results which agreed well with those obtained using DDM from Aldrich/Fluka. Both (−)-DDM and (+)-DDM gave very high chemical yields and good e.e. values. Based on the above results, both DDM isomers are effective chiral reagents in the hydride reduction of PP.

using (−)-PENTOL under similar conditions. In both experiments, only the 2:1 HGC's were obtained, i.e., no co-crystallization of PENTOL with the HGC occurred. Interestingly, both the 2:1 (−)-PENTOL*PET and 2:1 (−)-PENTOL*PEP complexes that were isolated contained a predominance of the R-enantiomer of the corresponding alcohol, whereas the HGC's obtained after a tandem

TABLE 18

Reduction of PP with NaAl(DDM)H$_2$ using the ligands, produced by Tula plant.

| | Preparation of NaAl(DDM)H$_2$ | | | | | Reduction of PP to PEP | | | | |
|---|---|---|---|---|---|---|---|---|---|---|
| | SAH | TADDOL | | | Volume of H$_2$ gas evolved, | PP, | Al:PP | | Conversion of PP. | e.e., |
| Exp. | mmol (mg) | Name | mmol (mg) | THF (ml) | ml observed/calc | mmol (mg) | molar ratio | ° C./h | % (GC) | % (GC) |
| (−)-DDM-98 | 0.5 (27) | (−)-DDM | 0.525 (245) | 7 | 24.8/23.5 | 0.25 (33.5) | 1:2 | −70/20 | 99 | 81 (S) |
| (−)-DDM-99 | 0.5 (27) | (−)-DDM | 0.525 (245) | 7 | 24.8/23.5 | 0.25 (33.5) | 1:2 | −70/20 | 97 | 73 (S) |
| (+)-DDM-130 | 0.5 (27) | (+)-DDM | 0.525 (245) | 7 | 24.8/23.5 | 0.25 (33.5) | 1:2 | −70/20 | 100 | 84 (R) |
| (+)-DDM-131 | 0.5 (27) | (+)-DDM | 0.525 (245) | 7 | 24.8/23.5 | 0.25 (33.5) | 1:2 | −70/20 | 100 | 89 (R) |

Example 35

Resolution of (±)-PEP by HG Complexation with (−)-PENTOL (−)-PENTOL (124 mg, 0.25 mmol) and PEP (137 μL, 1 mmol) were dissolved in 1 ml THF followed by addition of 5 ml hexane. The solution was then placed in a loosely reduction-HG complexation contained S-enantiomer-enriched PET and PEP. Thus, whether an R-isomer and S-isomer of PEP or PET is obtained with PENTOL as host depends on whether a direct HG complexation was performed or whether a tandem reduction-HG complexation was performed.

Example 36

(±)-PL Resolution Via HG Complexation with the 1,2-diol (R)-TPED. The Effect of THF as Co-solvent The use of THF as co-solvent was favourable in the HG complexation of DDM*PET and PENTOL*PET pairs. In contrast, the use of small amounts of THF (THF:PL=1:1) in HG complexation using CYTOL as host and PL as guest gave poor results. In the presence of excess THF (THF:PL>100), the only crystalline product isolated was the 1:1 CYTOL*THF complex. Based on these findings, the effect of THF on the optical resolution of PL using the host (R)-TPED was investigated through experiments similar to those performed previously.

TABLE 19

Effect of THF as co-solvent on the degree of resolution of (±)-PL by inclusion crystallization with (R)-TPED

| | | | | Crystalline HGC | | |
|---|---|---|---|---|---|---|
| Entry | Experiment | Solvent (ml) | H*/G molar ratio (NMR) | Yield of HGC mg | % | e.e. of PL included into HGC, % (GC) |
| 1 | HG-226 | ether (1) - hexane (5) | 1:1 | 59 | 56 | 57 (S) |
| 2 | HG-247 | ether (1) - hexane (5) | 1:1 | 62 | 59 | 61 (S) |
| 3 | HG-247 | ether (1) - hexane (3) | 1:1 | 60 | 57 | 59 (S) |
| 4 | HG-248 | ether (1) - hexane (3) | 1:1 | 60 | 57 | 69 (S) |
| 5 | HG-228 | ether (1) - hexane (5) - THF (0.04)[b] | 1:1 | 57 | 57 | 65 (S) |
| 6 | HG249 | ether (1) - hexane (5) - THF (0.04)[b] | 1:1 | 58 | 55 | 71 (S) |
| 7 | HG-229 | ether (1) - hexane (3) - THF (0.04)[b] | 1:1 | 56 | 53 | 74 (S) |
| 8 | HG250 | ether (1) - hexane (3) - THF (0.04)[b] | 1:1 | 55 | 52 | 71 (S) |
| 9 | HG-251 | THF (0.5) - hexane (10) | 1:1 | 37 | 35 | 80 (S) |

[a]0.25 mmol (127 mg) of (R)-TPED and 0.5 mmol (65 mg) of (±)-PL were used in each experiment. Crystallization of HGC was performed from a solution placed in a stoppered flask between 25–30° C. for 24 hours.
[b]0.04 ml of THF corresponds to a 1:1 THF:PL molar ratio.

As can be seen from results summarized in Table 19, the stereoselectivity of HG complexation between the host (R)-TPED and guest PL ranged from 57% to 69% (S) when a 1:5 or a 1:3 ether-hexane solvents was used (Entries 1–4). However, adding a small amount of THF (1:1 THF:PL) to both ether-hexane solvent compositions produced distinctly higher e.e. values (65–75%) for (S)-PL included into a 1:1 HGC (Entries 5–8). Moreover, when a 1:20 THF-hexane solvent was used, the stereochemical yield of HG complexation went up to as high as 80% e.e. (Entry 9).

In contrast to CYTOL, TPED does not form an HGC with THF as shown by the absence of THF in the 1:1 HGC isolated in Expt. HG-251. This advantage allows the use of THF-containing solvent mixtures in experiments using (R)-TPED as host compound. A high level of reproducibility was observed in experiments involving the host (R)-TPED and guest PL. This suggests a strong affinity between (R)-TPED and PL which explains the favorable optical resolution of the latter. Based on the above results, (R)-TPED can be considered the best chiral diol host for optically resolving (±)-PL.

Example 37

Resolution of PL, CPE and IPG by HG Complexation with Chiral Diols Other Than (R)-TPED. Effect of Solvent Nature Both the ability of the host (−)-CPT to form an HGC with PL and the corresponding stereochemical yield proved to be strongly influenced by the composition of the solvent ether-hexane (Expts. HG-252–HG-255). For instance, with a 1:5 ether-hexane as solvent, racemic PL was the only solid product isolated from a solution containing both PL and (−)-CPT (Expt. HG-252). But when a 1:4 ether-hexane solvent was used, a crystalline (−)-CPT*PL complex having a true 1:1 stoichiomery was isolated from the solution (see Expts. HG-253 and HG-254). The (−)-CPT*PL complex obtained had a 55% e.e. (S). A further increase in the ether-hexane volume ratio to 1:3 gave a very poor resolution of PL under an otherwise identical conditions ((Expt. HG-255).

On the other hand, the use of (−)-PENTOL as host in the optical resolution of (±)-PL did not yield promising results (Exps HG-256–HG-258), a behavior also exhibited by the ligand DDM towards (±)-PL.

The poor result obtained from the HG complexation between PL and (−)-CYTOL in benzene-hexane (see Expts. HG-259 and HG-260) was likely caused by the low proportion of benzene used in the solvent mixture. The benzene-hexane ratio should probably be increased to obtain better optical resolution of PL. As can be seen from data obtained in Experiments HG-261 and HG-262, the 1,2-diol (S)-DPPD appears less effective than its structural analog (R)-TPED in forming an HGC with PL (see Table 20).

Comparison of results obtained in Experiments HG-233 and HG-263 shows that the true stoichiometry of the DDM*CPE host-guest complex isolated from benzene-hexane is actually 2:1. However, attempts to resolve CPE via HG complexation of this substrate with (−)-DDM as host yielded very poor or no resolution in benzene-hexane as previously observed. Surprisingly, changing the solvent composition from 1:5 ether-hexane to 1:5 benzene-hexane led to a significant decrease in stereoselectivity from 92% e.e. in 1:5 ether-hexane to 0–10% e.e. in 1:5 benzene-hexane.

Data obtained in Experiment HG-264 confirmed the result of the preceding Experiment HG-238 in which the ligand-solvent complex CYTOL*THF, in contrast to CYTOL alone, successfully resolved (±)-IPG using a suspension technique. In this procedure, the substrate (±)-IPG takes the place of THF during the course of HG complexation to form the (±)-IPG*CYTOL complex.

Example 38

Enantioselective Reduction of N-Diphenylphosphinylimide ADPI with SAH Modified by Various TADDOLs Asymmetric reduction of ADPI with (−)-DDM and (−)-PENTOL-based sodium dihydroaluminates were earlier shown to proceed stereoselectively, the e.e. values being as high as 78%. The goal of the experiments below was to continue the investigation of asymmetric reduction of protected imine using chiral ligands other than (−)-DDM and (−)-PENTOL. The TADDOLs used in the experiment were prepared as described earlier.

Procedure A was used in preparing Na-TADDAL-H$_2$ in situ from SAH and TADDOL. The reaction was quenched by adding 0.4 ml H$_2$O followed by extraction of the reaction mixture with 5 ml ethyl acetate. The extracts containing the R and S enantiomers of N-DPP-PEA (in addition to unconverted ADPI) was analyzed by HPLC.

The use of various TADDOLs in the reaction with protected imine (ADPI) afforded 95–100% substrate conversion with stereoselectivities that differed only slightly (75–77% e.e.). These results were observed both at −20° C. and −70° C. Thus, it appears that the reaction temperature exerts little effect on the outcome of ADPI reduction using Na-TADDAL-H$_2$. The temperature appears to have an even smaller effect on the reduction of protected imine using Na-TADDAL-H$_2$ compared to its effect on the reduction of ketones using the same reducing agents.

TABLE 20

Resolution of PL, CPE and IPG by HG complexation using chiral diols other than (R)-TPED

| | | | | | | | | | | | |
|---|---|---|---|---|---|---|---|---|---|---|---|
| | Conditions for HG complexation | | | | | | | Crystalline product | | | |
| | Guest Compound | | Host compound | | G/H* molar ratio in starting | | Proce- | | H*/G molar ratio | Yield of HGC | e.e. of G included into HGC, |
| Expt. | Name | mmol (mg) | Name | mmol (mg) | solution | Solvent (ml) | dure | ° C./days | (NMR) | mg / % | (%) (GC) |
| HG-252 | PL | 0.5 (65) | (−)-CPT | 0.25 (123) | 2:1 | ether (1) - hexane (5) | A | 0/2, then −15/1 | 0:1 | 30 — | — |
| HG-253 | PL | 0.5 (65) | (−)-CPT | 0.25 (123) | 2:1 | ether (1) - hexane (4) | A | 0/2 | 1:1 | 79  51 | 54 (S) |
| HG-254 | PL | 0.5 (65) | (−)-CPT | 0.25 (123) | 2:1 | ether (1) - hexane (4) | A | 0/2 | 1:1 | 78  50 | 56 (S) |
| HG-255 | PL | 0.5 (65) | (−)-CPT | 0.25 (123) | 2:1 | ether (1) - hexane (3) | A | 0/2 | 1:1.3 | 114 — | 6 (S) |
| HG-256 | PL | 0.5 (65) | (−)-PENTOL | 0.25 (124) | 2:1 | THF (0.5) - hexane (5) | A | 20/1, then 0/2 | —[a] | — — | — |
| HG-257 | PL | 0.5 (65) | (−)-PENTOL | 0.25 (124) | 2:1 | THF (0.5) - hexane (5) | A | 20/1 then 0/2 | —[a] | — — | — |
| HG-258 | PL | 0.5 (65) | (−)-PENTOL | 0.25 (124) | 2:1 | THF (0.5) - hexane 910) | A | 20/1, then 0/2 | 1:2 | 62 — | 8 (S) |
| HG-259 | PL | 1 (130) | (−)-CYTOL | 0.5 (253) | 2:1 | ether (2) - hexane (10) | A | 20/2 | 1:1 | 187  59 | 68 (R) |
| HG-260 | PL | 0.5 (65) | (−)-CYTOL | 0.25 (126) | 2:1 | benzene (0.5) - hexane (5) | A | 20/2 | 1:1.7 | 139 — | 25 (R) |
| HG-261 | PL | 0.5 (65) | (S)-DDDP | 0.25 (57) | 2:1 | ether (0.5) - hexane (5) | A | 20/1, then 0/2 | —[a] | — — | — |
| HG-262 | PL | 0.5 (65) | (S)-DDDP | 0.25 (57) | 2:1 | ether (0.5) - hexane (10) | A | 20/1, then 0/2 | 1:2 | 66 — | 27 (R) |
| HG-233 | CPE | 1 (86) | (−)-DDM | 0.25 (117) | 4:1 | benzene (1) - hexane (5) | A | −15/1 | 2:1 | 69  54 | 0 |
| HG-263 | CPE | 1 (86) | (−)-DDM | 0.25 (117) | 4:1 | benzene (0.5) - hexane (5) | A | −15/1 | 2:1 | 88  69 | 11 (S) |
| HG-238 | IPG | 1 (132) | (−)-CYTOL · THF | 0.25 (145) | 4:1 | hexane 5 | B | 20/1 | 1:1 | 109  68 | 87 (S) |
| HG-264 | IPG | 1 (132) | (−)-CYTOL · THF | 0.25 (145) | 4:1 | hexane 5 | B | 20/3 | 1:1 | 108  68 | 81 (S) |

[a]No crystallization was observed

TABLE 21

Enantioselective reduction of N-diphenylphosphinyl imide ADPI
to N-DPP-PEA using SAH modified with various TADDOLs[a]

| | In situ preparation of NaAl(L*)H$_2$ | | | | | Asymmetric reduction of ADPI | |
|---|---|---|---|---|---|---|---|
| | L* | | Molar ratio | Volume of H$_2$, gas evolved, ml, | | Conversion of ADPI, % | e.e. for N-DPP-PEA, % |
| Expt. | Name | mmol (mg) | Al:L*:ADPI | found/calcd | °C/h | (HPLC) | (HPLC) |
| (−)-DDM-96 | (−)-DDM | 0.525 (245) | 1:1.05:0.33 | 26.4/23.5 | −20/20 | 97 | 77 (S)[b] |
| (+)-DDM 132 | (+)-DDM | 0.525 (245) | 1:1.05:0.33 | 24.9/23.5 | −70/20 | 98 | 77 (R) |
| (+)-DDM 133 | (+)-DDM | 0.525 (245) | 1:1.05:0.33 | 24.9/23.5 | −20/20 | 95 | 77 (R) |
| PENTOL-9 | (−)-PENTOL | 0.525 (260) | 1:1.05:0.33 | 24.4/23.5 | −20/20 | >90 | 62($_S$)b |
| (−)-CPT-23 | (−)-CPT | 0.525 (258) | 1:1.05:0.33 | 24.9/23.5 | −70/20 | 100 | 33 (S) |
| (−)-CPT-246 | (−)-CPT | 0.525 (258) | 1:1.05:0.33 | 24.9/23.5 | −20/20 | 100 | 75 (S) |
| (−)-CYTOL 44 | (−)-CYTOL | 0.525 (265) | 1:1.05:0.33 | 26.7/23.5 | −70/20 | 2 | 77 (S) |
| (−)-CYTOL 45 | (−)-CYTOL | 0.525 (265) | 1:1.05:0.33 | 26.7/23.5 | −20/20 | 100 | 40 (S) |
| (−)-FLUTOL-9 | (−)-FLUTOL | 0.525 (309) | 1:1.05:0.33 | 23.1/23.5 | −70/20 | 100 | 66 (S) |
| (−)-FLUTOL-10 | (−)-FLUTOL | 0.525 (309) | 1:1.05:0.33 | 23.1/23.5 | −20/20 | 100 | 69 (S) |
| (−)-ITM-12 | (−)-ITM | 0.525 (308) | 1:1.05:0.33 | 24.0/23.5 | −70/20 | 100 | 50 (5) |
| (−)-ITM-13 | (−)-ITM | 0.525 (308) | 1:1.05:0.33 | 24.9/23.5 | −20/20 | 100 | 76 (S) |

[a]All experiments were carried out using 0.5 mmol (27 mg) SAH, 0.167 mmol (53 mg) ADPI and 7 ml of THF.

Example 39

Further Investigation of Optical Resolution of PL Using (R)-TPED as Host

As the results of Expt. HG-251 show, THF-hexane may be used as solvent in place of ether-hexane for effective optical resolution of (±)-PL using (R)-TPED because THF does not form an HGC with (R)-TPED. The results of HG complexation between the host (R)-TPED and the guest PL using THF-hexane and benzene-hexane as solvents are discussed below. Procedure A (crystallization from a solution in a stoppered flask) was used in the experiments. Use of 1:10 THF-hexane as solvent in the optical resolution of (±)-PL with the host (R)-TPED proved to be somewhat preferable than 1:20 THF-hexane (see Expts. HG-269–HG-271 and Expts. HG-256–HG-267 in Table 20). With 1:10 THF-hexane as solvent, an e.e. of as high as 89% was achieved after the first resolution stage.

TABLE 22

Resolution of (±)-PL (G) by inclusion crystallization
with (R)-TPED (H*) in various solvents

| Expt. | G/H*[a] molar ratio in a start. soln. | Solvent (ml) | °C./days | H*/G ratio. | Yield of HGC mg | % | e.e. of PL included into HGC, % (GC) |
|---|---|---|---|---|---|---|---|
| HG-265 | 2:1 | THF (0.5) - hexane (5) | 3 | 1:1 | 53 | 50 | 75 (S) |
| HG-266 | 2:1 | THF (0.75) - hexane (7.5) | +3/1, then −25 (1 h), then +3/1 | 1:1 | 30 | 29 | 89 (S) |
| HG-267 | 2:1 | THF (1) - hexane | +3/1, then −25 (1 h), | 1:1 | 24 | 23 | 89 (S) |
| HG-251 | 2:1 | THF (0.5) - hexane (10) | then +3/1 25-30/1 | 1:1 | 37 | 35 | 80 (S) |
| HG-268 | 2:1 | THF (0.5) - hexane (10) | 25/1 | 1:1 | 30 | 28 | 73 (S) |
| HG-269 | 2:1 | THF (0.5) - hexane (10) | 3 | 1:1 | 50 | 48 | 57 (S) |
| HG-270 | 2:1 | THF (0.75) - hexane (15) | 3 | 1:1 | 38 | 36 | 57 (S) |
| HG-271 | 2:1 | THF (1) - hexane (20) | 3 | 1:1 | 18 | 17 | 83 (S) |
| HG-272 | 2:1 | ether (2) - hexane (4) | 3 | 1:1 | 29 | 27 | 86 (S) |
| HG-273 | 2:1 | C$_6$H$_6$(1) - hexane (5) | 25/1 | 1:1 | 80 | 76 | 60 (S) |
| HG-274 | 2:1 | C$_6$H$_6$ (1) - hexane (5) | 25/1 | 1:1 | 80 | 76 | 60 (S) |

[a]All experiments were carried out using 0.25 mmol (72.6 mg) (R)-TPED and 0.5 mmol (65 mg) (±)-PL following Procedure A.
[b]Most of the HGC crystals precipitated within 3 minutes.

As can be seen from the results of Expts. HG-265–HG-267 and Expts. HG-269–HG-271 in Table 20, lowering the reagent concentrations led to an improvement in PL stereoselectivity. However, lower HGC yields were obtained in the more dilute solutions. A high PL resolution of 86% e.e. was attained using a 1:2 ether-hexane as solvent (Expt. HG-272), although this is not much different from the result obtained using THF-hexane as solvent (83% e.e. (S); Expt. HG-271).

Although the HG complexation of (R)-TPED with PL in 1:5 benzene-hexane produced a good chemical yield of 1:1 HGC (76%), the optical resolution of PL was markedly lower (60% e.e.) than that obtained when THF-hexane or ether-hexane was used as solvent. This could be due to the rapid crystallization of HGC (from benzene-hexane) which occurred within approximately less than 3 minutes at room temperature.

CATALYTIC VERSION OF ASYMMETRIC HYDRIDE REDUCTION USING VITRIDE® AS A REDUCING AGENT

The possibility of using $NaAl(O\text{-tert-Bu})_3H$ as hydride donor in a non-catalytic reaction with the β-ketoester ECAA has been investigated previously. Unfortunately, $NaAl(O\text{-tert-Bu})_3H$ was found to react vigorously with ECAA (for 10 minutes at room temperature to produce the hydroxyester ECHB with a 93% ECAA conversion). This high reactivity of $NaAl(O\text{-tert-Bu})_3H$ is undesirable in the direct (non-catalytic) reduction of C=O group and also prevents NaAl (O-tert-Bu)$_3$H from being used as hydride donor in the catalytic reduction of ketones. Therefore, there is a need to find SAH-based reducing agents that are much less active in reducing the C=O group in the absence of a catalyst.

Below, the use of Vitride® (as hydride donor in the catalytic reduction of AP), 15-crown-S, and TEBA as modifying reagents is discussed. It is postulated by many researchers that adding a crown-ether to lithium (or sodium) tetrahydroaluminate or its derivatives keeps the lithium (or the sodium) cation from activating the C=O group and thus prevents a stoichiometric hydride reduction of ketones.

Similarly, it is believed that the exchange reaction between TEBA and a $NaAl(L)_2H_2$ such as Vitride® to yield $[Et_3NCH_2Ph]^+Al(L)_2H_2$ also prevents hydride reduction of ketones because the tetrahydroalkylammonium cation, like $M^+(15\text{-crown-5})$, is incapable of activating the C=O group of the substrate.

Earlier, the inventor found that when AP is reduced by $NaAl(DDM)H_2$ in THF at −20° C., the AP conversion drops dramatically when the crown-ether/Al molar ratio is increased from 1:1 to 2–3:1. The decrease in conversion could be due to the quenching of the reaction by water which was not completely removed from the "anhydrous" crown-ether even after careful drying. The inventor therefore reinvestigated the role of crown-ether in the conversion of AP using Vitride® in place of DDM in the reducing agent.

Example 40

Reduction of AP with $NaAl(OCH_2CH_2OCH_3)_2H_2$ (Vitride®) in the Presence of 15-crown-5 or Triethylbenzylammonium Chloride (TEBA)

Procedure A:

A solution of SAH in THF was added to 2-methoxyethanol (MET) also dissolved in THF, followed by addition of the crown-ether or TEBA. The volume of $H_2$ gas evolved was then measured. To the reaction mixture thus obtained was added AP while stirring for 1 hour at 20° C. or for 2 hours at −20° C. Afterwards, the reaction was quenched using 90% MeOH.

Procedure B:

The crown-ether and a solution of SAH in THF were added successively to a solution of MET in THF. A procedure similar to that described in Procedure A above was then performed.

As can be seen from results summarized in Table 23, the volume of $H_2$ gas evolved after adding both 2-methoxyethanol and 15-crown-5 to SAH was significantly larger than the calculated value, the difference between the observed and calculated values growing with an increase in the crown-ether/Al ratio. This suggests that the

TABLE 23

Reduction of AP with $NaAl(OCH_2CH_2OCH_3)_2H_2$ (Vitride ® ) in the presence of 1 5-crown-5 or triethylbenzylammonium chloride (TEBA)*

| | | | In situ preparation of dihydride complex | | Reduction of AP | | | |
|---|---|---|---|---|---|---|---|---|
| | | | vol. of $H_2$ evolved after addn. of L and AC, ml, | Exposure of the complex prior to use in the reaction with | Molar ratio Al:L:AC: | | vol. $H_2$ gas evolved after the reaction quenching, mL, | Conversion of AP, % |
| Entry | Additional compound | | | | | | | |
| | Name | mmol (MG) | obser/calc. | AP, 0° C./h | AP | ° C./h | obser/calc | (GC) |
| 1 | 15-crown-5 | 0.5 (110) | 34.5/22.4 | 20/0.5 | 1:2:1:0.5 | 20/1 | 9.3/10.3 | 100 |
| 2 | 15-crown-5 | 0.5 (110) | 32.2/22.4 | 20/0.5 | 1:2:1:0.5 | 20/1 | 6.4/12.6 | 97 |
| 3 | 15-crown-5 | 1 (220) | 37.7/22.4 | 20/0.5 | 1:2:2:0.5 | 20/1 | 1.8/7.1 | 88 |
| 4 | 15-crown-5 | 1 (220) | 39.1/22.4 | 20/0.5 | 1:2:2:0.5 | 20/1 | 2.3/5.7 | 92 |
| 5 | 15-crown-5 | 0.5 (110) | 38.2/22.4 | 20/0.5 | 1:2:1:0.5 | −20/2 | 3.0/6.6 | 72 |

TABLE 23-continued

Reduction of AP with NaAl(OCH$_2$CH$_2$OCH$_3$)$_2$H$_2$ (Vitride ® ) in the presence of 1 5-crown-5 or triethylbenzylammonium chloride (TEBA)*

| | | In situ preparation of dihydride complex | | Exposure of the complex prior to use in the reaction with | | Reduction of AP | | | |
|---|---|---|---|---|---|---|---|---|---|
| En- try | Additional compound Name | mmol (MG) | vol. of H$_2$ evolved after addn. of L and AC, ml, obser/calc. | AP, 0° C./h | Molar ratio Al:L:AC: AP | ° C./h | vol. H$_2$ gas evolved after the reaction quenching, mL, obser/calc | Conver- sion of AP, % (GC) |
| 6 | 15-crown-5 | 1 (220) | 37.2/22.4 | 20/0.5 | 1:2:2:0.5 | −20/2 | 6.4/7.6 | 83 |
| 7 | iS-crown-5 | 1 (220) | 36.8/22.4 | 20/0.5 | 1:2:2:0.5 | −20/2 | 6.4/8.0 | 35 |
| 8 | 15-crown-5 | 1.5 (330) | 39.6/22.4 | 20/0.5 | 1:2:3:0.5 | 18/1 | 1/5.2 | 74 |
| 9 | 15-crown-5 | 1.5 (330) | 41.0/22.4 | 20/0.5 | 1:2:3:0.5 | −20/2 | 5.5/3.8 | 0 |
| 10 | 15-crown-5 | 1.5 (330) | 41.4/22.4 | 20/0.5 | 1:2:3:0.5 | −20/2 | 4.1/3.4 | 6 |
| 11 | 15-crown-5 | 1.5 (330) | 37.2/22.4 | 20/0.5 | 1:2:3:0.5 | — 20/20 | 7.5/7.6 | 3 |
| 12 | TEBA | 0.125 (28.5) | 30.0/22.4 | 25/0.5 | 1:2:0.25:0.5 | −20/2 | 11.8/14.8 | 96 |
| 13 | TEBA | 0.125 (28.5) | 29.1/22.4 | 25/0.5 | 1:2:0.25:0.5 | −20/1 | 9.1/6.6 | 95 |

*All experiments were carried out using 0.5 mmol (27 mg) of SAH (in 0.3–0.5 M solution of THF), 1 mmol (76 mg) of CH$_3$OCH$_2$CH$_2$OH and 0.25 mmol (30 mg) of AP following Procedure A (entries 1–6 and 9) or B (Entries 7, 8, 10, and 11).

crown-ether still retained some water even after careful drying. While it is likely that the low AP conversion values in experiments for which the Al: crown-ether ratio was 1:3 (Entries 9–11) was due to the quenching of the reaction by residual water rather than due to complexation of the crown-ether with Na, it is possible that both quenching by water and complexation with Na contributed to the observed low AP conversion. Because it was not clear exactly which factor gave rise to the observed low AP conversion (Table 23), cobalt catalysts (mainly non-modified Vitride) were used in subsequent experiments. TEBA was found to be only par- tially soluble in THF thus preventing a complete exchange of Na$^+$ by [Et$_3$NCH$_2$Ph]$^+$ in the Vitride®.

Example 41

Catalytic Reduction of AP Using Co(BSIC)$_2$ as a Catalyst and Vitride® as a hydride donor Co(BSIC)$_2$ was obtained from COCl$_2$ (Catalyst 1) and from Co(OAc)$_2$ (Catalyst 2) as described earlier (see Example 13). The 2-methoxyethanol (MET) and 15-crown-S were dried and distilled with SAH before use.

TABLE 24

Cobalt-catalyzed asymmetric reduction of AP using Vitride ® as a hydride donor*

| | Preparation of catalyst-containing reducing system | | | | | | Reduction of AP | | | |
|---|---|---|---|---|---|---|---|---|---|---|
| | Co(L*)$_2$ | | Additional component | | | | Molar ratio Al:ME:15- | | Cony. | |
| Entry | Co(B5IC)$_2$ | mmol (mg) | Name | mmol (mg) | Operation sequence Stage | ° C./h | crown 5:Co:AP | ° C./h | of AP, % (GC) | e.e., % (GC) |
| 1 | Catalyst-1 | 0034 (13) | — | — | SAH + MET + Co(L*)$_2$ | 25/0.5 | 1.2:0:0.07:0.5 | 25/24 | 82 | 0 |
| 2 | Catalyst-1 | 0.034 (13) | — | — | SAH + MET + Co(L*)$_2$ | 25/0.5 | 1:2:0:0.07:0.5 | 20/24 | 96 | 0 |
| 3 | Catalyst-2 | 0.25 (95) | — | — | SAH + Co(L*)$_2$ | 28/2 | 1:0:0:0.5:0.5 | 5/70 | 96 | 0 |
| 4 | Catalyst-2 | 0.125 (48) | — | — | SAH + Co(L*)$_2$ | 28/2 | 1:0:0:0.25:0.5 | 5/70 | 93 | 0 |

TABLE 24-continued

Cobalt-catalyzed asymmetric reduction of AP
using Vitride ® as a hydride donor*

| | Preparation of catalyst-containing reducing system | | | | | | Reduction of AP | | | |
|---|---|---|---|---|---|---|---|---|---|---|
| | Co(L*)$_2$ | | Additional component | | | | Molar ratio Al:ME:15- | | Conv. of AP, | e.e., % |
| Entry | Co(B5IC)$_2$ | mmol (mg) | Name | mmol (mg) | Operation sequence Stage | °C./h | crown 5:Co:AP | °C./h | % (GC) | (GC) |
| 5 | Catalyst-2 | 0.125 (48) | — | — | SAH + Co(L*)$_2$ + MET | 22/0.5 22/0.5 | 1:1.5:0: 0.25:0.5 | −20/22 | 74 | 0 |
| 6 | Catalyst-2 | 0.125 (48) | — | — | SAH + MET + Co(L*)2 | 22/0.5 −20/0.5 | 1:1.5:0: 0.25:0.5 | −20/22 | 86 | 0 |
| 7 | Catalyst-2 | 0.025 (10) | 15-crown-S | 1 (220) | SAH + MET + crown ether + Co(L*)2 | 20/0.5 20/05 −22/0.5 | 1:2:2:0.05: 0.5 | −20/22 | 1 ~ z0 | |

*All experiments were carried out using 0.5 mmol SAH and 7 ml THF.

Data summarized in Table 24 show that while reduction using sodium hydroaluminates in the presence of Co(BSIC)$_2$ at −20° C. in THF gave considerable conversion of AP, no stereoselectivity was observed. The high conversion is most likely due to the ability of sodium hydroaluminates to react with AP even in the presence of crown-ether at −20° C. On the other hand, the lack of stereoselectivity may be in part due to the low (if any) catalytic activity of the chiral cobalt catalyst under the conditions used.

From the results obtained, it can be concluded that ketones such as AP cannot be considered appropriate substrates in this catalytic version of asymmetric hydride reduction using sodium hydroaluminates (including Vitride®) because the latter are reactive towards the substrate even in the presence of a crown-ether. The reactivity of the hydroaluminates thus prevented the suppression of stoichiometric hydride reduction using modified SAH in the runs above.

Example 42

Catalytic Activity of OAB Complexes

OAB catalysts 1–3 were prepared as described above. A 2M solution of BH$_3$ in THF (0.5 ml, 1 mmol) was added to an OAB catalyst. To the resulting solution was added AP (60 µl, 0.5 mmol) in one portion using a syringe after which the mixture was stirred for 1 hour at room temperature, then diluted with 10 ml benzene and quenched with 3 ml KOH-saturated water. The organic layer was separated, dried with MgSO$_4$, and analyzed by GC.

Both crude IDOB (OAB catalyst-1) and the sublimated complex (OAB catalyst-2) proved to be active in asymmetric reduction of AP at room temperature in combination with BH$_3$ (Table 25, entries 1–3). For example, a 100% conversion of AP was attained with as little as 5% IDOB (entry 3). The results obtained, coupled with literature data, suggest that IDOB should be further examined as a catalyst in the reduction (using achiral hydroaluminates) of appropriate substrates such as acetophenone oxime derivatives. In contrast to OAB catalyst-1 and OAB catalyst-2, OAB catalyst-3 (the residue obtained after sublimation of IDOB) did not exhibit any activity towards asymmetric reduction (entries 4 and 5).

TABLE 25

Catalytic activity of OAB complexes derived from
(S)-AMDB with BH$_3$ (THF, room temp., 1 hour)

| Entry | Catalyst | Molar ratio BH$_3$:AP:catalyst | Conversion of AP, % (GC) | e.e., % (GC) |
|---|---|---|---|---|
| 1 | OAB catalyst-1 | 100:25:25 | 100 | 56 (R) |
| 2 | OAB catalyst-2* | 100:50:6 | 100 | 24 (R) |
| 3 | OAB catalyst-2* | 100:25:1.25 | 100 | 38 (R) |
| 4 | OAB catalyst-3 | 100:50:7 | 100 | 0 |
| 5 | OAB catalyst-3 | 100:50:13 | 100 | 0 |

*Catalysts used in these runs were prepared from different experiments.

Example 43

Asymmetric Hydride Reduction of Substrates Containing C=O and C=N Groups Using NaAl (TADDOLate)H$_2$ as Reducing Agents The TADDOLs used were prepared as described earlier. Other reagents used were PP, THF, and CH$_2$Cl$_2$ which was dried with 3 Å molecular sieves and distilled before use. Procedure B was used to carry out the experiments in CH$_2$Cl$_2$.

As observed previously, similar stereoselectivities (75–85% e.e. in the reduction of AP at −70° C.) were obtained in the asymmetric hydride reduction of alkyl aryl ketones using various NaAl(TADDOLate)H$_2$ complexes in solvents such as THF, DME and diglyme. In contrast, when the solvent used is CH$_2$Cl$_2$, the stereoselectivity of the same reaction under similar reduction conditions decreased by half. These results (entries 3–6 of Table 26) confirm the earlier finding that the stereoselectivity of asymmetric hydride reduction of ketones (PP in particular) using CH$_2$Cl$_2$ is lower compared to the stereoselectivity of the same reaction using ether-type solvents.

Example 44

PENTOL as Chiral Auxiliary in Tandem Reduction-HG Complexation Using PP as Substrate The title experiments used Procedure B in the second stage of the experiments during which crystallization was allowed to occur by leming the solvent evaporate slowly at room temperature.

TABLE 26

Asymmetric reduction of PP in $CH_2Cl_2$
using various TADDOLs as chiral auxiliaries*

| | | In situ preparation of NaAl(L*)H$_2$ | | Asymmetric reduction of PP | | | |
|---|---|---|---|---|---|---|---|
| Entry | TADDOL | Volume of H$_2$ gas evolved, ml, observed/calc | Molar ratio Al:PP | Solvent | °C./h | Conversion of PP into PEP, % (GC) | e.e. for PEP obtained, % (GC) |
| 1 | (−)-DDM | 24.9/23.5 | 1:1 | THF | −70/20, then −70 → 20/1 | 84 | 83 (S) |
| 2 | (−)-DDM | 25.8/23.5 | 1:1 | $CH_2Cl_2$ | −70/20, then −70 → 20/1 | 82 | 43 (S) |
| 3 | (−)-DDM | 25.2/23.5 | 1:0.5 | $CH_2Cl_2$ | −70/24 | 100 | 26 (S) |
| 4 | (−)-PENTOL | 25.2/23.5 | 1:0.5 | $CH_2Cl_2$ | −70/24 | 100 | 41 (S) |
| 5 | (−)-CPT | 25.2/23.5 | 1:0.5 | $CH_2Cl_2$ | −70/24 | 86 | 31 (S) |
| 6 | (−)-ITM | 25.2/23.5 | 1:0.5 | $CH_2Cl_2$ | −70/24 | 99 | 19 (S) |

All experiments shown were carried out using 0.5 mmol (27 mg) of SAH, 0.525 mmol of L* and 7 ml of a solvent.

Higher stereoselectivity during stage 1 of the above reaction was obtained at 0° C. than at −20° C. (see entries 1 and 2, 3, and 4 of Table 27). However, the use of Procedure B in stage 2 of the tandem procedure (entries 2 and 4) yielded unsatisfactory results compared to when Procedure C was used (entries 1 and 3). Also, no enantiomeric enrichment of (S)-PET via inclusion crystallization with the host (−)-PENTOL was observed (Stage 2). Earlier and more recent data suggest that PENTOL, unlike DDM, is a poor chiral auxiliary in a tandem reduction-HG complexation procedure, but it may be used along with other TADDOLs in a one-step asymmetric hydride reduction of alkyl aryl ketones.

Example 45

Comparison of DDM-derived Reducing Agents Based on SAH and LAH in Asymmetric Hydride Reduction of the N-acylated Imine, ADPI Substitution of the third hydride in NaAl(DDM)H$_2$ by an ethoxide group resulted in a considerably lower enantioselectivity in the hydride reduction of the C=N bond (from 77% to 30–40% e.e.; see entries 1 and 3, 2 and 4 of Table 28). As in the asymmetric reduction of alkyl

TABLE 27

Tandem asymmetric reduction - HG complexation procedure
using PP as substrate and (−)-PENTOL as chiral auxiliary[a]

| | Reduction of PP with in situ prepared NaAl[(−)-PENTOL]H$_2$ (Stage 1), THF | | | Isolation of sec-alcohol (PEP) from the reaction mixture in the form of HGC with (−)-PENTOL (Stage 2) | | | | Yield of PEP included into HGC, % (GC) | e.e. of PEP included into HGC, % (GC) | Degree of the ligand recovery, % (weight) |
|---|---|---|---|---|---|---|---|---|---|---|
| Entry | °C./h | Conversion of PP, % (GC) | e.e. for PEP, % (GC) | Procedure | Solvent (mL) | Composition of cryst. solid (NMR) L*, mg | PEP, mg | | | |
| 1 | −20/24 | 100 | 64 (S) | C | THF (1) - hexane (5) | 155 | 6 | 18 | 60 (S) | 60 |
| 2 | 0/20 | 100 | 68 (S) | B | THF (1) - hexane (5) | 166 | 30 | 91 | 71 (S) | 64 |
| 3 | −20/24 | 100 | 65 (S) | C | ether (1) - hexane (5) | 194 | —[c] | — | — | 75 |
| 4 | 0/20 | 100 | 74 (S) | B | ether (1) - hexane (5) | 219 | 8.5 | 26 | 72 (S) | 84 |

[a]0.5 mmol (27 mg) of SAH, 0.525 mmol (260 mg) of (−)-PENTOL and 7 ml of THF were used for in situ preparation of the dihydride complex in each experiment; the molar ratio of Al:PP is 1:0.5.
[b]Relative to the starting PP.
[c]The isolated solid contained only a negligible amount of PEP.

aryl ketones, the stereoselectivity of reduction of ADPI with dihydride complexes based on SAH and DDM was at least twice as high as the stereoselectivity of reduction using reagents based on LAH (lithium aluminum hydride) (see entries 1 and 5, 2 and 6 of Table 28). These results illustrate new advantages of the TADDOL-derived complexes (having a $C_2$ symmetry) over the monohydride and the advantages of using the dihydride NaAl(TADDOLate)H$_2$ as stereoselective reducing agents.

dissolved in hot benzene followed by addition of hot hexane. The resulting solution was allowed to cool down to room temperature. Crystals formed within 3–5 minutes at room temperature after which the mixture was allowed to stand overnight at room temperature. The crystalline HGC was then filtered off and washed with 2 ml of 1:5 ether-hexane. After drying the crystals at room temperature in vacuo (1–2

TABLE 28

Comparison of DDM-derived reducing agents based on SAH and LAH in the asymmetric hydride reduction of N-acylated imine, ADPI*

| | In situ preparation of reducing agent (room temp) | | | | | Asymmetric reduction of ADPI | |
|---|---|---|---|---|---|---|---|
| Entry | Starting M + AlH$_4^-$ | L* | Achiral ligand (AL) | Molar ratio Al:L*:AL | °C./h | Conversion of ADPI, % (HPLC) | e.e. for N-DPP-PEA, % (HPLC)[c] |
| 1 | M$^+$ = Na$^+$ | (−)-DDM | — | 1:1.05:0 | −20/20 | 97 | 77 (S) |
| 2 | M$^+$ = Na$^+$ | (+)-DDM | — | 1:1.05:0 | −20/20 | 95 | 77 (R) |
| 3 | M$^+$ = Na$^+$ | (−)-DDM | EtOH | 1:1:1 | −20/20 | 94 | 30 (S) |
| 4 | M$^+$ = Na$^+$ | (+)-DDM | EtOH | 1:1:1 | −20/20 | 74 | 43 (R) |
| 5 | M$^+$ = Li$^+$ | (−)-DDM | — | 1:1.05:0 | −20/20 | >99 | 30 (S) |
| 6 | M$^+$ = Li$^+$ | (+)-DDM | — | 1:1.05:0 | −20/20 | 93 | 30 (R) |

*0.5 mmol of M$^+$AlH$_4^-$, 0.167 mmol (53 mg) of ADPI and 7 mL of THF were used in each experiment (molar ratio Al:ADPI is 1:0.33).

Example 46
Resolution of (±)-PL Via Inclusion Crystallization with (R)-TPED in Benzene-hexane In carrying out stage 1 of (±)-PL resolution using the host (R)-TPED, both the host and the guest compounds were torr), they were analyzed by NMR and GC. Stages 2 and 3 of the crystallization step were performed as in Stage 1 except that the crystallization step was initially conducted at room temperature for 30 minutes and then at 0–3° C. for 24 hours. Table 29 shows the results.

TABLE 29

Resolution of (±)-PL using a 3-step inclusion crystallization with (R)-TPED from benzene-hexane

| | | The inclusion crystallization conditions | | | | | Starting | Crystalline 1:1 HGC | | e.e. of PL |
|---|---|---|---|---|---|---|---|---|---|---|
| | | (R)-TPED mmol (mg) | (±)-PL, mmol (mg) | 1:1 HGC mg | e.e. of PL included into HGC, % (GC) | Solvent (ml) | H*:G molar ratio in solution | Yield mg | %[a] | included into HGC, % (GC) |
| Entry | Stage | | | | | | | | | |
| 1 | Stage 1 | 0.5 (145) | 1 (130) | — | — | benzene (2)-hexane (6) | 1:2 | 219 | 100 | 29 (S) |
| | Stage 2 | — | — | 199 | 29 (S) | benzene (1.9)-hexane (3.8) | 1:1 | 119.5 | 60 | 45 (S) |
| | Stage 3 | — | — | 82 | 45 (S) | benzene (0.8)-hexane (1.6) | 1:1 | 47.5 | 58 (35)[b] | 83 (S) |
| 2 | Stage 1 | 0.5 (145) | 1 (130) | — | — | benzene (2)-hexane (5) | 1:2 | 190 | 90.5 | 54 (S) |
| | Stage 2 | — | — | 165 | 54 (S) | benzene (1.5)-hexane (3) | 1:1 | 114 | 70 | 79 (S) |
| | Stage 3 | — | — | 83 | 79 (S) | benzene (0.8)-hexane (1.6) | 1:1 | 49.5 | 60 (38)** | 92.5 (S) |
| | Stage 1 | 0.25 (73) | 0.5 (65) | — | — | benzene (2)-hexane (4) | 1:2 | 78.6 | 75 | 43 (S) |

[a]Relative to (R)-TPED or to HGC isolated during the preceding stage.
[b]Relative to the starting (R)-TPED.

Compared to earlier results, the above experiments showed markedly improved e.e. values of PL, although the chemical yield of the (R)-TPED*complex hardly changed. A 3-step inclusion crystallization from benzene-hexane in the above experiment gave a chemical yield of 38% (with respect to starting reagents) and an e.e. of 92.5% (S) for the (S)-PL complex. In contrast, when a 1-step inclusion crystallization from a THF-hexane solvent mixture was conducted using the same host and guest compounds, the e.e. was only 85% (and the chemical yield 39%). Further improvement in both chemical yield and e.e. could be probably be attained using a 3-step resolution of (±)-PL with (R)-TPED from benzene-hexane or toluene-hexane. In terms of stereoselectivity, these experiments demonstrate the advantage of a 3-step optical resolution procedure over a 1-step procedure.

Example 47

Asymmetric Catalytic Reduction of ACA

The following reagents were used in these experiments: SAH; (Z)-ACA; and Co(BSIC)$_2$ synthesized as described previously and purified by recrystallization from THF. As previously observed, the reduction of ACA in THF with NaAl(o-tert-Bu)$_3$H or NaAl[(±)-DDM]H$_2$ did not proceed in the absence of a catalyst at room temperature as shown by NMR and HPLC. Table 30 below shows the results obtained when a catalyst, Co(BSIC)$_2$, was used in ACA reduction using similar conditions and the same hydride donors.

TABLE 30

Attempts at asymmetric hydride reduction of ACA catalyzed by Co(BSIC)$_2$.[a]

| Entry | Hydroaluminate | The Al:ACA:Co molar ratio | °C./h | Conversion of ACA into APA (NMR) |
|---|---|---|---|---|
| 1 | NaAl(O-tert-Bu)$_3$H | 1:0.25:0 | 20/24 | 0 |
| 2 | NaAl(O-tert-Bu)$_3$H | 1:0.25:0.1 | 20/24 | 0 |
| 3 | NaAl[(±)-DDM]H$_2$ | 1:0.33:0 | 20/24 | 0[b] |
| 4 | NaAl[(±)-DDM]H$_2$ | 1:0.33:0.1 | 20/24 | 0 |

[a]1 mmol of SAH and 10 ml of THF were used in each experiment.
[b]Determined by HPLC Both hydride donors were prepared in situ by adding a THF solution of an achiral ligand to a THF solution of SAH at room temperature. The solution thus obtained was added to solid ACA followed by addition of the catalyst Co(BSIC)$_2$ (in a THF solution) into the ACA solution. The reaction was quenched with H$_2$O.

When NaAl(O-tert-Bu)$_3$H or NaAl[(±)-DDM]H$_2$ was used as hydride donor and Co(BSIC)$_2$ as catalyst, no catalytic reduction of ACA into APA at room temperature occurred—even after letting the reaction mixture stand for 24 hours. The use of other hydride donors and catalysts in the asymmetric hydride reduction of ACA (using the same hydroaluminates) should therefore be investigated.

Example 48

Study of Stability of NaAl(ACA)H$_2$ in THF

As shown earlier, ACA, when reacted with NaAl (OCH$_2$CH$_2$OCH$_3$)H$_2$ or NaAl[(±)-DDM]H$_2$, liberates two equivalents of H$_2$ gas due to the acidic nature of the hydrogen belonging to the NHCO group. In addition, it is believed that ACA cannot be simultaneously used as a substrate and as an SAH modifier due to the formation of complex (I) below:

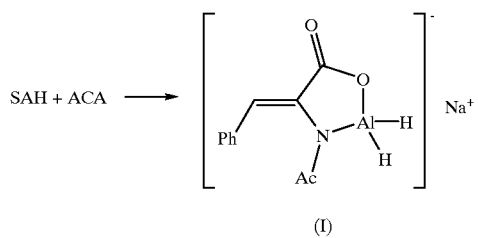

(I)

If complex (I) were stable enough at temperatures normally used in hydride-transfer reactions, complex (I) in combination with a chiral catalyst (excluding any achiral ligand) could be the simplest catalytic system for the asymmetric hydride reduction of ACA. The experiments below were conducted to investigate the stability of complex (I) at different temperatures using THF as solvent. A 5 ml THF solution containing 0.5–1.0 mmol ACA was added dropwise (with stirring) to a 2 ml THF solution containing 1 mmol SAH. The resulting clear yellow solution comprising complex (I) was allowed to stand at a particular temperature from 15 minutes to 90 hours. Afterwards, the mixture was quenched with 90% MeOH, and the volume of H$_2$ gas evolved was measured.

As can be seen from results summarized in Table 31, a decrease in hydride content corresponding to the loss of one hydride of complex (I) took place even at −20° C. (for a period of 1 hour or less; see entries 4, 5 and 15). Further allowing the solution to stand at −20° C. for at least 20 hours resulted in just a slight decrease in the remaining hydride content (see entries 14–17). This cannot be explained by the reduction of the C=C bond in ACA because the NMR spectra of the products isolated after quenching (entries 6, 9, 13, 16) show no conversion of ACA into APA at room temperature even after 20 hours. A reasonable explanation is that the acetyl group of ACA in (I) is easily eliminated upon reaction with aluminum hydride. This side reaction may be favored in a reaction involving a shift of the nitrogen's non-bonded electron pair to the aluminum ion (the transition state A):

TABLE 31

Stability of NaAl(ACA)H$_2$ in THF solvent at different temperatures[a]

| | Solution of NaAl(ACA)H$_2$ in THF | | | Stability of a solution of the complex | |
|---|---|---|---|---|---|
| Entry | Starting SAH:ACA molar ratio | Volume of H$_2$ gas evolved, ml (observed/ calc) | Exposure condition of the solution, °C./h | Volume of H$_2$ gas evolved after quenching the exposed solution, ml, observed/calcd | Conversion of ACA into APA, % (NMR) |
| 1 | 1:1 | 45.4/44.8 | 20/0.25 | 13.6/44.2 | —[b] |
| 2 | 1:1 | 48/48 | 20/0.5 | 11.8/41.6 | —[b] |
| 3 | 1:1 | 48/48 | 20/1 | 10.0/41.6 | —[b] |
| 4 | 1:1 | 42.8/48 | −20/0.25 | 28.2/46.8 | —[b] |
| 5 | 1:1 | 43.7/48 | −20/0.5 | 24.3/45.9 | —[b] |
| 6 | 1:1 | 44.6/48 | −20/1 | 29.1/45.0 | 0 |
| 7 | 1:0.5 | 24.6/22.4 | 18/0.25 | 45.5/65 | —[b] |
| 8 | 1:0.5 | 25.5/22.4 | 18/1 | 36/64.1 | —[b] |
| 9 | 1:0.5 | 25.5/22.4 | 18/20 | 7.5/64.1 | 0 |
| 10 | 1:0.5 | 25.5/22.4 | 18/90 | 8.2/64.1 | —[b] |
| 11 | 1:0.5 | 22.5/22.4 | 0/0.25 | 49.7/67.1 | —[b] |
| 12 | 1:0.5 | 24.4/22.4 | 0/1 | 44.1/65.2 | —[b] |
| 13 | 1:0.5 | 24.4/22.4 | 0/20 | 28.1/65.2 | 0 |
| 14 | 1:0.5 | 24.5/22.4 | −20/0.25 | 59.4/65.1 | —[b] |

TABLE 31-continued

Stability of NaAl(ACA)H$_2$ in THF solvent at different temperatures[a]

| | Solution of NaAl(ACA)H$_2$ in THF | | | Stability of a solution of the complex | |
|---|---|---|---|---|---|
| Entry | Starting SAH:ACA molar ratio | Volume of H$_2$ gas evolved, ml (observed/ calc) | Exposure condition of the solution, ° C./h | Volume of H$_2$ gas evolved after quenching the exposed solution, ml, observed/calcd | Conversion of ACA into APA, % (NMR) |
| 15 | 1:0.5 | 26.4/22.4 | −20/1 | 46.2/63.2 | —[b] |
| 16 | 1:0.5 | 26.4/22.4 | −20/20 | 42.4/63.2 | 0 |
| 17[c] | 1:0.5 | 28.1/22.4 | −20/20 | 45.0/61.5 | —[b] |

[a]1 mmol (54 mg) of SAH was used in each experiment.
[b]Not determined.
[c]Altered sequence of mixing the starting reagents: for in situ preparation of NaAl(ACA)H$_2$, a solution of ACA in THF was added to a solution of SAH

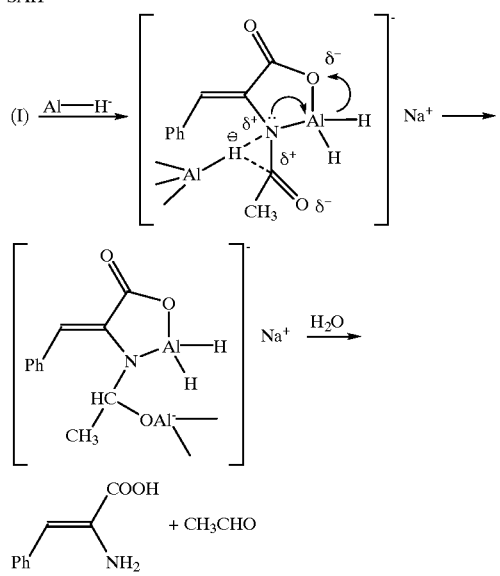

This was confirmed by the NMR spectra of the products obtained after quenching the hydride complex or complexes: in some experiments, the integral intensity of the signal belonging to the CH$_3$CO group's protons (at 2 ppm) was considerably less than that of the phenyl group's protons. Non-modified SAH thus appears unsuitable as hydride donor in the catalytic hydride reduction of ACA into APA even at low reaction temperatures.

Example 49

HG Complexation Between (R) -TPED and PL. Preparation of HGC's of (R)-TPED with 3-butyne-2-ol, Glycidol and Epichlorohydrine As can be seen in Expts. 1 and 4 in Table 32, an improvement in the e.e. values from 75% (S) to 86% (S) was obtained when the solvent was changed from THF-hexane to ether-hexane. On the other hand, the use of benzene-hexane as solvent consistently produced e.e. values no higher than 60% (S). Lowering the reaction temperature from 3° C. to 0° C. produced a marked improvement from 75% (S) in Expt. 1 to 85% (S) in Expt. 12–1. When a smaller volume of THF-hexane was used, the e.e. value jumped up to 98% (S) (see Expt. 12–2). This suggests that the amount of solvent relative to the guest compound can have a significant impact on the optical resolution of PL. Ether-hexane or hexane alone failed to produce an HGC with 3-butyne-2-ol, glycidol, and epichlorohydrine. The results of Expts. 5 and 6 suggest that the optical resolution of PL via HG complexation could be improved by extending the reaction duration from 1 hour to 24 hours.

TABLE 32

HG Complexion between (R)-TPED and PL. Preparation of HGC's of (R)-TPED with 3-butyne-2-ol, glycidol and epichlorohydrine

| | | | | HG complexation conditions | | | Crystalline HGC* | | e.e. for guest compound included into HGC, % (GC) |
|---|---|---|---|---|---|---|---|---|---|
| | (R)-TPED, | | Guest compound (G) | | | | Yield | | |
| | mmol | | mmol | | | | | | |
| Entry | (mg) | Name | (mg) | Solvent (ml) | ° C./h | Procedure | mg | %[b] | |
| 1 | 0.25 (73) | (±)-PL | 0.5 (65) | THF (0.5)-hexane (5) | 3/24 | A | 53 | 50 | 75 (S) |
| 2 | 0.5 (145) | (±)-PL | 1 (130) | THF (0.5)-hexane (5) | 3/24 | A | 118 | 56 | 50 (S) |
| 3 | 0.5 (145) | (±)-PL | 1 (130) | THF (0.5)-hexane (5) | 0/1 | A | 97 | 46 | 40 (S) |
| 4 | 0.25 (73) | (±)-PL | 0.5 (65) | ether (2)-hexane (4) | 3/24 | A | 29 | 27 | 86 (S) |

TABLE 32-continued

HG Complexion between (R)-TPED and PL. Preparation of HGC's of (R)-TPED with 3-butyne-2-ol, glycidol and epichlorohydrine

| | | | | | | | Crystalline HGC* | | |
|---|---|---|---|---|---|---|---|---|---|
| | | HG complexation conditions | | | | | | | e.e. for guest compound included into HGC, % (GC) |
| Entry | (R)-TPED, mmol (mg) | Guest compound (G) Name | mmol (mg) | Solvent (ml) | °C./h | Procedure | Yield mg | %[b] | |
| 5 | 0.5 (145) | (±)-PL | 1 (130) | ether (2)-hexane (4) | 20/24 | A | 97 | 46 | 73 (S) |
| 6 | 0.5 (145) | (±)-PL | 1 (130) | ether (2)-hexane (4) | 20/1 | A | 80 | 38 | 55 (S) |
| 7 | 0.25 (73) | (±)-PL | 0.5 (65) | benzene (1)-hexane (5) | 25/24 | A | 80 | 76 | 60 (S) |
| 8 | 0.5 (145) | (±)-PL | 1 (130) | benzene (1)-hexane (5) | 25/24 | A | 90 | 86 | 55 (S) |
| 9 | 0.5 (145) | (±)-PL | 1 (130) | benzene (1.5)-hexane (5) | 25/24 | A | 83 | 79 | 60 (S) |
| 10 | 0.5 (145) | (±)-PL | 1 (130) | benzene (1)-hexane (3) | 25/24 | A | 63 | 60 | 54 (S) |
| 11 | 0.5 (145) | (±)-PL | 1 (130) | THF (3)-H$_2$O (9) | 0/48 | A | —[c] | — | — |
| 12-1 | 0.5 (145) | (±)-PL | 1 (130) | THF (1)-hexane (10) | 0/24 | A | 82 | 39 | 85 (S) |
| 12-2 | 0.5 (145) | (±)-PL | 1 (130) | THF (0.3)-hexane (3) | 0/24 | A | 30 | 37 | 98 (S) |
| 13 | 0.25 (73) | (±)-3-Butyne-2-ol | 1 (70) | ether (1)-hexane (5) | −20/24 | A | 51[d] | — | — |
| 14 | 0.25 (73) | Glycidol | 1 (74) | hexane (5) | 20/48 | B | 102[e] | — | — |
| 15 | 0.25 (73) | Epichlorohydrine | 1 (92) | hexane (5) | 20/48 | B | 64[d] | — | — | a) (R)-TPED forms with (S)-PL an HGC having a 1:1 stoichiometry.
b) With respect to the starting (R)-TPED.
c) Colloid-like mixture was obtained after addition of H$_2$O to a solution of (R)-TPED and PL in THF.
d) (R)-TPED was the only crystalline product isolated.
e) A mixture of crystalline (R)-TPED and oil was obtained.

LIST OF ABBREVIATIONS

ACA: Z-N-acetyl-α-aminocinnamic acid
ADPI: acetophenone N-(diphenylphosphinyl)imine
AMDB: 2-amino-3-methyl-1,1-diphenylbutanol
AP: acetophenone
APA: N-acetylphenylalanine
APAH: acetophenone acetylhydrazone
BBIC: (1R,2R)-N,N'-bis(benzaldimino)cyclohexane
BINAL: complex formed from equimolar amounts of lithium aluminum hydride, 2,2'-dihydrox-1,1'-binaphthyl, and ethanol
BINAP: 2,2'-Bis(diphenylphosphino)-1,1'-binaphthyl
BSIC: (1R,2R)-N,N'-bis(salicylaldimino)cyclohexane
CMK: cyclopropylmethyl ketone
CPE: α-cyclopropyl ethanol
(−)-CPT: (−)-2,3-O-cyclopentylidene-1,1,4,4-tetraphenyl-L-threitol
(+)-CPT: (+)-2,3-O-cyclopentylidene-1,1,4,4-tetraphenyl-L-threitol
(−)-CYTOL: (−)-2,3-O-cyclohexylidene-1,1,4,4-tetraphenyl-L-threitol
(+)-CYTOL: (+)-2,3-O-cyclohexylidene-1,1,4,4-tetraphenyl-L-threitol
DAMB: (S)-1,1-diphenyl-2-amino-3-methylbutanol
(−)-DDM: (R,R)-(−)-trans-(α',α',(2,2-dimethyl-1,3-dioxolane-4,5-diyl)-bis-diphenylmethanol)
(+)-DDM: (S,S)-(−)-trans-(α',α',(2,2-dimethyl-1,3-dioxolane-4,5-diyl)-bis-diphenylmethanol)
DMFD: 4,4-dimethyl-2,3(5H)-furandione
DPP: diphenylphosphinyl
(−)-DPPD: (S)-(−)-1,1-Diphenyl-1,2-propanediol
ECAA: ethyl-4-chloroacetoacetate
ECHB: ethyl-4-chloro-3-hydroxybutyrate
EHAA: ethyl-4-hydroxyacetoacetate
EHPB: ethyl 2-hydroxy-4-phenylbutyrate
EOPB: ethyl 2-oxo-4-phenylbutyrate
(−)-FLUTOL: (−)-2,3-O-(9-fluorenylidene)-1,1,4,4-tetraphenyl-L-threitol
G: guest compound
H*: chiral host compound
HGC: host-guest complex
IDOB: (S)-4-isopropyl-5,5-diphenyloxazaboroldine
IPG: α,β-isopropylideneglycerol
(−)-ITM: (−)-2,3-O-isopropylidene-1,1-4,4-tetra-(4-methoxyphenyl)-L-threitol
L*: chiral ligand MET: 2-methoxyethanol Na-TADDAL-H$_2$: sodium aluminum dihydride complexes derived from ($\alpha,\alpha,\alpha',\alpha'$)-tetraaryl-1,3-dioxolane-4,5-dimethanols PEA: $\alpha$-phenylethylamine (−)-PENTOL: (−)-2,3-O-(3-pentylidene)-1,1,4,4-tetraphenyl-L-threitol PEP: $\alpha$-phenylpropanol.

PET: $\alpha$-phenylethanol

PL: pantolactone (2-hydrox-3,3-dimethyl-y-butyrolactone)

PP: propiophenone

SAH: sodium aluminum hydride

TADDAL: a TADDOL complex containing Al

TADDOL: ($\alpha,\alpha,\alpha',\alpha'$-tetraaryl-1,3-dioxolane-4,5-dimethanol

TEBA: triethylbenzylammonium chloride (+)-TPED: (R)-(+)-1,1,2-Triphenyl-1,2-ethanediol

What is claimed is:

1. A method for obtaining an enantiomeric excess of a reaction product through a tandem process comprising the steps of:

enantioselectively reducing a chemical entity that has a carbonyl group or carbonyl equivalent by admixing the chemical entity with a metal hydride complex which is derived from a metal hydride and which comprises a chiral ligand and at least two equivalents of hydrides to form a reaction mixture and allowing the reaction mixture to react for a time sufficient to reduce the carbonyl group or carbonyl equivalent, thus forming a reduction product in a solution that contains a solvent;

quenching the reaction to terminate the reaction;

allowing the quenched reaction mixture to stand for a period of time sufficient to form crystals comprising the ligand and the reduction product; and recovering the reduction product from the crystals.

2. The method of claim 1 which further comprises preparing the reducing agent in situ by admixing the metal hydride and chiral ligand in a solvent which is an alkyl hydrocarbon, an aromatic hydrocarbon or a mixture thereof.

3. The method of claim 1 which further comprises preparing the reducing agent in situ by admixing a metal hydrides solution and chiral ligand solution.

4. The method of claim 2 which further comprises providing an achiral ligand in the metal hydride complex.

5. The method of claim 1 wherein the crystals are separated from the remaining reaction mixture prior to recovering the reduction product.

6. The method of claim 4 which further comprises recrystallizing the reduction product.

7. The method of claim 1 wherein the metal-hydride complex comprises aluminum and a cation selected from a group consisting of Na$^+$, Li$^+$, and K$^+$.

8. The method of claim 1 wherein the crystals are formed by evaporating the solvent to allow the reduction product and ligand to co-crystallize.

9. The method of claim 1 wherein the crystallization step is performed in a suspension.

10. The method of claim 1 which further comprises adding a solvent for the crystallization step which is different from that used in the reduction step, wherein the solvent is selected from a group consisting of alky hydrocarbons, aromatic hydrocarbons, or mixtures thereof.

11. The method of claim 4 wherein the different solvent is selected from the group consisting of THF, DME, diglyme, triglyme, hexane, heptane, benzene, toluene, xylene, chlorobenzene, CH$_2$Cl$_2$, ether and mixtures thereof.

12. The method of claim 2 wherein the crystals that are formed comprise ternary complexes comprising the reduction product, the ligand, and the solvent.

13. The method of claim 2 wherein the ligand forms a binary complex with the solvent and then the reduction product displaces the solvent molecule from the binary complex during the crystallyiation stage.

14. The method of claim 1 wherein the reduction product is separated from the other chemical components of the crystal by heating the crystals at a temperature high enough to achieve efficient separation but low enough to prevent thermal decomposition of the reduction product.

15. The method of claim 1 wherein the ligand is selected from a group consisting of (R,R)-(−)-trans-($\alpha',\alpha'$(2,2-dimethyl-1,3-dioxolane-4,5-diyl)-bis-(diphenylmethanol); (S,S)-(+)-trans-($\alpha',\alpha'$(2,2-dimethyl-1,3-dioxolane-4,5-diyl)-bis-(diphenylmethanol); (−)-2,3-O-cyclohexylidene-1,1,4,4-tetra-phenyl-L-threitol; (−)-2,3-O-cyclopentylidene-1,1,4,4-tetra-phenyl-L-threitol; (−)-2,3-O-(9-fluorenylidene)-1,1,4,4-tetra-phenyl-L-threitol; (−)-2,3-O-isopropylidene-1,1-4,4-tetra-(4-methoxyphenyl)-L-threitol; (S)-(−)-1,1-Diphenyl-1,2-propanediol; (R)-(+)-1,1,2-Triphenyl-1,2-ethanediol; 2,2'-Bis(diphenylphosphino)-1,1'-binaphthyl; acetophenone acetylhydrazone; Z-N-acetyl-a-aminocinnamic acid; N-acetylphenylalanine; 4,4-dimethyl-2,3(5H)-furandione; acetophenone N-(diphenylphosphinyl) imine; pantolactone (2-hydroxy-3,3-dimethyl-y-butyrolactone); and (−)-2,3-O-(3-pentylidene)-1,1,4,4,-tetra-phenyl-L-threitol.

16. The method of claim 1 in which the reducing agent is derived from sodium aluminum hydride modified by a tert-butoxy group.

17. The method of claim 1 wherein the reaction is quenched to deactivate unreacted reducing agent.

* * * * *

UNITED STATES PATENT AND TRADEMARK OFFICE
CERTIFICATE OF CORRECTION

PATENT NO. : 6,166,260

DATED : December 26, 2000

INVENTOR(S) : Glenn L. Heise

It is certified that error appears in the above-identified patent and that said Letters Patent is hereby corrected as shown below:

In Column 74, claim 13, line 4, please replace "crystallyiation" with --crystallization--.

Signed and Sealed this

Fifteenth Day of May, 2001

Attest:

NICHOLAS P. GODICI

Attesting Officer    Acting Director of the United States Patent and Trademark Office